US012770714B2

(12) United States Patent
Abdueva

(10) Patent No.: US 12,770,714 B2
(45) **Date of Patent: *Oct. 20, 2026**

(54) METHODS FOR FRAGMENTOME PROFILING OF CELL-FREE NUCLEIC ACIDS

(71) Applicant: GUARDANT HEALTH, INC., Redwood City, CA (US)

(72) Inventor: Diana Abdueva, Orinda, CA (US)

(73) Assignee: GUARDANT HEALTH, INC., Palo Alto, CA (US)

( * ) Notice: Subject to any disclaimer, the term of this patent is extended or adjusted under 35 U.S.C. 154(b) by 1245 days.

This patent is subject to a terminal disclaimer.

(21) Appl. No.: 16/315,573

(22) PCT Filed: Jul. 6, 2017

(86) PCT No.: PCT/US2017/040986

§ 371 (c)(1),
(2) Date: Jan. 4, 2019

(87) PCT Pub. No.: WO2018/009723

PCT Pub. Date: Jan. 11, 2018

(65) Prior Publication Data

US 2019/0287645 A1 Sep. 19, 2019
US 2026/0204345 A9 Jul. 16, 2026

Related U.S. Application Data

(60) Provisional application No. 62/489,399, filed on Apr. 24, 2017, provisional application No. 62/437,172, filed on Dec. 21, 2016, provisional application No. 62/420,167, filed on Nov. 10, 2016, provisional application No. 62/359,151, filed on Jul. 6, 2016.

(51) Int. Cl.

| | |
|---|---|
| ***G16B 20/10*** | (2019.01) |
| ***G16B 20/00*** | (2019.01) |
| ***G16B 30/00*** | (2019.01) |
| ***G16B 40/00*** | (2019.01) |

(52) U.S. Cl.

CPC ............. *G16B 20/10* (2019.02); *G16B 20/00* (2019.02); *G16B 30/00* (2019.02); *G16B 40/00* (2019.02)

(58) Field of Classification Search

CPC ............ C12Q 2600/156; C12Q 1/6869; C12Q 2537/143; C12Q 1/6827; C12Q 1/6874; C12Q 2537/165; C12Q 2537/16; C12Q 2600/154; C12Q 2600/158; C12Q 2600/172; C12Q 1/6886; G16B 20/00; G16B 20/10; G16B 20/20; G16B 40/00; G16B 20/40; G16B 30/00; G16B 25/00; G16B 30/10; G16B 5/00; G16B 5/20; G16B 25/10; G16B 50/30; G16B 40/30; G16B 40/20; G06V 10/70; G06V 10/766; G06V 10/84; G06N 20/00; G06N 3/08; G06N 7/01; G06N 3/047; G06N 3/088; G06N 3/09; G06N 3/0985; G16H 50/70; G16H 50/20; G16H 10/60; G06F 18/24; G06F 18/241; G06F 18/27; G06F 18/251; G06F 18/253; G06F 18/256; G06F 16/285; G06F 2218/08; G06F 2218/12; G06F 17/14; G06F 17/156; G06F 17/175; G06F 17/18

See application file for complete search history.

(56) References Cited

U.S. PATENT DOCUMENTS

| | | | | |
|---|---|---|---|---|
| 9,218,449 | B2 | 12/2015 | Lo et al. | |
| 9,598,731 | B2 | 3/2017 | Talasaz | |
| 9,850,523 | B1 * | 12/2017 | Chudova | C12Q 1/6827 |
| 9,892,230 | B2 | 2/2018 | Lo et al. | |
| 10,318,704 | B2 * | 6/2019 | Chudova | G16B 20/10 |
| 10,741,269 | B2 * | 8/2020 | Chudova | G16B 20/10 |
| 11,062,791 | B2 * | 7/2021 | Chudova | G16B 5/00 |

(Continued)

FOREIGN PATENT DOCUMENTS

| | | |
|---|---|---|
| CN | 101901345 A | 12/2010 |
| CN | 103003447 A | 3/2013 |

(Continued)

OTHER PUBLICATIONS

Ralla, B. et al. Nucleic acid-based biomarkers in body fluids of patients with urologic malignancies. (May 29, 2014) Critical Reviews in Clinical Laboratory Sciences. vol. 51 No. 5, p. 200-231. (Year: 2014).*

(Continued)

*Primary Examiner* — Mary K Zeman
(74) *Attorney, Agent, or Firm* — Timothy A. Hott

(57) ABSTRACT

The present disclosure contemplates various uses of cell-free DNA. Methods provided herein may use sequence information in a macroscale and global manner, with or without somatic variant information, to assess a fragmentome profile that can be representative of a tissue of origin, disease, progression, etc. In an aspect, disclosed herein is a method for determining a presence or absence of a genetic aberration in deoxyribonucleic acid (DNA) fragments from cell-free DNA obtained from a subject, the method comprising: (a) constructing a multi-parametric distribution of the DNA fragments over a plurality of base positions in a genome; and (b) without taking into account a base identity of each base position in a first locus, using the multi-parametric distribution to determine the presence or absence of the genetic aberration in the first locus in the subject.

20 Claims, 39 Drawing Sheets

(56) References Cited

U.S. PATENT DOCUMENTS

| | | | | |
|---|---|---|---|---|
| 11,242,569 | B2 * | 2/2022 | Eltoukhy | C12Q 1/6874 |
| 11,952,616 | B2 * | 4/2024 | Kennedy | C12Q 1/6827 |
| 12,428,670 | B2 * | 9/2025 | Kennedy | C12Q 1/6874 |
| 2013/0085681 | A1 | 4/2013 | Deciu et al. | |
| 2015/0051087 | A1 | 2/2015 | Rabinowitz et al. | |
| 2015/0368708 | A1 | 12/2015 | Talasaz | |
| 2016/0019338 | A1 * | 1/2016 | Chudova | G16B 30/10 702/20 |
| 2016/0040229 | A1 | 2/2016 | Talasaz et al. | |
| 2016/0046986 | A1 | 2/2016 | Eltoukhy et al. | |
| 2017/0024513 | A1 * | 1/2017 | Lo | G16B 30/00 |
| 2018/0251848 | A1 | 9/2018 | Diehn et al. | |

FOREIGN PATENT DOCUMENTS

| | | | | |
|---|---|---|---|---|
| CN | 103374518 | A | 10/2013 | |
| CN | 104781421 | A | 7/2015 | |
| CN | 105408496 | A | 3/2016 | |
| CN | 105722994 | A | 6/2016 | |
| JP | 2013536679 | A | 9/2013 | |
| WO | 2010049538 | A1 | 5/2010 | |
| WO | 2013052913 | A2 | 4/2013 | |
| WO | 2013121224 | A1 | 8/2013 | |
| WO | 2013192562 | A1 | 12/2013 | |
| WO | WO-2014116598 | A2 * | 7/2014 | G16B 20/00 |
| WO | WO-2015048535 | A1 * | 4/2015 | C12N 15/10 |
| WO | 2016015058 | A2 | 1/2016 | |
| WO | 2016094853 | A1 | 6/2016 | |
| WO | WO-2017062867 | A1 * | 4/2017 | C12Q 1/6883 |

OTHER PUBLICATIONS

Paweletz et al Bias corrected targeted next generation sequencing for rapid, multiplexed detection of actionable alterations in cell-free DNA from advanced lung cancer patients. (Feb. 15, 2016) Clinical Cancer Research vol. 22, No. 4, p. 915-922, 16 pages. (Year: 2016).*

Chandrananda et al ((2015) BMC Medical Genomics 8:29; of record) (Year: 2015).*

Chandrananda, D. et al. "High-resolution characterization of sequence signatures due to non-random cleavage of cell-free DNA" BioMed Central Medical Genomics (Jun. 17, 2015) 8(29):1-19.

Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.

Ding, C. et al. "Minimum redundancy feature selection from microarray gene expression data" J Bioinform Comput Biol. Apr. 2005;3(2):185-205.

Gaffney, D.J. et al. "Controls of nucleosome positioning in the human genome." PLoS Genet. (2012) 8:e1003036.

He, X. et al. "Different mutations of the human c-mpl gene indicate distinct haematopoietic diseases" J. Hematol & Oncol (2013) 6:11.

Hyndman, R.J. (1996). Computing and graphing highest density regions. The American Statistician, 50(2), 120-126.

International search report and written opinion dated Sep. 25, 2017 for PCT/US2017/040986.

Ivanov, M. et al. "Non-random fragmentation patterns in circulating cell-free DNA reflect epigenetic regulation" BMC Genomics (2015) 16(Suppl. 13):51.

Kostyuk, S.V. et al. "An Exposure to the Oxidized DNA Enhances Both Instability of Genome and Survival in Cancer Cells" PLoS (Oct. 17, 2013) 8(10):e77469, pp. 1-23.

Liu, F.T. et al. "Isolation forest" Data Mining, 2008. ICDM'08. Eighth IEEE International Conference.

Newman, et al. An ultrasensitive method for quantitating circulating tumor DNA with broad patient coverage. Nat Med. May 2014;20(5):548-54. doi: 10.1038/nm.3519. Epub Apr. 6, 2014.

Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.

Phallen, J. et al. "Direct detection of early-stage cancers using circulating tumor DNA" Sci Trans Med (2017) vol. 9, Issue 403, eaan2415DOI: 10.1126/scitranslmed.aan2415.

Rousseeuw, P.J. et al. "A Fast Algorithm for the Minimum Covariance Determinant Estimator" Technometrics (1999) 41(3):212-223.

Schep, A.N. et al. "Structured nucleosome fingerprints enable high-resolution mapping of chromatin architecture within regulatory regions" Genome Research (2015) 25(11):1757-1770.

Scholkopf, B. et al. "Estimating the Support of a High-Dimensional Distribution" Neural Computation (2001) 13(7):1443-1471.

Snyder, M.W. et al. "Cell-free DNA Comprises an In Vivo Nucleosome Footprint that Informs Its Tissues-Of-Origin" Cell (2016) 164:57-68 & Supplemental Information.

Statham, et al. "Genome-wide nucleosome occupancy and DNA methylation profiling of four human cell lines" Genomics Data (Mar. 2015) 3:94-96.

Wand, M.P. "Fast Computation of Multivariate Kernel Estimators." Journal of Computational and Graphical Statistics (1994) 3:433-445.

Evans, A.L. et al. "Quantitative Efferocytosis Assays" Chapter 3 or Phagocytosis and Phagosomes; Botelho, R. Ed., Methods in Molecular Biology, New York, NY (2017) 1519:25-41.

Hu, Z. et al. "The main sources of circulating cell-free DNA: Apoptosis, necrosis and active secretion" Crit Rev Oncol/Hematol (2021) 157:103166 (8 pages).

Lonnbro, P. et al. "Isolation of bacteria-containing phagosomes by magnetic selection" BMC Cell Biology (2008) 9 (1):35 (11 pages).

Yin, C. et al. "Rab17 mediates differential antigen sorting following efferocytosis and phagocytosis" Cell and Death Disease (2016) 7(12):32529 (12 pages).

Chodavarapu, C. et al. "Relationship between nucleosome positioning and DNA methylation" Nature (2010) 466(7304):388-392.

Portela, A. et al. "DNA methylation determines nucleosome occupancy in the 5'-CpG islands of tumor suppressor genes" Oncogene (2013) 32(47):5421-5428.

Office Action for Brazilian Patent Application No. 11 2019 000296 0 dated Apr. 23, 2025.

* cited by examiner $$\text{cfDNA} = \sum_{\substack{\text{tissue} \\ \text{(including blood)}}} \begin{bmatrix} \text{benign systemic response} \\ \text{tumor systemic response} \\ \text{tumor microenvironment} \\ \text{tumor} \end{bmatrix}$$

FIG. 1A

$$\text{cfDNA} = \sum_{\substack{\text{tissue} \\ \text{(including blood)}}} \begin{bmatrix} \text{benign systemic response x benign clearance} \\ \text{tumor systemic response x inflammation clearance} \\ \text{tumor microenvironment x TM clearance} \\ \text{tumor x tumor clearance} \end{bmatrix}$$

FIG. 1B

Fig. 4

| | sampleid | gene | alteration | percentage | copynumber | type | mut_type | cancertype |
|---|---|---|---|---|---|---|---|---|
| 59791 | A2570201_1 | RB1 | E209* | 63.88 | NA | SNV | nonsense | Small Cell Lung Carcinoma |
| 59792 | A2570201_1 | PIK3CA | AMP | 0.00 | 3.821532 | CNV | amp | Small Cell Lung Carcinoma |
| 59794 | A2570201_1 | CCND2 | AMP | 0.00 | 2.670914 | CNV | amp | Small Cell Lung Carcinoma |
| 59795 | A2570201_1 | MYC | AMP | 0.00 | 2.598206 | CNV | amp | Small Cell Lung Carcinoma |
| 59797 | A2570201_1 | CCND1 | AMP | 0.00 | 2.585685 | CNV | amp | Small Cell Lung Carcinoma |
| 59798 | A2570201_1 | CDK4 | AMP | 0.00 | 2.486675 | CNV | amp | Small Cell Lung Carcinoma |
| 59793 | A2570201_1 | ERBB2 | AMP | 0.00 | 2.425024 | CNV | amp | Small Cell Lung Carcinoma |
| 59796 | A2570201_1 | KRAS | AMP | 0.00 | 2.384474 | CNV | amp | Small Cell Lung Carcinoma |
| 59799 | A2570201_1 | CDKN2A | G23G | 0.28 | NA | SNV | synonymous | Small Cell Lung Carcinoma |

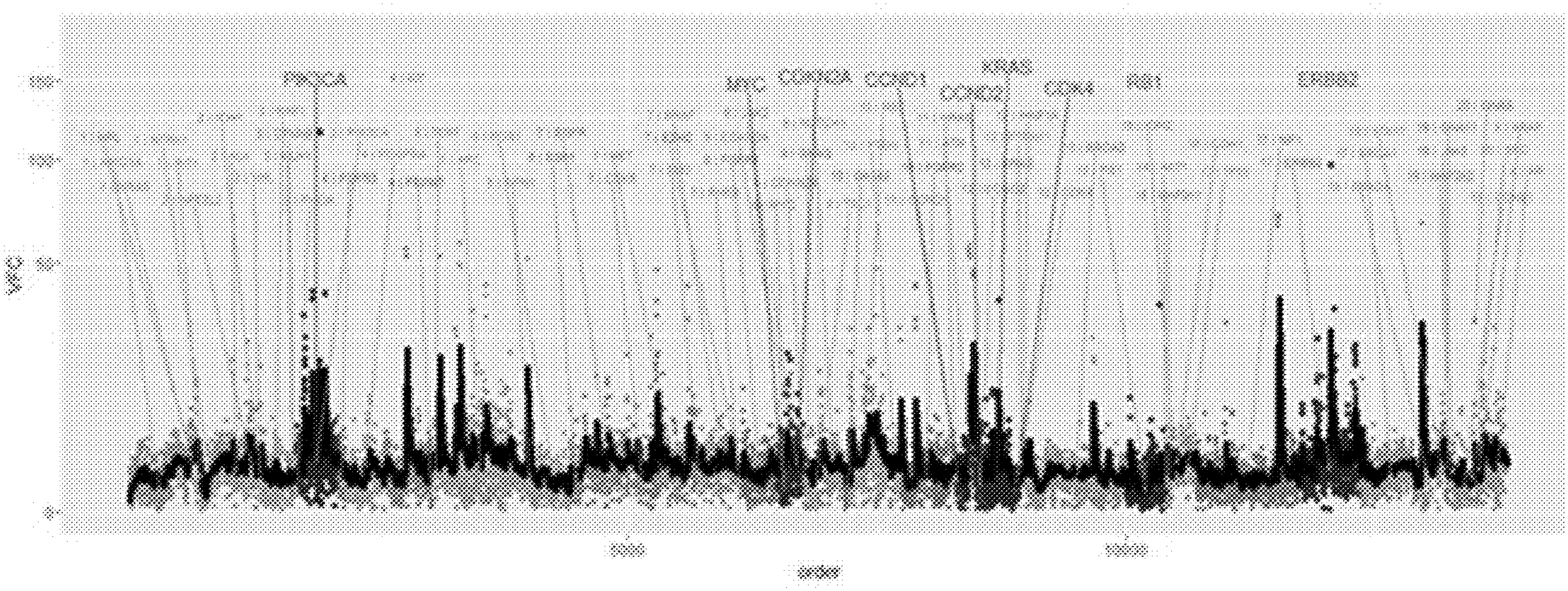

TP53

NF1 erbb2

Absolute CN

Locate nuc locations and match them to expected in normal cohort
For every nuc window in FGFR
 determine a collection of ultraconservative non-chr10 nuc sites (genomeUC)
 determine a collection of ultraconservative chr10 nuc sites (ch10UC)
Integrate over pos vs insert size density of FGFR nuc site – (UC)x aneuploidy factor (ch10UC /genomeUC)

$$p(\mathbf{X}=\mathbf{x}\,|\,\theta)=\sum_{k=1}^{K}\pi_k\,p(\mathbf{X}=\mathbf{x}\,|\,C=c_k,\theta_k)$$

*where*:

$\mathbf{X}$ is a multivariate random variable representing idividual DNA fragment unit $C$ is a categorical variable with a values from $\{c_1 ... c_k\}$ with one c's being possibly cancer $\pi_k$ is the marginal probability (the weight) of the $k^{th}$ class $\theta_k$ is the parameter estimates of the $k^{th}$ class containing the probability distributions for each column/variable

FIG. 25

METHODS FOR FRAGMENTOME PROFILING OF CELL-FREE NUCLEIC ACIDS

CROSS-REFERENCE

This application claims priority to U.S. Provisional Application No. 62/359,151, filed Jul. 6, 2016, U.S. Provisional Application No. 62/420,167, filed Nov. 10, 2016, U.S. Provisional Application No. 62/437,172, filed Dec. 21, 2016, and U.S. Provisional Application No. 62/489,399, filed Apr. 24, 2017, each of which is entirely incorporated herein by reference.

BACKGROUND

Current methods of cancer diagnostic assays of cell-free nucleic acids (e.g., DNA or RNA) focus on the detection of tumor-related somatic variants, including single nucleotide variants (SNVs), copy number variations (CNVs), fusions, and indels (i.e., insertions or deletions), which are all mainstream targets for liquid biopsy. There is growing evidence that new types of structural variants that arise as a consequence of nucleosomal positioning can be identified and measured for tumor-relevant information that, when combined with somatic mutation calling, can yield a far more comprehensive assessment of tumor status than that available from either approach alone. By analyzing an underlying non-random pattern of nucleic acid fragment distribution that is affected by chromatin organization, this set of new structural variants can be observed in samples independently from somatic variants, and indeed even in samples where no somatic variants are detected.

SUMMARY

Nucleosome positioning is a key mechanism that contributes to the epigenetic control of gene expression, is highly tissue specific, and is indicative of various phenotypical states. The present disclosure describes methods, systems, and compositions for performing nucleosome profiling using cell-free nucleic acids (e.g., cfDNA). This can be used to identify new driver genes, determine copy number variation (CNV), identify somatic mutations and structural variations such as fusions and indels, as well as identify regions that can be used in a multiplexed assay to detect any of the above variations.

The present disclosure provides various uses of cell-free nucleic acids (e.g., DNA or RNA). Such uses include detecting, monitoring and determining treatment for a subject having or suspected of having a health condition, such as a disease (e.g., cancer). Methods provided herein may use sequence information in a macroscale and global manner, with or without somatic variant information, to assess a fragmentome profile that can be representative of a tissue of origin, disease, progression, etc.

In an aspect, disclosed herein is a computer-implemented method for determining a presence or absence of a genetic aberration in deoxyribonucleic acid (DNA) fragments from cell-free DNA obtained from a subject, the method comprising: (a) constructing, by a computer, a multi-parametric distribution of the DNA fragments over a plurality of base positions in a genome; and (b) without taking into account a base identity of each base position in a first locus, using the multi-parametric distribution to determine the presence or absence of the genetic aberration in the first locus in the subject.

In some embodiments, the genetic aberration comprises a sequence aberration. In some embodiments, the sequence aberration comprises a single nucleotide variant (SNV). In some embodiments, the sequence aberration comprises an insertion or deletion (indel), or a gene fusion. In some embodiments, the sequence aberration comprises two or more different members selected from the group consisting of (i) a single nucleotide variant (SNV), (ii) an insertion or deletion (indel), and (iii) a gene fusion. In some embodiments, the genetic aberration comprises a copy number variation (CNV).

In some embodiments, the multi-parametric distribution comprises a parameter indicative of a length of the DNA fragments that align with each of the plurality of base positions in the genome. In some embodiments, the multi-parametric distribution comprises a parameter indicative of a number of the DNA fragments that align with each of the plurality of base positions in the genome. In some embodiments, the multi-parametric distribution comprises a parameter indicative of a number of the DNA fragments that start or end at each of the plurality of base positions in the genome. In some embodiments, n the multi-parametric distribution comprises parameters indicative of two or more of: (i) a length of the DNA fragments that align with each of the plurality of base positions in the genome, (ii) a number of the DNA fragments that align with each of the plurality of base positions in the genome, and (iii) a number of the DNA fragments that start or end at each of the plurality of base positions in the genome. In some embodiments, the multi-parametric distribution comprises parameters indicative of (i) a length of the DNA fragments that align with each of the plurality of base positions in the genome, (ii) a number of the DNA fragments that align with each of the plurality of base positions in the genome, and (iii) a number of the DNA fragments that start or end at each of the plurality of base positions in the genome.

In some embodiments, using the distribution comprises applying, by a computer, the multi-parametric distribution to a classifier having inputs of a plurality of other multi-parametric distributions of DNA fragments over the plurality of base positions in a genome, the other multi-parametric distributions obtained from a group selected from (a) subjects with a tissue specific cancer, (b) subjects with a particular stage of cancer, (c) subjects with an inflammatory condition, (d) subjects that are asymptomatic to cancer but have a tumor that will progress into cancer, and (e) subjects having positive or negative response to a therapy.

In some embodiments, the classifier comprises a machine learning engine. In some embodiments, the classifier further comprises an input of a set of genetic variants at one or more loci of the genome. In some embodiments, the set of genetic variants comprises one or more loci of reported tumor markers.

In some embodiments, the method further comprises using the multi-parametric distribution to determine a distribution score. In some embodiments, the distribution score is indicative of a mutation burden of the genetic aberration. In some embodiments, the distribution score comprises values indicating one or more of a number of the DNA fragments with dinucleosomal protection and a number of the DNA fragments with mononucleosomal protection.

In some embodiments, the method further comprises using the multi-parametric distribution to estimate a multimodal density, and using the multimodal density to determine the presence or absence of the genetic aberration. In some embodiments, using the multimodal density comprises generating a discrimination score from the multimodal density, and comparing the discrimination score to a cutoff value to determine the presence or absence of the genetic aberration. In some embodiments, the method further comprises estimating expression of a gene associated with the genetic aberration by calculating a residual density estimate. In some embodiments, the method further comprises estimating copy number of a gene associated with the genetic aberration by calculating a residual density in mononucleosomes.

In another aspect, disclosed herein is a computer-implemented classifier for determining genetic aberrations in a test subject using deoxyribonucleic acid (DNA) fragments from cell-free DNA obtained from the test subject, comprising: (a) an input of a set of distribution scores for each of one or more populations of cell-free DNA obtained from each of a plurality of subjects, wherein each distribution score is generated based at least on one or more of: (i) a length of the DNA fragments that align with each of a plurality of base positions in a genome, (ii) a number of the DNA fragments that align with each of a plurality of base positions in a genome, and (iii) a number of the DNA fragments that start or end at each of a plurality of base positions in a genome; and (b) an output of classifications of one or more genetic aberrations in the test subject.

In some embodiments, the classifier further comprises a machine learning engine. In some embodiments, the classifier further comprises an input of a set of genetic variants at one or more loci of the genome. In some embodiments, the set of genetic variants comprises one or more loci of reported tumor markers.

In another aspect, disclosed herein is a computer-implemented method for determining genetic aberrations in a test subject using deoxyribonucleic acid (DNA) fragments from cell-free DNA obtained from the test subject, the method comprising: (a) providing a computer-implemented classifier configured to determine genetic aberrations in a test subject using DNA fragments from cell-free DNA obtained from the test subject, the classifier trained using a training set; (b) providing as inputs into the classifier a set of distribution scores for the test subject, wherein each distribution score is indicative of one or more of: (i) a length of the DNA fragments that align with each of a plurality of base positions in a genome, (ii) a number of the DNA fragments that align with each of a plurality of base positions in a genome, and (iii) a number of the DNA fragments that start or end at each of a plurality of base positions in a genome; and (c) using the classifier to generate, by a computer, a classification of genetic aberrations in the test subject.

In some embodiments, the method further comprises performing prior to (a): (i) providing a training set comprising: (1) a set of reference distribution scores for each of one or more populations of cell-free DNA from each of a plurality of control subjects, wherein each reference distribution score is indicative of one or more of: (i) a length of the DNA fragments that align with each of a plurality of base positions in a genome, (ii) a number of the DNA fragments that align with each of a plurality of base positions in a genome, and (iii) a number of the DNA fragments that start or end at each of a plurality of base positions in a genome; (2) a set of phenotypic distribution scores for each of one or more populations of cell-free DNA from each of a plurality of subjects having an observed phenotype, wherein each phenotypic distribution score is indicative of one or more of: (i) a length of the DNA fragments that align with each of a plurality of base positions in a genome, (ii) a number of the DNA fragments that align with each of a plurality of base positions in a genome, and (iii) a number of the DNA fragments that start or end at each of a plurality of base positions in a genome; (3) a set of reference classifications for each of the populations of cell-free DNA obtained from control subjects; (4) a set of phenotypic classifications for each of the populations of cell-free DNA obtained from subjects having observed phenotypes; and (ii) training, by a computer, the classifier using the training set.

In some embodiments, the control subjects comprise asymptomatic healthy individuals. In some embodiments, the subjects having an observed phenotype comprise (a) subjects with a tissue-specific cancer, (b) subjects with a particular stage of cancer, (c) subjects with an inflammatory condition, (d) subjects that are asymptomatic to cancer but have a tumor that will progress into cancer, or (e) subjects with cancer having positive or negative response to a therapy.

In another aspect, disclosed herein is a computer-implemented method for analyzing cell-free deoxyribonucleic acid (DNA) fragments derived from a subject, the method comprising: obtaining sequence information representative of the cell-free DNA fragments; and performing a multi-parametric analysis on a plurality of data sets using the sequence information to generate a multi-parametric model representative of the cell-free DNA fragments, wherein the multi-parametric model comprises three or more dimensions.

In some embodiments, the data sets are selected from the group consisting of: (a) start position of DNA fragments sequenced, (b) end position of sequenced DNA fragments, (c) number of unique sequenced DNA fragments that cover a mappable position, (d) length of sequenced DNA fragments, (e) a likelihood that a mappable base-pair position will appear at a terminus of a sequenced DNA fragment, (f) a likelihood that a mappable base-pair position will appear within a sequenced DNA fragment as a consequence of differential nucleosome occupancy, (g) a sequence motif of sequenced DNA fragments, (h) GC content, (i) sequenced DNA fragment length distribution, and (j) methylation status. In some embodiments, the sequence motif is a sequence of 2-8 base pairs long located at a terminus of a DNA fragment. In some embodiments, the multi-parametric analysis comprises mapping to each of a plurality of base positions or regions of a genome, one or more distributions selected from the group consisting of: (i) a distribution of the number of unique cell-free DNA fragments containing a sequence that covers the mappable position in the genome, (ii) a distribution of the fragment lengths for each of at least some of the cell-free DNA fragments such that the DNA fragment contains a sequence that covers the mappable position in the genome, and (iii) a distribution of the likelihoods that a mappable base-pair position will appear at a terminus of a sequenced DNA fragment. In some embodiments, the plurality of base positions or regions of a genome include at least one base position or region associated with one or more of the genes listed in Table 1. In some embodiments, each of the plurality of base positions or regions of a genome is between 2 and 500 base pairs in length. In some embodiments, the plurality of base positions or regions of a genome is identified by: (i) providing one or more genome partitioning maps, and (ii) selecting from the genome partitioning maps the plurality of base positions or regions of a genome, each base position or region of a genome mapping to a gene of interest. In some embodiments, the mapping comprises mapping a plurality of values from each of a plurality of the data sets, to each of a plurality of base positions or regions of a genome. In some embodiments, at least one of the plurality of values is a data set selected from the group consisting of (a) start position of DNA fragments sequenced, (b) end position of sequenced DNA fragments, (c) number of unique sequenced DNA fragments that cover a mappable position, (d) length of sequenced DNA fragments, (e) a likelihood that a mappable base-pair position will appear at a terminus of a sequenced DNA fragment, (f) a likelihood that a mappable base-pair position will appear within a sequenced DNA fragment as a consequence of differential nucleosome occupancy, or (g) a sequence motif of sequenced DNA fragments.

In some embodiments, the multi-parametric analysis comprises applying, by a computer, one or more mathematical transforms to generate the multi-parametric model. In some embodiments, the mathematical transforms comprise a watershed transformation. In some embodiments, the multi-parametric model is a joint distribution model of a plurality of variables selected from the group consisting of: (a) start position of DNA fragments sequenced, (b) end position of sequenced DNA fragments, (c) number of unique sequenced DNA fragments that cover a mappable position, (d) length of sequenced DNA fragments, (e) a likelihood that a mappable base-pair position will appear at a terminus of a sequenced DNA fragment, (f) a likelihood that a mappable base-pair position will appear within a sequenced DNA fragment as a consequence of differential nucleosome occupancy, and (g) a sequence motif of sequenced DNA fragments.

In some embodiments, the method further comprises identifying in the multi-parametric model, one or more peaks, each peak having a peak distribution width and a peak coverage. In some embodiments, the method further comprises incorporating variability induced by germline or somatic single nucleotide polymorphisms present in the subject. In some embodiments, the method further comprises detecting one or more deviations between the multi-parametric model representative of the cell-free DNA fragments and a reference multi-parametric model. In some embodiments, the deviation is selected from the group consisting of: (i) an increase in the number of reads outside a nucleosome region, (ii) an increase in the number of reads within a nucleosome region, (iii) a broader peak distribution relative to a mappable genomic location, (iv) a shift in location of a peak, (v) identification of a new peak, (vi) a change in depth of coverage of a peak, (vii) a change in start position around a peak, and (viii) a change in fragment sizes associated with a peak. In some embodiments, the reference multi-parametric model is derived from a healthy asymptomatic individual. In some embodiments, the reference multi-parametric model is derived from the subject at a different point in time.

In some embodiments, the reference multi-parametric model is derived from DNA acquired from stromal tissue from the surrounding tumor microenvironment of the subject. In some embodiments, the reference multi-parametric model is derived from sheared genomic DNA from a healthy asymptomatic individual. In some embodiments, the reference multi-parametric model is derived from a nucleosomal occupancy profile of a given tissue type. In some embodiments, the tissue type is a normal tissue selected from the group consisting of: breast, colon, lung, pancreas, prostate, ovary, skin, and liver. In some embodiments, the reference multi-parametric model is derived from a cohort of individuals having a shared characteristic. In some embodiments, the shared characteristic is selected from the group consisting of: a tumor type, an inflammatory condition, an apoptotic condition, a necrotic condition, a tumor recurrence, and resistance to a treatment. In some embodiments, the apoptotic condition is selected from the group consisting of: an infection and cellular turnover. In some embodiments, the necrotic condition is selected from the group consisting of: a cardiovascular condition, sepsis, and gangrene.

In some embodiments, the method further comprises determining a contribution of the multi-parametric model attributed to apoptotic processes in cells from which the cell-free DNA originated. In some embodiments, the method further comprises determining a contribution of the multi-parametric model attributed to necrotic processes in cells from which the cell-free DNA originated. In some embodiments, the method further comprises performing one or more of the following assays on a bodily sample from the subject: (i) tissue of origin analysis, (ii) gene expression analysis, (iii) transcription factor binding site (TFBS) occupancy analysis, (iv) methylation status analysis, (v) somatic mutation detection, (vi) measurement of level of detectable somatic mutations, (vii) germline mutation detection, and (viii) measurement of level of detectable germline mutations.

In some embodiments, the method further comprises performing a multi-parametric analysis to measure RNA expression of the cell-free DNA fragments. In some embodiments, the method further comprises performing a multi-parametric analysis to measure reverse methylation of the cell-free DNA fragments. In some embodiments, the method further comprises performing a multi-parametric analysis to measure a reverse nucleosomal mapping of the cell-free DNA fragments. In some embodiments, the method further comprises performing a multi-parametric analysis to identify the presence of one or more somatic single nucleotide polymorphisms in the cell-free DNA fragments. In some embodiments, the method further comprises performing a multi-parametric analysis to identify the presence of one or more germline single nucleotide polymorphisms in the cell-free DNA fragments. In some embodiments, the method further comprises generating a distribution score comprising values indicating a number of the DNA fragments with dinucleosomal protection and/or a number of the DNA fragments with mononucleosomal protection. In some embodiments, the method further comprises estimating a mutation burden of the subject. In some embodiments, the method further comprises estimating a multimodal density, and using the multimodal density to identify the presence of one or more genetic aberrations in the cell-free DNA fragments. In some embodiments, the method further comprises mapping a canonical nucleosomal architecture. In some embodiments, the mapping comprises performing topographic modeling of bivariate normal mixtures.

In another aspect, disclosed herein is a computer-implemented method for analyzing cell-free deoxyribonucleic acid (DNA) fragments derived from a subject, the method comprising: obtaining a multi-parametric model representative of the cell-free DNA fragments; and performing, with the computer, statistical analysis to classify the multi-parametric model as being associated with one or more nucleosomal occupancy profiles representing distinct cohorts.

In some embodiments, the statistical analysis comprises providing one or more genome partitioning maps listing relevant genomic intervals representative of genes of interest for further analysis. In some embodiments, the statistical analysis further comprises selecting a set of one or more localized genomic regions based on the genome partitioning maps. In some embodiments, the statistical analysis further comprises analyzing one or more localized genomic regions in the set to obtain a set of one or more nucleosomal map disruptions. In some embodiments, the statistical analysis comprises one or more of: pattern recognition, deep learning, and unsupervised learning. In some embodiments, the genome partitioning maps are constructed by: (a) providing populations of cell-free DNA from two or more subjects in a cohort; (b) performing a multi-parametric analysis of each of the populations of cell-free DNA to generate a multi-parametric model for each of the samples; and (c) analyzing the multi-parametric models to identify one or more localized genomic regions. In some embodiments, [0025], wherein at least one of the nucleosomal map disruptions is associated with a driver mutation, wherein the driver mutation is chosen from the group consisting of: a somatic variant, a germline variant, and a DNA methylation. In some embodiments, at least one of the nucleosomal map disruptions is used to classify the multi-parametric model as being associated with one or more nucleosomal occupancy profiles representing distinct cohorts.

In some embodiments, at least one of the localized genomic regions is a short region of DNA ranging from about 2 to about 200 base pairs, wherein the region contains a pattern of significant structural variation. In some embodiments, at least one of the localized genomic regions is a short region of DNA ranging from about 2 to about 200 base pairs, wherein the region contains a cluster of significant structural variation. In some embodiments, the structural variation is a variation in nucleosomal positioning selected from the group consisting of: an insertion, a deletion, a translocation, a gene rearrangement, methylation status, a micro-satellite, a copy number variation, a copy number-related structural variation, or any other variation which indicates differentiation. In some embodiments, the cluster is a hotspot region within a localized genomic region, wherein the hotspot region contains one or more significant fluctuations or peaks. In some embodiments, at least one of the localized genomic regions is a short region of DNA ranging from about 2 to about 200 base pairs, wherein the region contains a pattern of significant instability. In some embodiments, the analyzing one or more localized genomic regions comprises detecting one or more deviations between the multi-parametric model representative of the cell-free DNA fragments and one or more reference multi-parametric models selected from: (i) one or more healthy reference multi-parametric models associated with one or more cohorts of healthy controls, and (ii) one or more diseased reference multi-parametric models associated with one or more cohorts of diseased subjects.

In some embodiments, the method further comprises selection of a set of structural variations, wherein the selection of a structural variation is a function of one or more of: (i) one or more healthy reference multi-parametric models; (ii) efficiency of one or more probes targeting the structural variation; and (iii) prior information regarding portions of the genome where an expected frequency of structural variations is higher than the average expected frequency of structural variations across the genome.

In some embodiments, at least one of the nucleosomal occupancy profiles is associated with one or more assessments selected from the group consisting of: tumor indication, early detection of cancer, tumor type, tumor severity, tumor aggressiveness, tumor resistance to treatment, tumor clonality, tumor druggability, tumor progression, and plasma dysregulation score. In some embodiments, an assessment of tumor clonality is determined from observing heterogeneity in nucleosomal map disruption across cell-free DNA fragments in a sample. In some embodiments, an assessment of relative contributions of each of two or more clones is determined.

In some embodiments, the method further comprises determining a disease score of a disease, wherein the disease score is determined as a function of one or more of: (i) one or more nucleosomal occupancy profiles associated with the disease; (ii) one or more healthy reference multi-parametric models associated with a cohort not having the disease; and (iii) one or more diseased reference multi-parametric models associated with a cohort having the disease.

In another aspect, disclosed herein is a computer-implemented method for creating a trained classifier, comprising: (a) providing a plurality of different classes, wherein each class represents a set of subjects with a shared characteristic; (b) for each of a plurality of populations of cell-free DNA obtained from each of the classes, providing a multi-parametric model representative of cell-free deoxyribonucleic acid (DNA) fragments from the populations of cell-free DNA, thereby providing a training data set; and (c) training, by a computer, a learning algorithm on the training data set to create one or more trained classifiers, wherein each trained classifier is configured to classify a test population of cell-free DNA from a test subject into one or more of the plurality of different classes.

In some embodiments, the learning algorithm is selected from the group consisting of: a random forest, a neural network, a support vector machine, and a linear classifier. In some embodiments, each of the plurality of different classes is selected from the group consisting of: healthy, breast cancer, colon cancer, lung cancer, pancreatic cancer, prostate cancer, ovarian cancer, melanoma, and liver cancer.

In an aspect, disclosed herein is a method of classifying a test sample from a subject, comprising: (a) providing a multi-parametric model representative of cell-free deoxyribonucleic acid (DNA) fragments from a test population of cell-free DNA from the subject; and (b) classifying the test population of cell-free DNA using a trained classifier.

In some embodiments, the method further comprises performing a therapeutic intervention on the subject based on the classification of the population of cell-free DNA.

In another aspect, disclosed herein is a computer-implemented method comprising: (a) generating, by a computer, sequence information from cell-free DNA fragments from a subject; (b) mapping, by a computer, the cell-free DNA fragments to a reference genome based on the sequence information; and (c) analyzing, by a computer, the mapped cell-free DNA fragments to determine, at each of a plurality of base positions in the reference genome, a plurality of measures selected from the group consisting of: (i) number of cell-free DNA fragments mapping to the base position, (ii) length of each cell-free DNA fragment mapping to the base position, (iii) number of cell-free DNA fragments mapping to the base position as a function of length of the cell-free DNA fragment; (iv) number of cell-free DNA fragments starting at the base position; (v) number of cell-free DNA fragments ending at the base position; (vi) number of cell-free DNA fragments starting at the base position as a function of length, and (vii) number of cell-free DNA fragments ending at the base position as a function of length. In some embodiments, the sequence information is a full or partial sequence of the cell-free DNA fragment.

In another aspect, disclosed herein is a computer-implemented method of analyzing cell-free DNA fragments derived from a subject, the method comprising: (a) receiving, by a computer, sequence information representative of the cell-free DNA fragments, and (b) performing an analysis per mappable base position or genome position, comprising a plurality of: (i) the number of sequence fragments that start or end at the base position or genome position, (ii) sequence or fragment lengths at the base position or genome position, (iii) fragment or sequence coverage at the base position or genome position, and (iv) sequence motif distribution at the base position or genome position.

In some embodiments, the method further comprises detecting a deviation between the cell-free DNA from the subject and one or more reference populations of cell-free DNA, wherein the deviation is indicative of the presence of a condition or property in the subject. In some embodiments, the analysis comprises one or more in the group consisting of: (i) tissue of origin analysis, (ii) gene expression analysis, (iii) transcription factor binding site (TFBS) occupancy analysis, (iv) methylation status analysis, (v) somatic mutation detection, (vi) measurement of level of detectable somatic mutations, (vii) germline mutation detection, and (viii) measurement of level of detectable germline mutations.

In some embodiments, the condition or property is one or more in the group consisting of: (i) presence of cancer, (ii) presence of a tissue abnormality, (iii) presence of a particular tissue-specific abnormality, (iv) presence of a variation in epigenetic regulation or function, and (v) presence of a variation in epigenetic regulation or function. In some embodiments, the analysis further comprises detection of one or more in the group consisting of: (i) single-nucleotide variants, (ii) copy number variants, (iii) insertions, (iv) deletions, (v) gene rearrangements, (vi) methylation status, and (vii) loss of heterozygosity.

In another aspect, disclosed herein is a method of generating a classifier for determining a likelihood that a subject belongs to one or more classes of clinical significance, the method comprising: a) providing a training set comprising, for each of the one or more classes of clinical significance, populations of cell-free DNA from each of a plurality of subjects of a species belonging to the class of clinical significance and from each of a plurality of subjects of the species not belonging to the class of clinical significance; b) sequencing cell-free DNA fragments from the populations of cell-free DNA to produce a plurality of DNA sequences; c) for each population of cell-free DNA, mapping the plurality of DNA sequences to each of one or more genomic regions in a reference genome of the species, each genomic region comprising a plurality of genetic loci; d) preparing, for each population of cell-free DNA, a dataset comprising, for each of a plurality of the genetic loci, values indicating a quantitative measure of at least one characteristic selected from: (i) DNA sequences mapping to the genetic locus, (ii) DNA sequences starting at the locus, and (iii) DNA sequences ending at the genetic locus, to yield a training set; and e) training a computer-based machine learning system on the training set, thereby generating a classifier for determining a likelihood that the subject belongs to one or more classes of clinical significance.

In some embodiments, the class of clinical significance indicates a presence or absence of one or more genetic variants. In some embodiments, the class of clinical significance indicates a presence or absence of one or more cancers. In some embodiments, the class of clinical significance indicates a presence or absence of one or more non-cancer disease, disorder, or abnormal biological state. In some embodiments, the class of clinical significance indicates a presence or absence of one or more canonical driver mutations. In some embodiments, the class of clinical significance indicates a presence or absence of one or more cancer subtypes. In some embodiments, the class of clinical significance indicates a likelihood of response to a treatment for cancer. In some embodiments, the class of clinical significance indicates a presence or absence of a copy number variation (CNV). In some embodiments, the class of clinical significance indicates tissue of origin. In some embodiments, the quantitative measure comprises a size distribution of DNA sequences having the selected characteristics.

In another aspect, disclosed herein is a method of determining an abnormal biological state in a subject, the method comprising: a) sequencing cell-free DNA fragments from cell-free DNA from the subject to produce DNA sequences; b) mapping the DNA sequences to each of one or more genomic regions in a reference genome of a species of the subject, each genomic region comprising a plurality of genetic loci; c) preparing a dataset comprising, for each of a plurality of the genetic loci, values indicating a quantitative measure of at least one feature selected from: (i) DNA sequences mapping to the genetic locus, (ii) DNA sequences starting at the locus, and (iii) DNA sequences ending at the genetic locus; and d) based on the dataset, determining a likelihood of the abnormal biological state.

In some embodiments, the reference genome comprises a reference genome of a human. In some embodiments, the quantitative measure comprises a size distribution of DNA sequences having the selected features. In some embodiments, the size distribution comprises values indicating a number of DNA fragments with dinucleosomal protection and/or DNA fragments with mononucleosomal protection. In some embodiments, the quantitative measure further comprises a ratio of size distribution of DNA sequences having the selected features. In some embodiments, the dataset further comprises values indicating, for a plurality of the genetic loci, location in an intron or exon. In some embodiments, the quantitative measure is a normalized measure. In some embodiments, determining the abnormal state comprises determining a degree of abnormality. In some embodiments, the method further comprises administering a therapeutic intervention to treat the abnormal biological state.

In another aspect, disclosed herein is a computer-implemented method for generating an output indicative of a presence or absence of a genetic aberration in deoxyribonucleic acid (DNA) fragments from cell-free DNA obtained from a subject, the method comprising: (a) constructing, by a computer, a distribution of the DNA fragments from the cell-free DNA over a plurality of base positions in a genome; and (b) for each of one or more genetic loci, calculating, by a computer, a quantitative measure indicative of a ratio of (1) a number of the DNA fragments with dinucleosomal protection associated with a genetic locus from the one or more genetic loci, and (2) a number of the DNA fragments with mononucleosomal protection associated with the genetic locus, or vice versa; and (c) determining, using the quantitative measure for each of the one or more genetic loci, said output indicative of a presence or absence of the genetic aberration in the one or more genetic loci in the subject. In some embodiments, the distribution comprises one or more multi-parametric distributions.

In another aspect, disclosed herein is a computer-implemented method for generating an output indicative of a presence or absence of a genetic aberration in deoxyribonucleic acid (DNA) fragments from cell-free DNA obtained from a subject, the method comprising: (a) constructing, by a computer, a distribution of the DNA fragments from the cell-free DNA over a plurality of base positions in a genome; and (b) using the distribution to determine said output indicative of a presence or absence of the genetic aberration in the subject, wherein the presence or absence is determined (i) without comparing the distribution of the DNA fragments to a reference distribution from a source external to a genome of the subject, (ii) without comparing parameters derived from the distribution of the DNA fragments to reference parameters, and (iii) without comparing the distribution of the DNA fragments to a reference distribution from a control of the subject.

In some embodiments, the genetic aberration comprises a copy number variation (CNV). In some embodiments, the genetic aberration comprises a single nucleotide variant (SNV). In some embodiments, the distribution comprises one or more multi-parametric distributions.

In another aspect, disclosed herein is a computer-implemented method for deconvolving a distribution of deoxyribonucleic acid (DNA) fragments from cell-free DNA obtained from a subject, the method comprising: (a) constructing, by a computer, a distribution of a coverage of the DNA fragments from the cell-free DNA over a plurality of base positions in a genome; and (b) for each of one or more genetic loci, deconvolving, by a computer, the distribution of the coverage, thereby generating fractional contributions associated with one or more members selected from the group consisting of a copy number (CN) component, a cell clearance component, and a gene expression component.

In some embodiments, calculating comprises calculating fractional contributions of the distribution of the DNA fragment coverage associated with two or more members selected from the group consisting of the copy number (CN) component, the cell clearance component, and the gene expression component. In some embodiments, calculating comprises calculating fractional contributions of the distribution of the DNA fragment coverage associated with the copy number component, the clearance component, and the expression component.

In some embodiments, the method further comprises generating an output indicative of a presence or absence of a genetic aberration based at least on a portion of the fractional contributions. In some embodiments, the distribution comprises one or more multi-parametric distributions.

In another aspect, disclosed herein is a computer-implemented method for generating an output indicative of a presence or absence of a genetic aberration in deoxyribonucleic acid (DNA) fragments from cell-free DNA obtained from a subject, the method comprising: (a) constructing, by a computer, a distribution of the DNA fragments from the cell-free DNA over a plurality of base positions in a genome; (b) identifying, by a computer, one or more peaks at one or more base positions of the plurality of base positions in the distribution of the DNA fragments, wherein each peak comprises a peak value and a peak distribution width; and (c) determining, by a computer, based at least on (i) the one or more base positions, (ii) the peak value, and (iii) the peak distribution width, the presence or absence of the genetic aberration in the subject.

In some embodiments, the one or more peaks comprises a dinucleosomal peak or a mononucleosomal peak. In some embodiments, the one or more peaks comprises a dinucleosomal peak and a mononucleosomal peak. In some embodiments, said output indicative of a presence or absence of the genetic aberration is determined based at least on a quantitative measure indicative of a ratio of a first peak value associated with the dinucleosomal peak and a second peak value associated with the mononucleosomal peak, or vice versa. In some embodiments, the distribution comprises one or more multi-parametric distributions.

In another aspect, disclosed herein is a computer-implemented method for generating an output indicative of a presence or absence of a genetic aberration in deoxyribonucleic acid (DNA) fragments from cell-free DNA obtained from a subject, the method comprising: (a) constructing, by a computer, a distribution of the DNA fragments from the cell-free DNA over a plurality of base positions in a genome; (b) analyzing, by a computer, the distribution of the DNA fragments at one or more genetic loci, which analyzing comprises detecting deviations between the distribution of the DNA fragments and a plurality of reference distributions selected from: (i) one or more healthy reference distributions associated with one or more cohorts of healthy controls, and (ii) one or more diseased reference distributions associated with one or more cohorts of diseased subjects; and (c) determining, by a computer, based at least on the deviations detected in (b), said output indicative of a presence or absence of the genetic aberration in the subject.

In some embodiments, the distribution comprises one or more multi-parametric distributions. In some embodiments, analyzing comprises calculating one or more delta signals, each delta signal comprising a difference between the distribution of the DNA fragments and a reference distribution of the plurality of reference distributions.

In another aspect, disclosed herein is a method for processing a biological sample of a subject, comprising: (a) obtaining said biological sample of said subject, wherein said biological sample comprises deoxyribonucleic acid (DNA) fragments; (b) assaying said biological sample to generate a signal(s) indicative of a presence or absence of DNA fragments with (i) dinucleosomal protection associated with a genetic locus from one or more genetic loci, and (ii) mononucleosomal protection associated with the genetic locus; and (c) using said signal(s) to generate an output indicative of said presence or absence of DNA fragments with (i) dinucleosomal protection associated with a genetic locus from one or more genetic loci, and (ii) mononucleosomal protection associated with the genetic locus.

In some embodiments, assaying comprises enriching said biological sample for DNA fragments for a set of one or more genetic loci. In some embodiments, assaying comprises sequencing said DNA fragments of said biological sample.

In another aspect, disclosed herein is a method for analyzing a biological sample that comprises cell-free DNA fragments derived from a subject, wherein the method comprises detecting DNA fragments from the same genetic locus which correspond to each of mononucleosomal protection and dinucleosomal protection.

In another aspect, disclosed herein is a computer-implemented method for determining a presence or absence of a genetic aberration in deoxyribonucleic acid (DNA) fragments from cell-free DNA obtained from a subject, the method comprising: (a) constructing, by a computer, a multi-parametric distribution of the DNA fragments over a plurality of base positions in a genome; and (b) without taking into account a base identity of each base position in a first locus, using the multi-parametric distribution to determine the presence or absence of the genetic aberration in the first locus in the subject.

In some embodiments, the genetic aberration comprises a sequence aberration or a copy number variation (CNV), wherein the sequence aberration is selected from the group consisting of: (i) a single nucleotide variant (SNV), (ii) an insertion or deletion (indel), and (iii) a gene fusion. In some embodiments, the multi-parametric distribution comprises parameters indicative of one or more of: (i) a length of the DNA fragments that align with each of the plurality of base positions in the genome, (ii) a number of the DNA fragments that align with each of the plurality of base positions in the genome, and (iii) a number of the DNA fragments that start or end at each of the plurality of base positions in the genome. In some embodiments, the method further comprises using the multi-parametric distribution to determine a distribution score, wherein the distribution score is indicative of a mutation burden of the genetic aberration In some embodiments, the distribution score comprises values indicating one or more of a number of the DNA fragments with dinucleosomal protection and a number of the DNA fragments with mononucleosomal protection.

In another aspect, disclosed herein is a computer-implemented classifier for determining genetic aberrations in a test subject using deoxyribonucleic acid (DNA) fragments from cell-free DNA obtained from the test subject, comprising: (a) an input of a set of distribution scores for each of one or more populations of cell-free DNA obtained from each of a plurality of subjects, wherein each distribution score is generated based at least on one or more of: (i) a length of the DNA fragments that align with each of a plurality of base positions in a genome, (ii) a number of the DNA fragments that align with each of a plurality of base positions in a genome, and (iii) a number of the DNA fragments that start or end at each of a plurality of base positions in a genome; and (b) an output of classifications of one or more genetic aberrations in the test subject.

In another aspect, disclosed herein is a computer-implemented method for determining genetic aberrations in a test subject using deoxyribonucleic acid (DNA) fragments from cell-free DNA obtained from the test subject, the method comprising: (a) providing a computer-implemented classifier configured to determine genetic aberrations in a test subject using DNA fragments from cell-free DNA obtained from the test subject, the classifier trained using a training set; (b) providing as inputs into the classifier a set of distribution scores for the test subject, wherein each distribution score is indicative of one or more of: (i) a length of the DNA fragments that align with each of a plurality of base positions in a genome, (ii) a number of the DNA fragments that align with each of a plurality of base positions in a genome, and (iii) a number of the DNA fragments that start or end at each of a plurality of base positions in a genome; and (c) using the classifier to generate, by a computer, a classification of genetic aberrations in the test subject.

In another aspect, disclosed herein is a computer-implemented method for analyzing cell-free deoxyribonucleic acid (DNA) fragments derived from a subject, the method comprising: obtaining sequence information representative of the cell-free DNA fragments; and performing a multi-parametric analysis on a plurality of data sets using the sequence information to generate a multi-parametric model representative of the cell-free DNA fragments, wherein the multi-parametric model comprises three or more dimensions.

In some embodiments, the data sets are selected from the group consisting of: (a) start position of DNA fragments sequenced, (b) end position of sequenced DNA fragments, (c) number of unique sequenced DNA fragments that cover a mappable position, (d) length of sequenced DNA fragments, (e) a likelihood that a mappable base-pair position will appear at a terminus of a sequenced DNA fragment, (f) a likelihood that a mappable base-pair position will appear within a sequenced DNA fragment as a consequence of differential nucleosome occupancy, (g) a sequence motif of sequenced DNA fragments, (h) GC content, (i) sequenced DNA fragment length distribution, and (j) methylation status. In some embodiments, the multi-parametric analysis comprises mapping to each of a plurality of base positions or regions of a genome, one or more distributions selected from the group consisting of: (i) a distribution of the number of unique cell-free DNA fragments containing a sequence that covers the mappable position in the genome, (ii) a distribution of the fragment lengths for each of at least some of the cell-free DNA fragments such that the DNA fragment contains a sequence that covers the mappable position in the genome, and (iii) a distribution of the likelihoods that a mappable base-pair position will appear at a terminus of a sequenced DNA fragment. In some embodiments, the plurality of base positions or regions of a genome include at least one base position or region associated with one or more of the genes listed in Table 1. In some embodiments, the mapping comprises mapping a plurality of values from each of a plurality of the data sets, to each of a plurality of base positions or regions of a genome. In some embodiments, at least one of the plurality of values is a data set selected from the group consisting of (a) start position of DNA fragments sequenced, (b) end position of sequenced DNA fragments, (c) number of unique sequenced DNA fragments that cover a mappable position, (d) length of sequenced DNA fragments, (e) a likelihood that a mappable base-pair position will appear at a terminus of a sequenced DNA fragment, (f) a likelihood that a mappable base-pair position will appear within a sequenced DNA fragment as a consequence of differential nucleosome occupancy, or (g) a sequence motif of sequenced DNA fragments. In some embodiments, the multi-parametric analysis comprises applying, by a computer, one or more mathematical transforms to generate the multi-parametric model. In some embodiments, the multi-parametric model is a joint distribution model of a plurality of variables selected from the group consisting of: (a) start position of DNA fragments sequenced, (b) end position of sequenced DNA fragments, (c) number of unique sequenced DNA fragments that cover a mappable position, (d) length of sequenced DNA fragments, (e) a likelihood that a mappable base-pair position will appear at a terminus of a sequenced DNA fragment, (f) a likelihood that a mappable base-pair position will appear within a sequenced DNA fragment as a consequence of differential nucleosome occupancy, and (g) a sequence motif of sequenced DNA fragments.

In some embodiments, the method further comprises identifying in the multi-parametric model, one or more peaks, each peak having a peak distribution width and a peak coverage. In some embodiments, the method further comprises detecting one or more deviations between the multi-parametric model representative of the cell-free DNA fragments and a reference multi-parametric model. In some embodiments, the deviation is selected from the group consisting of: (i) an increase in the number of reads outside a nucleosome region, (ii) an increase in the number of reads within a nucleosome region, (iii) a broader peak distribution relative to a mappable genomic location, (iv) a shift in location of a peak, (v) identification of a new peak, (vi) a change in depth of coverage of a peak, (vii) a change in start position around a peak, and (viii) a change in fragment sizes associated with a peak.

In some embodiments, the method further comprises determining a contribution of the multi-parametric model attributed to (i) apoptotic processes in cells from which the cell-free DNA originated or (ii) necrotic processes in cells from which the cell-free DNA originated. In some embodiments, the method further comprises performing a multi-parametric analysis to (i) measure RNA expression of the cell-free DNA fragments, (ii) measure methylation of the cell-free DNA fragments, (iii) measure a nucleosomal mapping of the cell-free DNA fragments, or (iv) identify the presence of one or more somatic single nucleotide polymorphisms in the cell-free DNA fragments or one or more germline single nucleotide polymorphisms in the cell-free DNA fragments. In some embodiments, the method further comprises generating a distribution score comprising values indicating a number of the DNA fragments with dinucleosomal protection or a number of the DNA fragments with mononucleosomal protection. In some embodiments, the method further comprises estimating a mutation burden of the subject.

In another aspect, disclosed herein is a computer-implemented method for analyzing cell-free deoxyribonucleic acid (DNA) fragments derived from a subject, the method comprising: obtaining a multi-parametric model representative of the cell-free DNA fragments; and performing, with the computer, statistical analysis to classify the multi-parametric model as being associated with one or more nucleosomal occupancy profiles representing distinct cohorts.

In another aspect, disclosed herein is a computer-implemented method for creating a trained classifier, comprising: (a) providing a plurality of different classes, wherein each class represents a set of subjects with a shared characteristic; (b) for each of a plurality of populations of cell-free DNA obtained from each of the classes, providing a multi-parametric model representative of cell-free deoxyribonucleic acid (DNA) fragments from the populations of cell-free DNA, thereby providing a training data set; and (c) training, by a computer, a learning algorithm on the training data set to create one or more trained classifiers, wherein each trained classifier is configured to classify a test population of cell-free DNA from a test subject into one or more of the plurality of different classes.

In another aspect, disclosed herein is a method of classifying a test sample from a subject, comprising: (a) providing a multi-parametric model representative of cell-free deoxyribonucleic acid (DNA) fragments from a test population of cell-free DNA from the subject; and (b) classifying the test population of cell-free DNA using a trained classifier.

In another aspect, disclosed herein is a computer-implemented method comprising: (a) generating, by a computer, sequence information from cell-free DNA fragments from a subject; (b) mapping, by a computer, the cell-free DNA fragments to a reference genome based on the sequence information; and (c) analyzing, by a computer, the mapped cell-free DNA fragments to determine, at each of a plurality of base positions in the reference genome, a plurality of measures selected from the group consisting of: (i) number of cell-free DNA fragments mapping to the base position, (ii) length of each cell-free DNA fragment mapping to the base position, (iii) number of cell-free DNA fragments mapping to the base position as a function of length of the cell-free DNA fragment; (iv) number of cell-free DNA fragments starting at the base position; (v) number of cell-free DNA fragments ending at the base position; (vi) number of cell-free DNA fragments starting at the base position as a function of length, and (vii) number of cell-free DNA fragments ending at the base position as a function of length.

In another aspect, disclosed herein is a computer-implemented method of analyzing cell-free DNA fragments derived from a subject, the method comprising: (a) receiving, by a computer, sequence information representative of the cell-free DNA fragments, and (b) performing an analysis per mappable base position or genome position, comprising a plurality of: (i) the number of sequence fragments that start or end at the base position or genome position, (ii) sequence or fragment lengths at the base position or genome position, (iii) fragment or sequence coverage at the base position or genome position, and (iv) sequence motif distribution at the base position or genome position. In another aspect, disclosed herein is a method of generating a classifier for determining a likelihood that a subject belongs to one or more classes of clinical significance, the method comprising: a) providing a training set comprising, for each of the one or more classes of clinical significance, populations of cell-free DNA from each of a plurality of subjects of a species belonging to the class of clinical significance and from each of a plurality of subjects of the species not belonging to the class of clinical significance; b) sequencing cell-free DNA fragments from the populations of cell-free DNA to produce a plurality of DNA sequences; c) for each population of cell-free DNA, mapping the plurality of DNA sequences to each of one or more genomic regions in a reference genome of the species, each genomic region comprising a plurality of genetic loci; d) preparing, for each population of cell-free DNA, a dataset comprising, for each of a plurality of the genetic loci, values indicating a quantitative measure of at least one characteristic selected from: (i) DNA sequences mapping to the genetic locus, (ii) DNA sequences starting at the locus, and (iii) DNA sequences ending at the genetic locus, to yield a training set; and e) training a computer-based machine learning system on the training set, thereby generating a classifier for determining a likelihood that the subject belongs to one or more classes of clinical significance.

In another aspect, disclosed herein is a method of determining an abnormal biological state in a subject, the method comprising: a) sequencing cell-free DNA fragments from cell-free DNA from the subject to produce DNA sequences; b) mapping the DNA sequences to each of one or more genomic regions in a reference genome of a species of the subject, each genomic region comprising a plurality of genetic loci; c) preparing a dataset comprising, for each of a plurality of the genetic loci, values indicating a quantitative measure of at least one feature selected from: (i) DNA sequences mapping to the genetic locus, (ii) DNA sequences starting at the locus, and (iii) DNA sequences ending at the genetic locus; and d) based on the dataset, determining a likelihood of the abnormal biological state.

In another aspect, disclosed herein is a computer-implemented method for generating an output indicative of a presence or absence of a genetic aberration in deoxyribonucleic acid (DNA) fragments from cell-free DNA obtained from a subject, the method comprising: (a) constructing, by a computer, a distribution of the DNA fragments from the cell-free DNA over a plurality of base positions in a genome; and (b) for each of one or more genetic loci, calculating, by a computer, a quantitative measure indicative of a ratio of (1) a number of the DNA fragments with dinucleosomal protection associated with a genetic locus from the one or more genetic loci, and (2) a number of the DNA fragments with mononucleosomal protection associated with the genetic locus, or vice versa; and (c) determining, using the quantitative measure for each of the one or more genetic loci, said output indicative of a presence or absence of the genetic aberration in the one or more genetic loci in the subject.

In another aspect, disclosed herein is a computer-implemented method for generating an output indicative of a presence or absence of a genetic aberration in deoxyribonucleic acid (DNA) fragments from cell-free DNA obtained from a subject, the method comprising: (a) constructing, by a computer, a distribution of the DNA fragments from the cell-free DNA over a plurality of base positions in a genome; and (b) using the distribution to determine said output indicative of a presence or absence of the genetic aberration in the subject, wherein the presence or absence is determined (i) without comparing the distribution of the DNA fragments to a reference distribution from a source external to a genome of the subject, (ii) without comparing parameters derived from the distribution of the DNA fragments to reference parameters, and (iii) without comparing the distribution of the DNA fragments to a reference distribution from a control of the subject. In some embodiments, the genetic aberration comprises a copy number variation (CNV) or a single nucleotide variant (SNV).

In another aspect, disclosed herein is a computer-implemented method for deconvolving a distribution of deoxyribonucleic acid (DNA) fragments from cell-free DNA obtained from a subject, the method comprising: (a) constructing, by a computer, a distribution of a coverage of the DNA fragments from the cell-free DNA over a plurality of base positions in a genome; and (b) for each of one or more genetic loci, deconvolving, by a computer, the distribution of the coverage, thereby generating fractional contributions associated with one or more members selected from the group consisting of a copy number (CN) component, a cell clearance component, and a gene expression component. In some embodiments, the method further comprises comprising generating an output indicative of a presence or absence of a genetic aberration based at least on a portion of the fractional contributions.

In another aspect, disclosed herein is a computer-implemented method for generating an output indicative of a presence or absence of a genetic aberration in deoxyribonucleic acid (DNA) fragments from cell-free DNA obtained from a subject, the method comprising: (a) constructing, by a computer, a distribution of the DNA fragments from the cell-free DNA over a plurality of base positions in a genome; (b) identifying, by a computer, one or more peaks at one or more base positions of the plurality of base positions in the distribution of the DNA fragments, wherein each peak comprises a peak value and a peak distribution width; and (c) determining, by a computer, based at least on (i) the one or more base positions, (ii) the peak value, and (iii) the peak distribution width, the presence or absence of the genetic aberration in the subject.

In some embodiments, the one or more peaks comprises a dinucleosomal peak or a mononucleosomal peak. In some embodiments, said output indicative of a presence or absence of the genetic aberration is determined based at least on a quantitative measure indicative of a ratio of a first peak value associated with the dinucleosomal peak and a second peak value associated with the mononucleosomal peak, or vice versa.

In another aspect, disclosed herein is a computer-implemented method for generating an output indicative of a presence or absence of a genetic aberration in deoxyribonucleic acid (DNA) fragments from cell-free DNA obtained from a subject, the method comprising: (a) constructing, by a computer, a distribution of the DNA fragments from the cell-free DNA over a plurality of base positions in a genome; (b) analyzing, by a computer, the distribution of the DNA fragments at one or more genetic loci, which analyzing comprises detecting deviations between the distribution of the DNA fragments and a plurality of reference distributions selected from: (i) one or more healthy reference distributions associated with one or more cohorts of healthy controls, and (ii) one or more diseased reference distributions associated with one or more cohorts of diseased subjects; and (c) determining, by a computer, based at least on the deviations detected in (b), said output indicative of a presence or absence of the genetic aberration in the subject. In some embodiments, analyzing comprises calculating one or more delta signals, each delta signal comprising a difference between the distribution of the DNA fragments and a reference distribution of the plurality of reference distributions.

In another aspect, disclosed herein is a method for processing a biological sample of a subject, comprising: (a) obtaining said biological sample of said subject, wherein said biological sample comprises deoxyribonucleic acid (DNA) fragments; (b) assaying said biological sample to generate a signal(s) indicative of a presence or absence of DNA fragments with (i) dinucleosomal protection associated with a genetic locus from one or more genetic loci, and (ii) mononucleosomal protection associated with the genetic locus; and (c) using said signal(s) to generate an output indicative of said presence or absence of DNA fragments with (i) dinucleosomal protection associated with a genetic locus from one or more genetic loci, and (ii) mononucleosomal protection associated with the genetic locus. In some embodiments, assaying comprises (i) enriching said biological sample for DNA fragments for a set of one or more genetic loci or (ii) sequencing said DNA fragments of said biological sample.

In another aspect, disclosed herein is a method for analyzing a biological sample comprising cell-free DNA fragments derived from a subject, the method comprising detecting DNA fragments from the same genetic locus which correspond to each of mononucleosomal protection and dinucleosomal protection.

In another aspect, disclosed herein is a method for analyzing a biological sample comprising cell-free DNA fragments derived from a subject, the method comprising detecting DNA fragments with dinucleosomal protection associated with a genetic locus. In some embodiments, the genetic locus comprises ERBB2, TP53, or NF1. In some embodiments, the genetic locus comprises a gene listed in Table 1.

In another aspect, the present disclosure provides a method of generating a classifier for determining a likelihood that a subject belongs to one or more classes of significance, the method comprising: a) providing a training set comprising, for each of the one or more classes of clinical significance, biological samples from each of a plurality of subjects of a species belonging to the class of clinical significance and from each of a plurality of subjects of the species not belonging to the class of clinical significance, b) sequencing cell free deoxyribonucleic acid (cfDNA) molecules from the biological samples to produce a plurality of deoxyribonucleic acid (DNA) sequences; c) for each biological sample, mapping the plurality of DNA sequences to each of one or more genomic regions in a reference genome of the species, each genomic region comprising a plurality of genetic loci; d) preparing, for each sample, a dataset comprising, for each of a plurality of the genetic loci, values indicating a quantitative measure of at least one characteristic selected from: (i) DNA sequences mapping to the genetic locus, (ii) DNA sequences starting at the locus, and (iii) DNA sequences ending at the genetic locus, to yield a training set; and e) training a computer-based machine learning system on the training set, thereby generating a classifier for determining a likelihood that the subject belongs to one or more classes of clinical significance. In an embodiment, the quantitative measure comprises a size distribution of DNA sequences having the selected characteristics.

In another aspect, a method of determining an abnormal biological state in a subject comprises: a) sequencing cfDNA molecules from a biological sample from the subject to produce DNA sequences; b) mapping the DNA sequences to each of one or more genomic regions in a reference genome of a species of the subject, each genomic region comprising a plurality of genetic loci; c) preparing a dataset comprising, for each of a plurality of the genetic loci, values indicating a quantitative measure of at least one feature selected from: (i) DNA sequences mapping to the genetic locus, (ii) DNA sequences starting at the locus, and (iii) DNA sequences ending at the genetic locus; and d) based on the dataset, determining a likelihood of the abnormal biological state. In an embodiment, the method further comprises administering a therapeutic intervention to treat the abnormal biological state. Thus a method for administering a therapeutic intervention to treat an abnormal biological state can comprise determining an abnormal biological state in a subject, as disclosed herein, followed by administering the therapeutic intervention.

In an embodiment, the quantitative measure comprises a size distribution of DNA sequences having the selected features. In an embodiment, the size distribution comprises values indicating a number of fragments with dinucleosomal protection and/or fragments with mononucleosomal protection. In an embodiment, the quantitative measure further comprises a ratio of size distribution of DNA sequences having the selected features. In an embodiment, the dataset further comprises values indicating, for a plurality of the genetic loci, location in an intron or exon.

Another aspect provides a computer-readable medium comprising machine-executable code which, when executed by one or more computer processors, implements a method for outputting a likelihood of an abnormal state class of a dataset based on an input dataset, the method comprising, for each a plurality of the genetic loci, values indicating a quantitative measure of one or more features derived from fragmentome profiling and selected from: (i) DNA sequences mapping to the genetic locus, (ii) DNA sequences starting at the locus, and (iii) DNA sequences ending at the genetic locus.

Another aspect of the present disclosure provides a method comprising administering to a subject with an abnormal biological state, which subject is characterized as having a fragmentome profile indicative of the abnormal biological state, an effective amount of treatment designed to treat the abnormal biological state.

Another aspect of the present disclosure provides a pharmaceutical which is effective for treating an abnormal biological state, for use in a method comprising administering the pharmaceutical to a subject with the abnormal biological state or suspected of having the abnormal biological state, which subject is characterized as having a fragmentome profile indicative of the abnormal biological state.

The disclosure also provides a pharmaceutical which is effective for treating an abnormal biological state, for use in the manufacture of a medicament for treating a subject with the abnormal biological state or suspected of having the abnormal biological state, which subject is characterized as having a fragmentome profile indicative of the abnormal biological state.

In another aspect, provided herein is a method comprising: providing training data from a plurality of training subjects (e.g., at least 50 training subjects), including a plurality subjects from a first class and a plurality of subjects from a second class, and wherein the training data includes, from a training sample from each training subject, a multi-parametric distribution of cfDNA molecules mapping to one or more selected genomic loci; and training a machine learning algorithm to develop a classification model that, based on test data from a test sample from a test subject, including the multi-parametric distribution of cfDNA molecules mapping to the selected genomic loci, classifies the subject as having cancer or not having cancer. In some embodiments, the classification model is a probabilistic model.

In some embodiments, the first and second classes are selected from: having a cancer and not having the cancer, responding to a therapy and not responding to a therapy and a first stage of cancer and a second stage of cancer. In some embodiments, the multi-parametric distribution includes molecule size, molecule start position and/or molecule end position. In some embodiments, the selected genomic loci include at least a di-nucleosome distance across each of a plurality of oncogenes, e.g., genes of interest from Table 1.

In another aspect provided herein is a method comprising: providing test data from a test sample from a test subject, including a multi-parametric distribution of cfDNA molecules mapping to one or more selected genomic loci; and using a computer-based classification model based on training data from a plurality of training subjects, including a plurality subjects from a first class and a plurality of subjects from a second class, and wherein the training data includes, from a training sample from each training subject, a multi-parametric distribution of cfDNA molecules mapping to one or more selected genomic loci, classifying the test subject as belonging to the first class or the second class. In some embodiments, the classification model is selected to have a positive predictive value of at least 90%, at least 95%, at least 98%, at least 99% or at least 99.8%.

In another aspect provided herein is a method comprising: classifying a subject as having cancer using a classification method as described herein and administering a therapeutic treatment to the subject so classified. In another aspect provided herein is a method comprising: administering to a subject classified as having cancer by a method as described herein, a therapeutic treatment to treat the cancer.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

FIG. 1A illustrates an example of fragmentome signal with one or more components.

FIG. 1B illustrates an example of fragmentome signal with one or more components, each component affected by a clearance factor.

FIG. 3A shows a heat map corresponding to a PIK3CA|2238 genomic location with values of exon-normalized 10 bp (base pair) fragment start coverage (x-axis) ranging from about 0 to about 0.10 and values of centered median 10 bp fragment size (y-axis) ranging from about 148 bp to about 172 bp.

FIG. 3B shows a heat map corresponding to a PIK3CA|2238 genomic location with values of exon-normalized 10 bp fragment start coverage (x-axis) ranging from about 0.014 to about 0.035 and values of centered median 10 bp fragment size (y-axis) ranging from about 150 bp to about 185 bp.

FIG. 3C shows a heat map corresponding to a PIK3CA|2663 genomic location with values of exon-normalized 10 bp fragment start coverage (x-axis) ranging from about 0.028 to about 0.075 and values of centered median 10 bp fragment size (y-axis) ranging from about 155 bp to about 185 bp.

FIG. 3D shows a heat map corresponding to an EGFR|6101 genomic location with values of exon-normalized 10 bp fragment start coverage (x-axis) ranging from about 0.01 to about 0.061 and values of centered median 10 bp fragment size (y-axis) ranging from about 145 bp to about 186 bp. Each clinical sample is denoted by a solidly colored circle as follows: healthy controls are shown in dark green, and subjects with cancer are shown with a color ranging from blue, cyan, yellow, orange, and red (corresponding to maximum mutant allele fraction (max MAF) values of 0.1% to 93%, respectively. In practice, a blue colored circle may correspond to the minimum or lowest valued end of the spectrum (e.g., range of maximum MAF values across the cohort of subjects with cancer), while a red colored circle may correspond to the maximum or highest valued end of the spectrum (e.g., range of maximum MAF values across the cohort of subjects with cancer).

FIG. 4 shows a sample of a plasma deregulation score as it varies by position across a genome fragment in a given clinical sample (bottom panel). The top panel shows a list of relevant genes assayed and any alterations (SNVs or CNVs) found in those genes.

FIG. 21A shows a plot of normalized dinucleosomal-to-mononucleosomal count ratio in ERBB2 in 2,076 clinical samples. FIG. 21B shows a zoomed-in portion of the plot of FIG. 21A.

FIG. 25 shows an example of a K-component mixture model which can be used for anomaly detection using fragmentome signals.

FIG. 32C shows a zoomed-in portion of FIG. 32B.

DETAILED DESCRIPTION

Figure 1C:
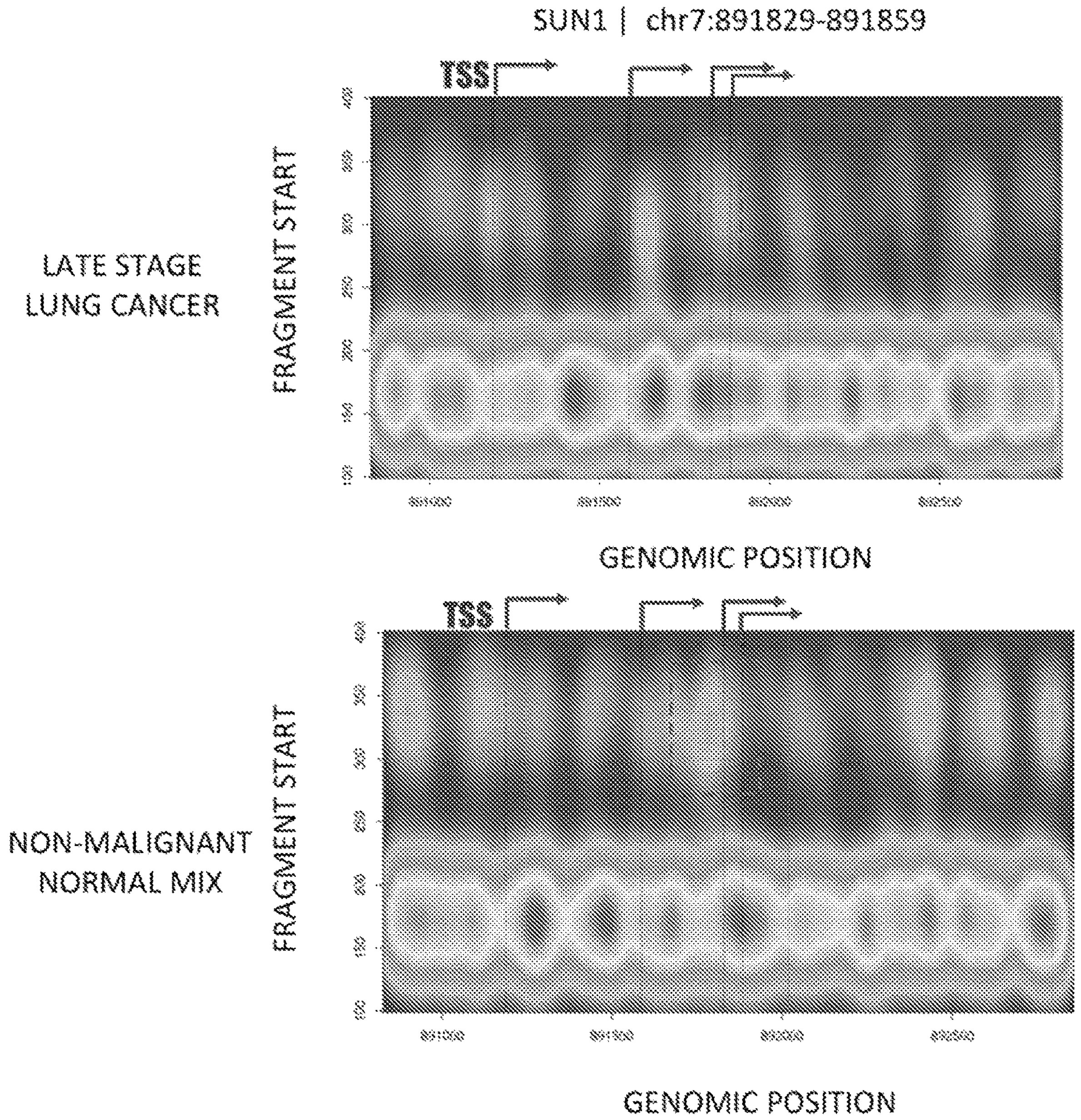
FIG. 1C illustrates variation in transcription start sites (TSS) as indicated by the presence of dinucleosomal complex in malignant (late stage lung cancer) versus normal samples.

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The term "biological sample," as used herein, generally refers to a tissue or fluid sample derived from a subject. A biological sample may be directly obtained from the subject. The biological sample may be or may include one or more nucleic acid molecules, such as deoxyribonucleic acid (DNA) or ribonucleic acid (RNA) molecules. The biological sample can be derived from any organ, tissue or biological fluid. A biological sample can comprise, for example, a bodily fluid or a solid tissue sample. An example of a solid tissue sample is a tumor sample, e.g., from a solid tumor biopsy. Bodily fluids include, for example, blood, serum, plasma, tumor cells, saliva, urine, lymphatic fluid, prostatic fluid, seminal fluid, milk, sputum, stool, tears, and derivatives of these.

The term "subject," as used herein, generally refers to any animal, mammal, or human. A subject may have, potentially have, or be suspected of having one or more characteristics selected from cancer, a symptom(s) associated with cancer, asymptomatic with respect to cancer or undiagnosed (e.g., not diagnosed for cancer). The subject may have cancer, the subject may show a symptom(s) associated with cancer, the subject may be free from symptoms associated with cancer, or the subject may not be diagnosed with cancer. In some embodiments, the subject is a human.

The term "cell-free DNA," (or "cfDNA") as used herein, generally refers to DNA fragments circulating freely in a blood stream of a subject. Cell-free DNA fragments may have dinucleosomal protection (e.g., a fragment size of at least 240 base pairs ("bp")). These cfDNA fragments with dinucleosomal protection were likely not cut between the nucleosome, resulting in a longer fragment length (e.g., with a typical size distribution centered around 334 bp). Cell-free DNA fragments may have mononucleosomal protection (e.g., a fragment size of less than 240 base pairs ("bp")). These cfDNA fragments with mononucleosomal protection were likely cut between the nucleosome, resulting in a shorter fragment length (e.g., with a typical size distribution centered around 167 bp). The cfDNA discussed herein may not have a fetal origin, and a subject usually may not be pregnant.

The term "DNA sequence," as used herein, generally refers to refers to "raw sequence reads" and/or "consensus sequences." Raw sequence reads are the output of a DNA sequencer, and typically include redundant sequences of the same parent molecule, for example after amplification. "Consensus sequences" are sequences derived from redundant sequences of a parent molecule intended to represent the sequence of the original parent molecule. Consensus sequences can be produced by voting (wherein each majority nucleotide, e.g., the most commonly observed nucleotide at a given base position, among the sequences is the consensus nucleotide) or other approaches such as comparing to a reference genome. Consensus sequences can be produced by tagging original parent molecules with unique or non-unique molecular tags, which allow tracking of the progeny sequences (e.g., after amplification) by tracking of the tag and/or use of sequence read internal information. Examples of tagging or barcoding, and uses of tags or barcodes, are provided in, for example, U.S. Patent Pub. Nos. 2015/0368708, 2015/0299812, 2016/0040229 and 2016/0046986, which is entirely incorporated herein by reference.

The sequencing method can be a first-generation sequencing method, such as Maxam- Gilbert or Sanger sequencing, or a high-throughput sequencing (e.g., next-generation sequencing or NGS) method. A high-throughput sequencing method may sequence simultaneously (or substantially simultaneously) at least 10,000, 100,000, 1 million, 10 million, 100 million, 1 billion, or more polynucleotide molecules. Sequencing methods may include, but are not limited to: pyrosequencing, sequencing-by-synthesis, single-molecule sequencing, nanopore sequencing, semiconductor sequencing, sequencing-by-ligation, sequencing-by-hybridization, Digital Gene Expression™ (Helicos™), massively parallel sequencing, e.g., Helicos™, Clonal Single Molecule Array (Solexa™/Illumina™), sequencing using PacBio™, SOLID™, Ion Torrent™ or Nanopore platforms.

The term "reference genome," (sometimes referred to as an "assembly") as used herein, generally refers to a nucleic acid sequence database, assembled from genetic data and intended to represent the genome of a species. Typically, reference genomes are haploid. Typically, reference genomes do not represent the genome of a single individual of the species but rather are mosaics of the genomes of several individuals. A reference genome can be publicly available or a private reference genome. Human reference genomes include, for example, hg19 or NCBI Build 37 or Build 38.

The term "reference sequence," as used herein, generally refers to a nucleotide sequence against which a subject's nucleotide sequences are compared. Typically, a reference sequence is derived from a reference genome.

The term "mapping," as used herein, generally refers to aligning a DNA sequence with a reference sequence based on sequence homology. Alignment can be performed using an alignment algorithm, for example, Needleman-Wunsch algorithm (see e.g., the EMBOSS Needle aligner available at the URL /Tools/psa/emboss_needle/nucleotide, optionally with default settings), the BLAST algorithm (see e.g., the BLAST alignment tool available at the URL blast.ncbi.nlm-.nih/Blast.cgi, optionally with default settings), or the Smith-Waterman algorithm (see e.g., the EMBOSS Water aligner available at the URL /Tools/psa/emboss_water/nucleotide, optionally with default settings). Optimal alignment may be assessed using any suitable parameters of a chosen algorithm, including default parameters.

The term "genomic region," as used herein, generally refers to any region (e.g., range of base pair locations) of a genome, e.g., an entire genome, a chromosome, a gene, or an exon. A genomic region may be a contiguous or a non-contiguous region. A "genetic locus" (or "locus") can be a portion or entirety of a genomic region (e.g., a gene, a portion of a gene, or a single nucleotide of a gene).

The term "quantitative measure," as used herein, generally refers to an absolute or relative measure. A quantitative measure can be, without limitation, a number, a statistical measurement (e.g., frequency, mean, median, standard deviation, or quantile), or a degree or a relative quantity (e.g., high, medium, and low). A quantitative measure can be a ratio of two quantitative measures. A quantitative measure can be a linear combination of quantitative measures. A quantitative measure may be a normalized measure.

The term "abnormal biological state," as used herein, generally refers to a state of a biological system that deviates in some degree from normal. Abnormal states can occur at the physiological or molecular level. For example, and without limitation, an abnormal physiological state (disease, pathology) or a genetic aberration (mutation, single nucleotide variant, copy number variant, gene fusion, indel, etc). A disease state can be cancer or pre-cancer. An abnormal biological state may be associated with a degree of abnormality (e.g., a quantitative measure indicating a distance away from normal state).

The term "likelihood," as used herein, generally refers to a probability, a relative probability, a presence or an absence, or a degree.

The term "machine learning algorithm," as used herein, generally refers to an algorithm, executed by computer, that automates analytical model building, e.g., for clustering, classification or pattern recognition. Machine learning algorithms may be supervised or unsupervised. Learning algorithms include, for example, artificial neural networks (e.g., back propagation networks), discriminant analyses (e.g., Bayesian classifier or Fischer analysis), support vector machines, decision trees (e.g., recursive partitioning processes such as CART-classification and regression trees, or random forests), linear classifiers (e.g., multiple linear regression (MLR), partial least squares (PLS) regression, and principal components regression), hierarchical clustering, and cluster analysis. A dataset on which a machine learning algorithm learns can be referred to as "training data."

The term "classifier," as used herein, generally refers to algorithm computer code that receives, as input, test data and produces, as output, a classification of the input data as belonging to one or another class.

The term "dataset," as used herein, generally refers to a collection of values characterizing elements of a system. A system may be, for example, cfDNA from a biological sample. Elements of such a system may be genetic loci. Examples of a dataset (or "data set") include values indicating a quantitative measure of a characteristic selected from: (i) DNA sequences mapping to a genetic locus, (ii) DNA sequences starting at a genetic locus, (iii) DNA sequences ending at a genetic locus; (iv) a dinucleosomal protection or mononucleosomal protection of a DNA sequence; (v) DNA sequences located in an intron or exon of a reference genome; (vi) a size distribution of DNA sequences having one or more characteristics; and (vii) a length distribution of DNA sequences having one or more characteristics, etc.

The term "value," as used herein, generally refers to an entry in a dataset can be anything that characterizes the feature to which the value refers. This includes, without limitation, numbers, words or phrases, symbols (e.g., + or −) or degrees.

The term "liquid biopsy," as used herein, generally refers to a non-invasive or minimally invasive laboratory test or assay (e.g., of a biological sample or cell-free DNA). Such "liquid biopsy" assays may report measurements (e.g., minor allele frequencies, gene expression, or protein expression) of one or more tumor-associated marker genes. Such liquid biopsy assays may be commercially available, such as, for example, a circulating tumor DNA test from Guardant Health, a Spotlight 59 oncology panel from Fluxion Biosciences, an UltraSEEK lung cancer panel from Agena Bioscience, a FoundationACT liquid biopsy assay from Foundation Medicine, and a PlasmaSELECT assay from Personal Genome Diagnostics. Such assays may report measurements of minor allele fraction (MAF) values for each of a set of genetic variants (e.g., SNVs, CNVs, indels, and/or fusions).

The term "multimodal density," as used herein, generally refers to a density or density distribution across multiple parameters. A multimodal density may include a multivariate mixture of distributions.

INTRODUCTION

Cancer formation and progression may arise from both genetic and epigenetic modifications of deoxyribonucleic acid (DNA). The present disclosure provides methods of analysis of epigenetic modifications of DNA, such as cell-free DNA (cfDNA). Such "fragmentome" analysis can be used alone or in combination with existing technologies to determine the presence or absence of a disease or condition, prognosis of a diagnosed disease or condition, therapeutic treatment of a diagnosed disease or condition, or predicted treatment outcome for a disease or condition.

Circulating cell-free DNA (cfDNA) may be predominantly short DNA fragments (e.g., having lengths from about 100 to 400 base pairs, with a mode of about 165 bp) shed from dying tissue cells into bodily fluids such as peripheral blood (plasma or serum). Analysis of cfDNA may reveal, in addition to cancer-associated genetic variants, epigenetic footprints and signatures of phagocytic removal of dying cells, which may result in an aggregate nucleosomal occupancy profile of present malignancies (e.g., tumors) as well as their microenvironment components.

One, two, or more components or factors may contribute to a plasma fragmentome signal (e.g., a signal obtained from analysis of cfDNA fragments), including (i) cell death type and associated chromatin condensation events during dismantling of DNA, (ii) clearance mechanisms, which may involve various types of engulfment machinery regulated by an immune system of a subject, and (iii) non-malignant variation in blood composition, which may be affected by an underlying combination of cell types in circulation, (iv) multiple sources or causes of non-malignant cell death in organs or tissues of a given type, and (v) heterogeneity of cell types within cancer, since malignant solid tumors include tumor-associated normal, epithelial, and stromal cells, immune cells, and vascular cells, any of all of which may contribute to and be represented in a cfDNA sample (e.g., which may be obtained from a bodily fluid of a subject).

Cell free DNA in the form of histone-protected complexes can be released by various host cells including neutrophils, macrophages, eosinophils, as well as tumor cells. Circulating DNA typically has a short half-life (e.g., about 10 to 15 minutes), and the liver is typically the major organ where circulating DNA fragments are removed from blood circulation. The accumulation of cfDNA in the circulation may result from increased cell death and/or activation, impaired clearance of cfDNA, and/or decreases in levels of endogenous DNase enzymes. Cell-free DNA (cfDNA) circulating in a subject's bloodstream may typically be packed into membrane-coated structures (e.g., apoptotic bodies) or complexes with biopolymers (e.g., histones or DNA-binding plasma proteins). The process of DNA fragmentation and subsequent trafficking may be analyzed for their effects on the characteristics of cell-free DNA signals as detected by fragmentome analysis.

In a cell nucleus (e.g., of a human), DNA typically exists in nucleosomes, which are organized into structures comprising about 145 base pairs (bp) of DNA wrapped around a core histone octamer. Electrostatic and hydrogen-bonding interactions of DNA and histone dimers may result in energetically unfavorable bending of DNA over the protein surface. Such bending may be sterically prohibitive to other DNA-binding proteins and hence may serve to regulate access to DNA in a cell nucleus. Nucleosome positioning in a cell may fluctuate dynamically (e.g., over time and across various cell states and conditions), e.g., partially unwrap and rewrap spontaneously. Since a fragmentome signal may reflect histone-protected DNA fragments that originated from a configuration influenced by nucleosomal units, nucleosome stability and dynamics may influence such a fragmentome signal. These nucleosome dynamics may stem from a variety of factors, such as: (i) ATP-dependent remodeling complexes, which may use the energy of ATP hydrolysis to slide the nucleosomes and exchange or evict histones from the chromatin fiber, (ii) histone variants, which may possess properties distinct from those of canonical histones and create localized specific domains within the chromatin fiber, (iii) histone chaperones, which may control the supply of free histones and cooperate with chromatin remodelers in histone deposition and eviction, and (iv) post-translational modifications (PTMs) of histones (e.g., acetylation, methylation, phosphorylation, and ubiquitination), which may directly or indirectly influence chromatin structure.

Hence, fragmentation signals or patterns in cfDNA may be indicative of an aggregate cfDNA signal, stemming from multiple events related to heterogeneity in chromatin organization across the genome. Such chromatin organization may differ depending on factors such as global cellular identity, metabolic state, regional regulatory state, local gene activity in dying cells, and mechanisms of DNA clearance. Moreover, cell free DNA fragmentome signals may be only partially attributed to underlying chromatin architecture of contributing cells. Such cfDNA fragmentome signals may be indicative of a more complex footprint of chromatin compaction during cell death and DNA protection from enzymatic digestion. Hence, chromatin maps specific to a given cell type or cell lineage type may only partially contribute to the inherent heterogeneity of DNA accessibility due to changes in nucleosome stability, conformation, and composition at various stages of cell death or debris trafficking. As a result, some nucleosomes may become preferentially present or not present in cell free DNA (e.g., there may be a filtering mechanism which influences cfDNA clearance and releases into the blood circulation), which may depend on factors such as the mode and mechanism of death and cell corpse clearance.

A fragmentome signal may be generated in a cell and released as cfDNA into blood circulation as a result of nuclear DNA fragmentation during cell processes such as apoptosis and necrosis. Such fragmentation may be produced as a result of different nuclease enzymes acting on DNA in different stages of cells, resulting in sequence-specific DNA cleavage patterns which may be analyzed in cfDNA fragmentome signals. Classifying such clearance patterns may be a clinically relevant marker of cell environments (e.g., tumor microenvironments, inflammation, disease states, tumorigenesis, etc.).

Fragmentome signals may be analyzed by classifying cfDNA fragments into distinct components corresponding to the different chromatin states from which they were derived. For example, a fragmentome signal may be expressed as a sum of components (e.g., benign systemic response, tumor systemic response, tumor microenvironment, and tumor) representing different underlying chromatin states, as shown in FIG. 1A. This "clearance of chromatin states" model may be modified by multiplying components by a clearance factor, since each chromatin state may have a different underlying clearance mechanism (e.g., specific to a tissue type, organ type, or tumor type). As shown in FIG. 1B, fragmentome signal may be modeled as a sum of one or more components, where each component is affected by (e.g., multiplied by) a clearance factor. Such components and clearance factors may represent non-variant markers that can be used to differentiate between similar or identical chromatin states. Fragmentome analysis may be performed using such a "clearance of chromatin states" model by identifying specific regions (or features) where one or more of the chromatin states, or one or more of their clearance mechanisms, are sufficiently different to be used as marker indicators of, e.g., genetic aberrations or disease states. Such genetic aberrations may comprise SNVs, CNVs, indels, fusions.

Fragmentome analysis may reveal canonical or non-canonical variations in chromatin organization or structures, which may be a consequence of genomic aberrations and/or epigenetic changes in DNA. Such measurements may reveal, e.g., one or more of: (i) a cancer-specific tumor microenvironment, (ii) a stromal response to physical stress resulting in stromal shedding characteristics that are cancer-specific, (iii) a blood cell composition change in response to a minuscule presence of immunologically active cancer fragments, and/or (iv) a blood composition response to subtle tissue immune profile variations that are associated with a budding tumor niche formation. Genetic aberrations that can be measured or inferred by fragmentome analysis may comprise epigenetic variants or changes.

Somatic copy number variants (CNV) that include focal amplifications and/or aneuploidy represent a group of genetic aberrations commonly observed in many cancers, especially metastatic cancers. Typically, copy number refers to a number of copies per cell of a particular gene or DNA sequence. However, such an interpretation of copy number (CN) may become less accurate when profiling heterogeneous multi-clonal tumor environments. Such tumor cells may have a wide range of CN across heterogeneous tumor cell populations.

Somatically acquired chromosomal rearrangements such as deletions and duplications, especially focal ones, may lead to the change of the expression level of a gene—a phenomenon known as the gene dosage effect.

Microarray technologies are widely used in CNV detection, such as array comparative genomic hybridization (array CGH) and single nucleotide polymorphisms (SNP) microarrays. In traditional array CGH, reference and test DNAs are fluorescence-labeled and hybridized to arrays, and the signal ratio is used as an estimate of the copy number (CN) ratio. SNP microarrays are also based on hybridization, but a single sample is processed on each microarray, and intensity ratios are formed by comparing the intensity of the sample under investigation to a collection of reference samples or to all other samples that are studied. While microarray/genotyping arrays are efficient for large CNV detection, they are less sensitive for detecting CNVs of short genes or DNA sequences (e.g., with a length of less than about 50 kilobases (kb)).

By providing a base-by-base view of the genome, next generation sequencing (NGS) may detect small or novel CNVs that may remain undetected by arrays. Examples of suitable NGS methods may include whole-genome (WGS), whole-exome sequencing (WES), or targeted exome sequencing (TES). However, challenges remain in developing computational algorithms for detecting CNVs (e.g., copy number amplifications (CNAs)) from an individual sequencing sample, due in part to biases introduced by hybridization and the sparse and uneven coverage throughout the genome.

Difficulties in acquiring tumor tissue (e.g., through costly and invasive biopsy procedures) and associated health risks have motivated development of minimally invasive blood-based assays. Profiling of blood may offer several practical advantages, including the minimally invasive nature of sample acquisition, relative ease of standardization of sampling protocols, and the ability to obtain repeated samples over time. Previous studies have identified cancer-associated variants, including microsatellite alterations and gene mutations, in the plasma of patients with different cancer types. Detecting cancer variants in the presence of large amounts of non-tumor DNA in plasma may present new challenges in copy number detection.

Figure 7:
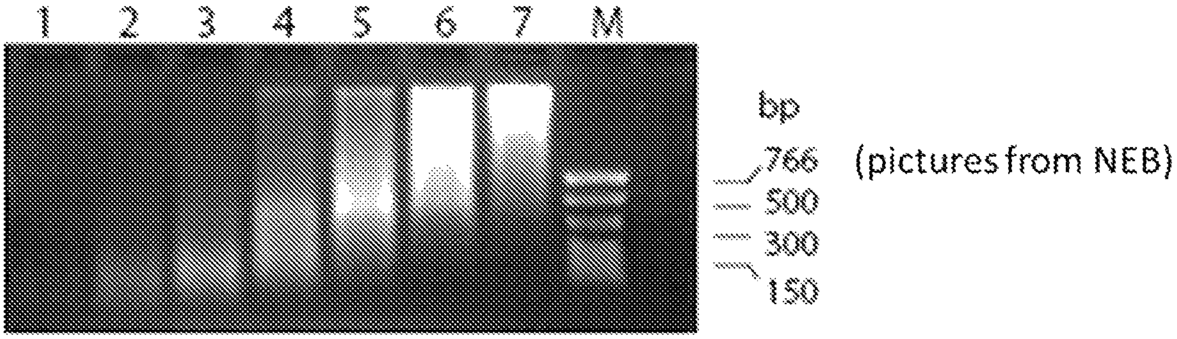
FIG. 7 illustrates an example of an enzyme which can cut double-stranded DNA between base pairs: micrococcal nuclease.

Moreover, plasma-derived cell free DNA retains characteristics previously noted in genome-wide analysis of chromatin structure (in particular, in micrococcal nuclease sequencing, or 'MNase-seq', assays), particularly those associated with epigenetic landscapes of human tissues as determined by examining the patterns of DNA fragmentation observed in cfDNA. FIG. 7 illustrates an example of an enzyme which can cut double-stranded DNA between base pairs: micrococcal nuclease (MNase). A 1:3 dilution of micrococcal nuclease can cleave at any base pair position without specificity to a particular sequence. MNase can digest chromatin and thereby provide information about the locations of nucleosomes along DNA strands. Studies of various model organisms and human cell lines have revealed that the positioning of the nucleosomes on DNA is variable and tissue-specific, making traditional copy number approaches relying on reference signal sub-optimal for plasma-derived DNA copy number detection of short CNV variants. In particular, cfDNA fragment copy number may depend on the nucleosomal positioning, cell clearance, and/or gene expression of an underlying cell or tissue type, which may be changing over time and cell states. Cell-free DNA signals have been observed to behave according to nucleosome positioning observed in tissue, such that the nucleosome depletion occurs at transcription start sites (TSSs) of actively expressing genes and hence that the prevalence of certain DNA fragments within TSSs directly reflects the expression signature of hematopoietic cells.

Figure 1D:
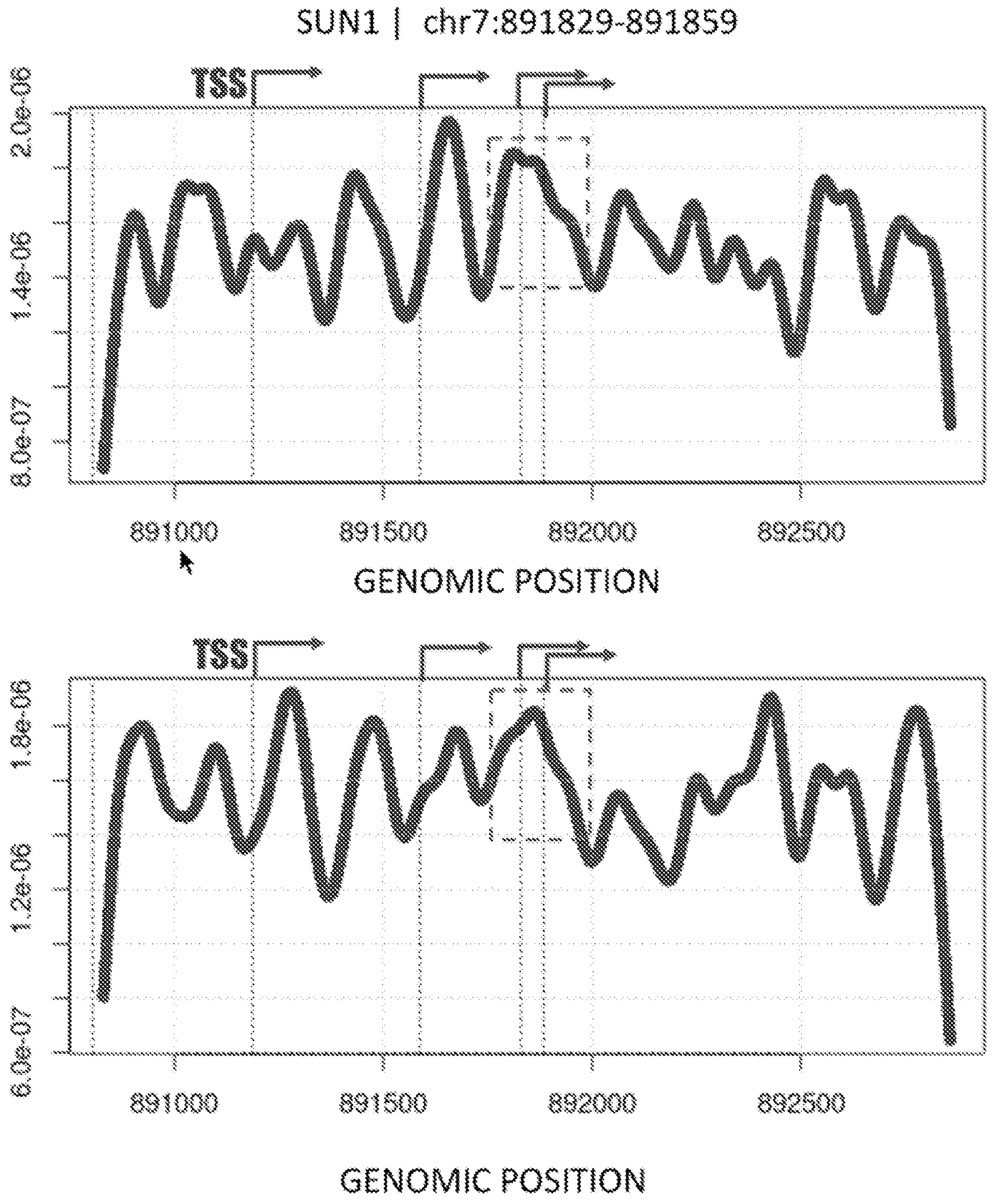
FIG. 1D illustrates limited resolution of univariate fragment start density in the same region.

Nucleosomes may be present even when genes are actively transcribed (e.g., by DNA polymerase II (Pol II)). However, nucleosome positioning is often changed over time in a cell, and some nucleosomes may be lost when transcription is induced. For example, on many eukaryotic genes, Pol II pauses after transcribing an initial 50 to 100 bp of the template. The original histones may remain on DNA during moderate-level transcription that involves DNA looping, while more significant remodeling may occur during intense transcription when multiple transcribing complexes displace histones. As a result, discrimination between mononucleosomal and di-nucleosomal nature of DNA fragments may aid in identifying and determining underlying regulation around transcription start sites (TSS), e.g., in cases of alternative TSS promoter usage, as shown in FIG. 1C, where univariate analysis of fragment start coverage does not reveal a presence of a dinucleosomal complex (e.g., which may be indicative of an alternative transcription start, as shown in FIG. 1D).

Despite recent advances in elucidating the origin of cell-free DNA, there remains a need for nucleosome-aware somatic variant detection algorithms. Nucleosome-aware variant detection approaches may extend our understanding of how nucleosome positioning influences cfDNA fragment patterns and signals, and may focus on extension of nucleosome-based analysis of cell-free DNA fragmentation patterns (fragmentomics) outside transcription factor binding and transcription start sites.

The present disclosure provides the use of a uni-parametric or a multi-parametric analysis to determine a plasma deregulation score. A uni-parametric analysis may comprise an analysis of a distribution function with one independent parameter. A multi-parametric analysis may comprise an analysis of a distribution function with two or more independent parameters. A plasma deregulation score may vary across the genome (e.g., across genomic locations). This variation may be based on, e.g., the number of fragments that overlap with each base position of a plurality of base positions. The plurality of base positions may be selected from a portion or all of the genome. This variation may be based on, e.g., the distribution of lengths of fragments that overlap with each position of a portion or all of the genome.

In one aspect, determining a plasma deregulation score may comprise plotting the number of cfDNA fragments in a sample (e.g., detected by NGS or other sequencing methods) that have a particular length at each of a set of genomic locations. This can be accomplished by a multi-parametric analysis, e.g., creating a three-dimensional (3-D) plot in which a first axis may represent a plurality of genomic locations overlapping with one or more regions of a genome (e.g., a contiguous span of a plurality of base pair positions, or a set of genomic regions as given in Table 1). A second axis of the 3-D plot may represent each of a set of possible lengths of fragments in the sample (e.g., 0 bp-400 bp). A third axis of the 3-D plot may represent the number of fragments that overlap with the unique genomic position at each of the lengths of fragments.

When the data is plotted in such a 3-D matrix, the resulting multi-parametric distribution plot can be used to determine a score. This score may be a plasma deregulation score, as described elsewhere herein.

In another aspect, determining a plasma deregulation score may comprise a uni-parametric analysis, e.g., creating a two-dimensional (2-D) plot in which a first axis may represent a plurality of genomic locations overlapping with one or more regions of a genome (e.g., a contiguous span of a plurality of base pair positions, or a set of genomic regions as given in Table 1). A second axis of the 2-D plot may represent the number of cfDNA fragments in a sample that have a particular length and that overlap with each of the plurality of genomic locations.

Fragmentome analysis may comprise one or more uni-parametric or multi-parametric analyses described above. Fragmentome analysis may comprise nucleosome profiling using cell-free nucleic acids, associating patterns of nucleosome profiling with specific phenotypes, such as a disease or condition, or configuring a classifier to help classify samples into one or more relevant classes. For example, a classifier uses intron-exon boundary information, comprising locations of intron-exon boundaries in a reference genome and fragmentome information (e.g., one or more multi-parametric or uni-parametric models) comprising values indicating location in an intron or exon or near an intron-exon boundary. Such intron-exon boundary information may be informative for discrimination of genetic variants or abnormal biological states. Fragmentome analysis may also be used, for example, to identify probes, primers, and baits that can be used to selectively enrich unique parts of the genome to detect relevant phenotypes.

Sequence Information

Figure 1E:
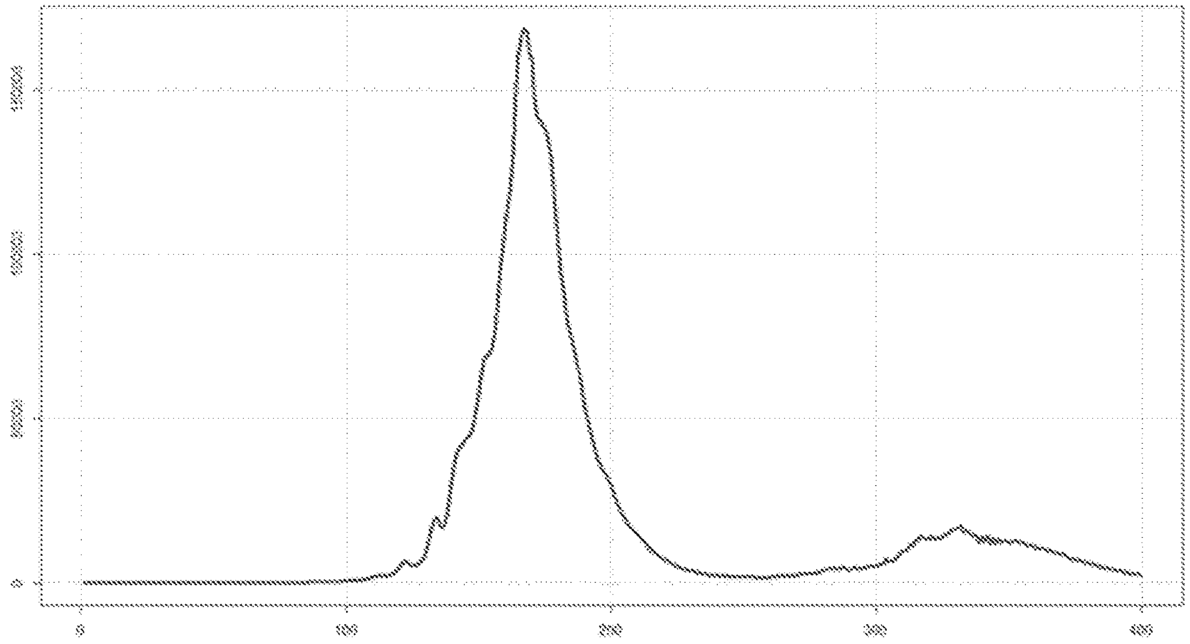
FIG. 1E illustrates a fragment length distribution of cell-free DNA (cfDNA) observed in clinical samples.

The fragmentome profiling herein utilizes sequence information derived from a sample of cell-free nucleic acid molecules. There are numerous ways to determine sequence information. Examples include sequencing using HiSeq (Illumina) or Ion Torrent (Thermo Fisher). In particular, paired-end sequencing may be used to measure the contiguity of single DNA molecules in plasma, e.g., to study the patterns of activation of endogenous endonucleases that cleave chromatin DNA into inter-nucleosomal fragments. Because of nucleosomal occupancy patterns, these cfDNA fragment lengths are observed as a distribution, as shown in FIG. 1E. The horizontal axis is fragment length (in base pairs, "bp"), while the vertical axis shows the number of cfDNA fragments with a given fragment length. A peak in the fragment length distribution is seen around 167 bp, which corresponds to about 147 bp of DNA wrapped around a histone octamer core and a segment of linker DNA. A smaller peak is also seen around 334 bp (e.g., at twice the fragment length of 167 bp), which corresponds to DNA wrapped twice around a histone octamer core (e.g., twice around a single histone or around two consecutive histones) with associated linker DNA. This peak of fragment length distribution of about 167 bp may be evident during multi-parametric analysis by observing one or more periodic peaks separated by about 167 bp along one or more axes of a multi-parametric heat plot.

Figure 2:
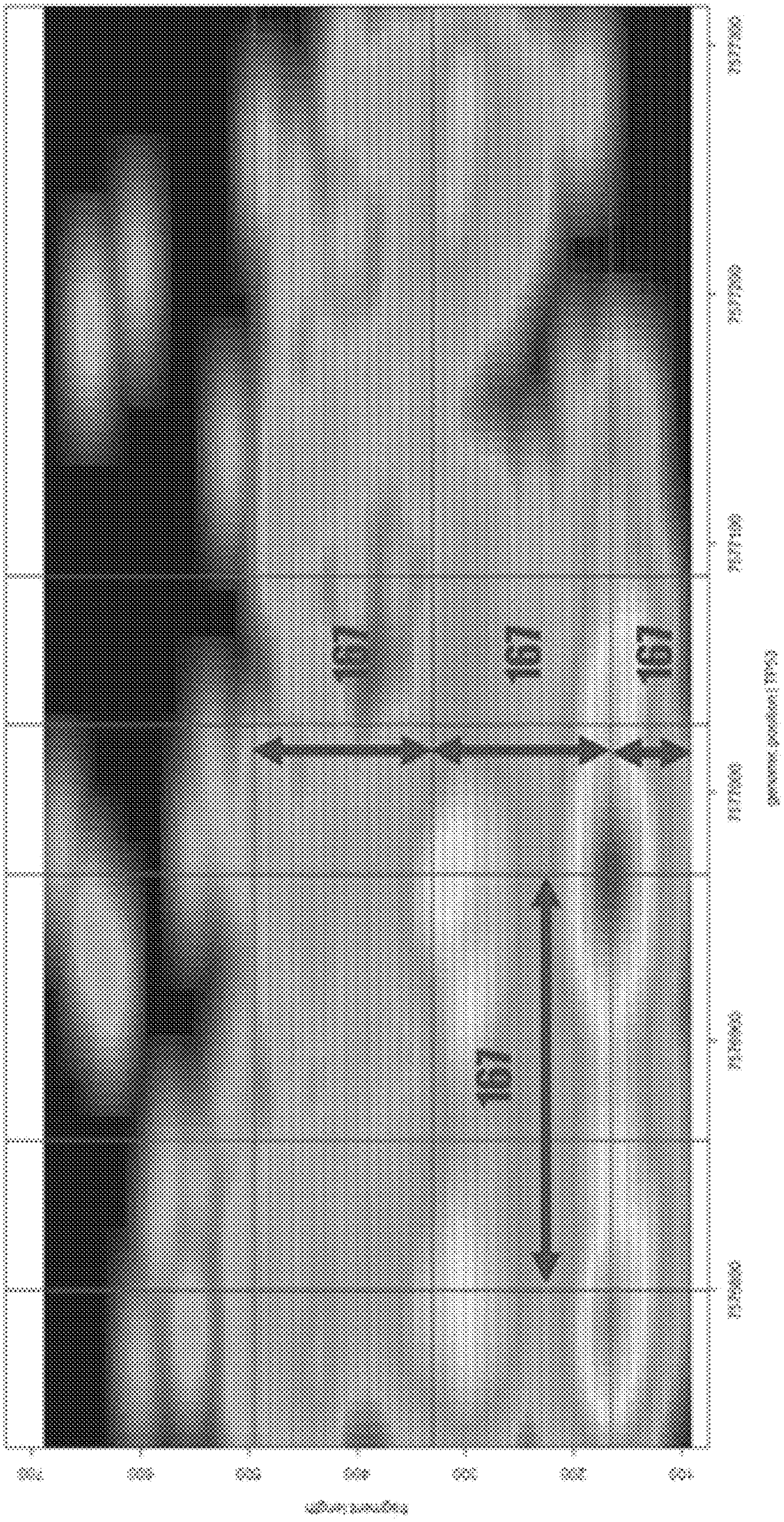
FIG. 2 illustrates an example of a heat plot of cfDNA fragments across fragment length and genomic position, i.e., a three-dimensional multi-parametric analysis.

In the presence of apoptotic DNA fragmentation observed in cfDNA signal, paired-end sequencing allows the determination of both position and occupancy of DNA-bound nucleosomes and transcription factors. In turn, this approach allows one to distinguish populations of molecules arising from different chromatin architecture profiles, even at sub-nucleosomal resolution. Examining how cfDNA fragments vary across a genomic start versus fragment length space may result in heat plot visualizations, as illustrated in FIG. 2.

After sequence data is acquired from cell-free nucleic acid samples, the sequence data may be aligned and collapsed into unique molecule reads. Methods for aligning include ClustalW2, Clustal Omega, and MAFFT.

The sequencing information derived herein can be optionally collapsed to determine unique molecules and/or unique sequence reads. Methods for collapsing into unique molecules are described by, e.g., Population Genetics's VeriTag, and Johns Hopkins University's SafeSeqS.

Techniques for sequencing cfDNA and mapping to reference genomes are known in the art e.g., see Chandrananda et al. (2015) *BMC Medical Genomics* 8:29.

Uni-Parameter Modeling

The present disclosure provides methods for uni-parametric modeling. A uni-parametric model may comprise performing a 2-D analysis on a 2-D distribution, e.g., a fragment count distribution. A uni-parametric model may comprise a set of positions in a genome. The genome may be a human genome. The genome may comprise one or more loci of reported tumor markers. The 2-D fragment count distribution may comprise a set of positions in a genome and a set of a number of fragments that align with each position in the set of positions in a genome. Such modeling can be used with a classifier, as described in more detail herein, to identify patterns or signatures associated with a condition or state of a condition, or to determine genetic aberrations (e.g., SNVs, CNVs, fusions, or indels) in a test subject. Other examples of uni-parametric models include, but are not limited to, a 2-D analysis on a 2-D starting position distribution, on a 2-D ending position distribution, or on a 2-D fragment length distribution.

A 2-D starting position distribution may comprise a set of positions in a genome and a set of numbers of fragments that start at each position in the set of positions in a genome.

A 2-D ending position distribution may comprise a set of positions in a genome and a set of numbers of fragments that end at each position in the set of positions in a genome.

A first 2-D fragment length distribution may comprise a set of positions in a genome and a set of lengths of fragments that overlap with each position in the set of positions in a genome.

A second 2-D fragment length distribution may comprise a set of lengths and a set of numbers of fragments that have a length in the set of lengths (e.g., as shown in FIG. 1E).

In an example, a uni-parametric model is used to detect an SNV in cell-free DNA from a subject. First, cell-free DNA is obtained from a bodily fluid sample from a subject with lung cancer. The cfDNA fragments are sequenced to produce a plurality of sequence reads of the fragments. Each sequence read is mapped to a set of a plurality of reference sequences from the human genome. For each base position in the set of reference sequences, the number of sequence reads that mapped to that base position is counted, thereby producing a 2-D fragment count distribution for the set of reference sequences. Among the set of reference sequences, one reference sequence is identified such that the 2-D fragment count distribution is unusually low (relative to the other references sequences in the set) at that reference sequence. This is interpreted biologically as a reference sequence containing a locus with upregulated gene expression. This reference sequence contains the EGFR L858R single nucleotide polymorphism locus. Thus, a uni-parametric model performed "variant-free" detection the presence of an EGFR L858R SNV without using the base identity of base positions in the reference sequence (i.e., without directly detecting the SNV through nucleotide identity variation in a sequence). This SNV detection may then be used to determine a clinical diagnosis, prognosis, therapy selection, therapy prediction, therapy monitoring, etc.

Multi-Parametric Modeling

After sequence data from a sample is generated, a multi-parametric analysis of the sequence data may be performed to generate a multi-parametric model. A multi-parametric analysis refers to any analysis that utilizes multiple parameters (data sets) simultaneously. For example, a multi-parametric analysis may comprise a distribution function (with function value y) with n independent variables (with values $x_1, x_2, \ldots, x_n$), wherein n is an integer of at least 2. For example, in one instance, a multi-parametric analysis may comprise generating a distribution plot along the genome that designates on a mappable base-by-base axis (e.g., across each of a plurality of genomic positions across a genome) the number of unique molecules that span that base and the number of unique molecules that start at that base. As another example, a multi-parametric analysis may comprise generating a distribution plot of the number of fragments (e.g., the function value y) associated with each input vector $[x_1, x_2, \ldots, x_n]$, wherein each $x_i$ is an independent variable (of a plurality of n independent variables) across the sequencing read data. An example of such an input vector may be one where $x_1$ is a mappable base position (e.g., among a plurality of such genomic positions across a genome) that is spanned by a cfDNA fragment and $x_2$ is the length in bases of a cfDNA fragment (e.g., "fragment length"). Coverage values (e.g., counts) of a number of DNA fragments may be normalized or un-normalized, since fragmentome analysis typically comprises analysis of a relative distribution of fragments (e.g., relative to different subjects, samples drawn at different time points, different genomic positions or gene loci, etc.).

Parameters may be indicative of one or more of: (i) a length of the DNA fragments that align with each of the plurality of base positions in the genome, (ii) a number of the DNA fragments that align with each of the plurality of base positions in the genome, and (iii) a number of the DNA fragments that start or end at each of the plurality of base positions in the genome. A multi-parametric model may comprise two or more such parameters. Such parameters may be normalized or un-normalized values.

Multi-parametric modeling, like uni-parametric modeling can yield patterns that indicate clusters, or regions, of genomic structural variation or instability (e.g., as a result of nucleosomal occupancy or positioning).

Fragmentome profiling may be performed by generating one or more multi-parametric or uni-parametric models from a cell-free nucleic acid sample, thereby generating a fragmentome profile of the cell-free nucleic acid sample. One or more fragmentome profiles (or fragmentome data) may be subjected to unsupervised clustering to reveal one or more classes of distinct abnormal biological states. One or more fragmentome profiles (or fragmentome data) may be incorporated into a classifier (e.g., using machine learning techniques) to determine a likelihood of that a subject belongs to one or more classes of clinical significance. A class of clinical significance may be a category, for example, indicating an abnormal biological state or a genetic variant. Examples of classes of clinical significance include (i) presence or absence of one or more genetic variants, (ii) presence or absence of one or more cancers, (iii) presence or absence of one or more canonical driver mutations, (iv) presence or absence of one or more disease subtypes (e.g., lung cancer molecular subtypes), (v) likelihood of response to a treatment (e.g., drug or therapy) for cancer or other disease, disorder, or abnormal biological state, (vi) presence or absence of a copy number variation (CNV) (e.g., ERBB2 amplification), or (vii) information derived from tumor microenvironment (e.g., tissue of origin corresponding to cfDNA fragments).

One or more fragmentome profiles (or fragmentome data) may be incorporated into a classifier to determine the likelihood of presence or absence of one or more canonical driver mutations. A driver mutation may be a mutation that gives a selective advantage to a clone in its microenvironment, through either increasing its survival or reproduction. A driver mutation may be a somatic mutation associated with cancer or another abnormal biological state. Presence of a driver mutation may be indicative of cancer diagnosis, stratification of a subject with a cancer subtype, tumor burden, tumor in a tissue or organ, tumor metastasis, efficacy of treatment, or resistance to treatment. A canonical driver mutation may be a mutation that is well known in the art, e.g., a mutation listed in the Catalogue of Somatic Mutations in Cancer (COSMIC) (available at the URL cancer.sanger.ac.uk/cosmic). Examples of canonical driver mutations include Epidermal Growth Factor Receptor (EGFR) Exon 19 deletion, EGFR Exon 19 insertion, EGFR G719X, EGFR Exon 20 insertion, EGFR T790M, EGFR L858R, and EGFR L861Q in lung cancer. Such information about the likelihood of presence or absence of one or more canonical driver mutations may be used to diagnose a subject (e.g., with lung cancer), stratify a subject with a diagnosis (e.g., a molecular subtype of lung cancer), select a treatment to treat a subject with a disease or other abnormal biological state (e.g., a drug such as a targeted treatment at a given dose), cease a treatment to treat a subject with a disease or other abnormal biological state, change a treatment to treat a subject with a disease or other abnormal biological state (e.g., from a first drug to a second drug, or from a first dose to a second dose), or perform further medical testing (e.g., imaging or biopsy) on the subject.

One or more fragmentome profiles (or fragmentome data) may be incorporated into a classifier to determine the likelihood of presence or absence of one or more disease subtypes (e.g., lung cancer molecular subtypes in a subject). For example, EGFR T790M and EGFR L858R are two molecular subtypes of lung cancer. Such information about the likelihood of presence or absence of one or more disease subtypes may be used to diagnose a subject (e.g., with lung cancer), stratify a subject with a diagnosis (e.g., a molecular subtype of lung cancer), select a treatment to treat a subject with a disease or other abnormal biological state (e.g., a drug such as a targeted treatment at a given dose), cease a treatment to treat a subject with a disease or other abnormal biological state, change a treatment to treat a subject with a disease or other abnormal biological state (e.g., from a first drug to a second drug, or from a first dose to a second dose), or perform further medical testing (e.g., imaging or biopsy) on the subject.

One or more fragmentome profiles (or fragmentome data) may be incorporated into a classifier to determine the likelihood of response to a treatment (e.g., drug or therapy for cancer or other disease, disorder, or abnormal biological state) of a subject. For example, a treatment may be a targeted treatment such as a tyrosine kinase inhibitor (TKI) designed to treat EGFR-positive lung cancer. Examples of TKIs are erlonitib and gefinitib. Such information about the likelihood of response to a treatment of a subject may be used to select a treatment to treat a subject with a disease or other abnormal biological state (e.g., a drug such as a targeted treatment at a given dose), cease a treatment to treat a subject with a disease or other abnormal biological state, change a treatment to treat a subject with a disease or other abnormal biological state (e.g., from a first drug to a second drug, or from a first dose to a second dose), or perform further medical testing (e.g., imaging or biopsy) on the subject.

One or more fragmentome profiles (or fragmentome data) may be incorporated into a classifier to determine the likelihood of information derived from tumor microenvironment (e.g., tissue of origin corresponding to cfDNA fragments). Since a fragmentome profile may comprise a characteristic signal (or signature) from circulating nucleic acids in blood, such a signature may comprise an aggregate signal from tumor cells, leukocytes and other background cells, and a tumor's microenvironment. A tumor's cell biology and microenvironment may both play roles in affecting the tumor biology and activity. Thus, such information about the likelihood of information derived from tumor microenvironment may be used to identify tissue of origin (e.g., that tumor activity is prevalent in a tissue or organ). Such information may be deconvolved to identify subcomponents (e.g., inflamed organ, leukocytes, tumor, normal apoptotic cells). Such subcomponent information may be used to determine the tissue(s) and/or organ(s) where a tumor is located.

A multi-parametric analysis can be represented by a 2-D density plot (e.g., a heat plot, or heat map), an example of which is shown in FIG. 2. The horizontal axis may be a first independent variable (e.g., genomic position across a plurality of genomic regions in the genome). The vertical axis is a second independent variable (e.g., cfDNA fragment length). The heat plot has a plurality of colors that represent different quantiles of distribution function values (e.g., function valuey) across the range of distribution function values. For example, a heat plot may comprise a plurality among six colors (blue, cyan, green, yellow, orange, and red), each successive color in the set representing a distribution function value in the first, second, third, fourth, fifth, and sixth quantiles of the range of distribution function values, respectively. Alternatively, a heat plot may comprise continuous combinations of a plurality of discrete colors (e.g., blue, cyan, green, yellow, orange, and red), each color representing a linearly weighted combination of a plurality of discrete colors, according to each heat plot point's function value's relative percentile within the range of distribution function values. Such a heat plot may be three-dimensional (3-D). However, many other approaches for generating multi-dimensional may be used. In some instances, a multi-parametric analysis comprises 2, 3, 4, 5, 6, 7, 8, 9, 10, 11, 12, 13, 14, 15, 16, 17, 18, 19, 20, or more than 20 dimensions analyzed simultaneously.

As seen in FIG. 2, such a heat plot may reveal periodicity across genomic position or fragment length as a result of typical patterns in cfDNA fragment distribution (FIG. 1E). This periodicity may be about 167 bp in either the horizontal axis or the vertical axis of the heat plot.

One multi-parametric analysis generates a multi-parametric model, such as a heat map as one example, data mining tools can be used to identify non-random, systematic patterns. Such patterns can include associations of peak heights or width of peaks as related to a phenotype of cohorts such as those diagnosed with a condition (e.g., cardiovascular condition, infection, inflammation, auto-immune disorder, cancer, diagnosed with a specific type of cancer, diagnosed with a specific stage of cancer, etc.).

Figure 3:
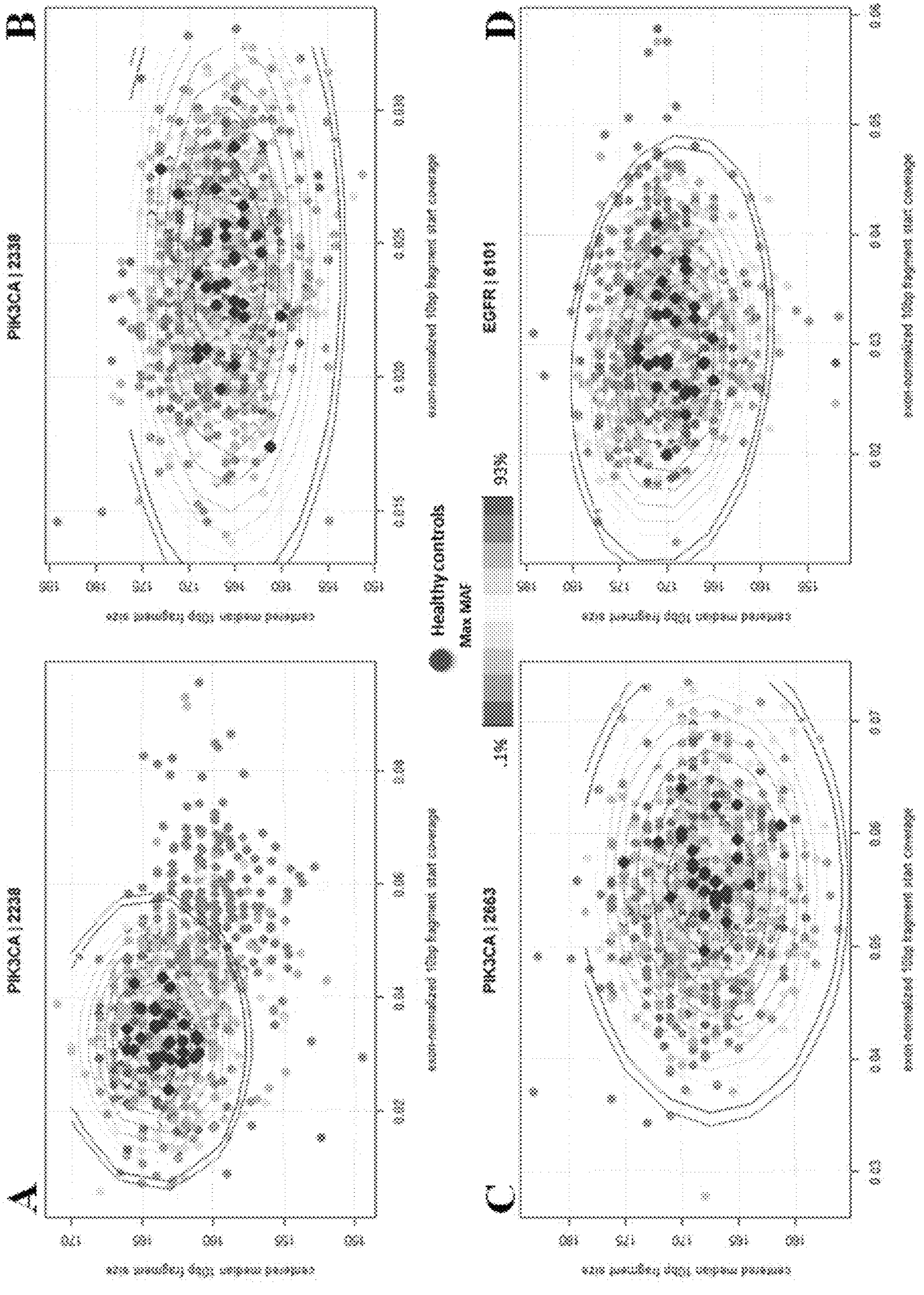
FIGS. 3A-3D illustrate examples of 4 transformed multi-parametric heat maps showing a plasma deregulation metric for three different genomic locations (two from PIK3CA and one from EGFR).

Once a multi-parametric heat map has been generated, this space may be transformed in one of a number of different ways, e.g., using multivariate machine learning techniques or direct modeling of residual variation of 2-D density plots relative to a non-malignant cohort (as shown in FIG. 3). For example, one can establish in a multi-parametric analysis a metric of plasma deregulation (distribution function valuey) as a function of fragment abundance ($x_1$) and fragment length ($x_2$) at a given genomic position. Such a functional form can be as simple as (1) a L2 norm in normalized coverage and fragment length space, or can be expressed as (2) a bivariate normal approximation of the negative controls and/or healthy donors reference set. As an example of the latter (2), a plasma deregulation metric can be a negative of a logarithm of a bivariate normal density with probability contour ellipses determined by a first moment and a second moment of the data, e.g., using robust multivariate location and scale estimate with a high breakdown point (also known as Fast Minimum Covariance Determinant estimators).

To illustrate an embodiment of data transformations, FIGS. 3A-3D illustrate examples of 4 different transformed multi-parametric heat maps showing a plasma deregulation metric for three different sets of genomic locations (two from PIK3CA and one from EGFR). Each heat map was generated by a transformation of fragment start and width density to a plasma deregulation metric across more than two thousand clinical samples. The horizontal axis may denote exon-normalized 10 bp fragment start coverage. The vertical axis may denote centered median 10 bp fragment size. Each clinical sample is denoted by a solidly colored circle as follows: healthy controls are shown in dark green, and subjects with cancer are shown with a color ranging from blue, cyan, yellow, orange, and red (corresponding to maximum mutant allele fraction (MAF) values of 0.1% to 93%, respectively. In practice, a blue colored circle may correspond to the minimum or lowest valued end of the spectrum (e.g., range of maximum MAF values across the cohort of subjects with cancer), while a red colored circle may correspond to the maximum or highest valued end of the spectrum (e.g., range of maximum MAF values across the cohort of subjects with cancer).

From FIGS. 3A and 3B, we observe that for the PIK3CA|2238 set of genomic locations, cancer subjects with high maximum MAF (e.g., denoted by red circles) tend to have lower values for centered median 10 bp fragment size and higher values for exon-normalized 10 bp fragment start coverage compared to healthy controls (e.g., denoted by green circles). From FIG. 3C, we also observe that for the PIK3CA|2663 set of genomic locations, cancer subjects with high maximum MAF (e.g., denoted by red circles) tend to have higher values for centered median 10 bp fragment size an lower values for exon-normalized 10 bp fragment start coverage compared to healthy controls (e.g., denoted by green circles). From FIG. 3D, we also observe that for the EGFR|6101 set of genomic locations, cancer subjects with high maximum MAF (e.g., denoted by red circles) tend to have higher values for centered median 10 bp fragment size and higher values for exon-normalized 10 bp fragment start coverage compared to healthy controls (e.g., denoted by green circles). For each of these 3 sets of genomic locations, shifts in both (1) the distribution of centered median 10 bp fragment size and (2) the distribution of exon-normalized 10 bp fragment start coverage (e.g., shifts in both x-axis and y-axis) are observed in the cancer subject cohort as compared to the healthy controls. These observations of distribution shifts in a multi-parametric distribution as a result of cancer status were apparent independently of sequence read data analysis (e.g., bioinformatics analysis), and may be used as a basis (e.g., either alone or in conjunction with other clinically observed data) to identify single nucleotide variants (SNVs), copy number variations (CNVs), insertions and deletions (indels), or other conventional genetic aberrations.

In an example, a multi-parametric model is used to detect cancer by analyzing cell-free DNA from a subject. First, cell-free DNA was obtained from bodily fluid samples from a set of multiple subjects with cancer and subjects without cancer. The cfDNA fragments were sequenced to produce a plurality of sequence reads of the fragments. Each sequence read was mapped to a set of a plurality of reference sequences from the human genome. A multi-parametric model was generated as follows: for each value in a set of centered median 10 bp fragment size values (first variable), for each value in a set of exon-normalized 10 bp fragment start coverage values (second variable), and for each genomic location in the PIK3CA|2663 set of genomic locations (third variable), the MAF of each healthy control subject without cancer was plotted in green and the MAF of each subject with cancer was plotted on a color spectrum representing the MAF (e.g., increasing from blue to yellow to orange to red). Among this multi-parametric model, it was observed that cancer subjects with high maximum MAF (e.g., denoted by red circles) tend to have higher values for centered median 10 bp fragment size an lower values for exon-normalized 10 bp fragment start coverage compared to healthy controls (e.g., denoted by green circles). Next, the same procedure above was repeated for a first and a second test subjects with unknown cancer status. The circle associated with the first test subject fell within the range representative of a healthy control (e.g., the region with a cluster of green circles), hence the first test subject was diagnosed as negative for cancer based on this test. The circle associated with the second test subject fell within the range representative of a subject with cancer (e.g., the region with a cluster of red circles) with a very high MAF of 90%, hence the second test subject was diagnosed as positive for cancer or referred for further biopsy testing based on this test. A multi-parametric model was thereby performed on cfDNA samples from subjects to detect cancer in these subjects.

One or more multiple filtering techniques may be applied to the multi-parametric distribution data, either prior to arriving at the calculated plasma deregulation metric or after the plasma deregulation metric is established. Filtering techniques may create an approximating function that attempts to capture important information, trends, or parameters in a set of data (e.g., a set of granular data), while leaving out noise or other fine-scale phenomena. For sample, filtering techniques may enable more information to be extracted from a set of data or to enable analyses that are flexible or robust. Sample filtering techniques include moving averages, global polynomials, splines, digital smoothing (e.g., a Butterworth filter, a Fourier smoothing, etc.), a Wigner transform, a Continuous Wavelet Transform (CWT), and a Discrete Wavelet Transform (DWT). Filtering techniques may also involve removing assay-specific noise via subtraction of pre-defined fragment start coverage associated with assay biases, e.g., enrichment-related biases associated with targeted capture. A contrived sample representing uniform fragment distribution may be assayed, and fragment-length enrichment observed in such contrived samples may be used to correct clinical sample signals (e.g., by fitting and/or subtracting assay-related components of the signal). Alternatively or additionally, fragment counts can be further normalized to correct biases from plasma DNA degradation. Such degradation can stem from, e.g., handling and storage, and can result in changes in anticipated fragment length distribution and/or a presence of contaminated genomic DNA.

As an example, FIG. 4 shows a sample of a plasma deregulation score as it varies by position across a genome fragment in a given clinical sample (bottom panel). The top panel shows a list of relevant genes assayed and any alterations (SNVs or CNVs) found in those genes. A plasma deregulation score may be a value representing plasma deregulation at localized genomic regions. A plasma deregulation score may be indicative of a canonical envelope (e.g., a region (e.g., an area) of a multi-parametric distribution) where most DNA fragmentome signals originating from healthy cells are observed. A plasma deregulation score may be generated by using a training set of non-malignant healthy control subjects (without a disease of interest) and performing a multi-parametric analysis on cfDNA samples from each subject of the training set. Next, regions may be identified where fragments are observed with specified frequency (e.g., 90%, 95%, 96%, 97%, 98%, 99%, 99.9%, 99.99%, 99.999%, or 99.995%) over the cohort. Next, these regions may be masked, such that densities outside these regions are identified. Next, these densities may be aggregated (or summed) to obtain a plasma deregulation score. Such a plasma deregulation score may be indicative of, for example, a mutation burden, a tumor burden, or a disease burden.

An example of a plasma deregulation score may be a variant-free coverage (VCF) score, which indicates a number of DNA fragments covering a given genomic region or base position. A low value of plasma deregulation score may indicate a relatively low level of plasma deregulation at a localized genomic region. A high value of plasma deregulation score may indicate a relatively high level of plasma deregulation at a localized genomic region. Plasma deregulation scores may be represented by different colors to indicate relative differences (e.g., a different color for each different quantile in a plurality of quantiles across a range of plasma deregulation scores), e.g., as seen in a uni-parametric heat plot (or heat map) or a multi-parametric heat plot (or heat map).

Referring again to FIG. 4, a number of different peaks in plasma deregulation score can be observed, which correspond to a number of well-established cancer marker genes (e.g., PIK3CA, MYC, CDKN2A, CCND1, CCND2, KRAS, CDK4, RB1, and ERBB2). Different peaks in plasma deregulation score can be associated with known tumor markers, e.g., somatic mutations reported in the Catalogue of Somatic Mutations in Cancer (COSMIC).

By generating multi-parametric models across a large number (e.g., hundreds to thousands, or more) of clinical samples, such multi-parametric models may yield metrics (e.g., plasma deregulation score) comprising empirical features that can either be associated with specific cancer types or analyzed to discover somatic or other types of variants. Such information can then be incorporated into a variant-free somatic variant classifier. As an example, unsupervised clustering of plasma deregulation scores across multiple genomic regions in 5,000 non-small cell lung carcinoma (NSCLC) patients' samples can be analyzed and visualized as a heat plot.

Figure 5:
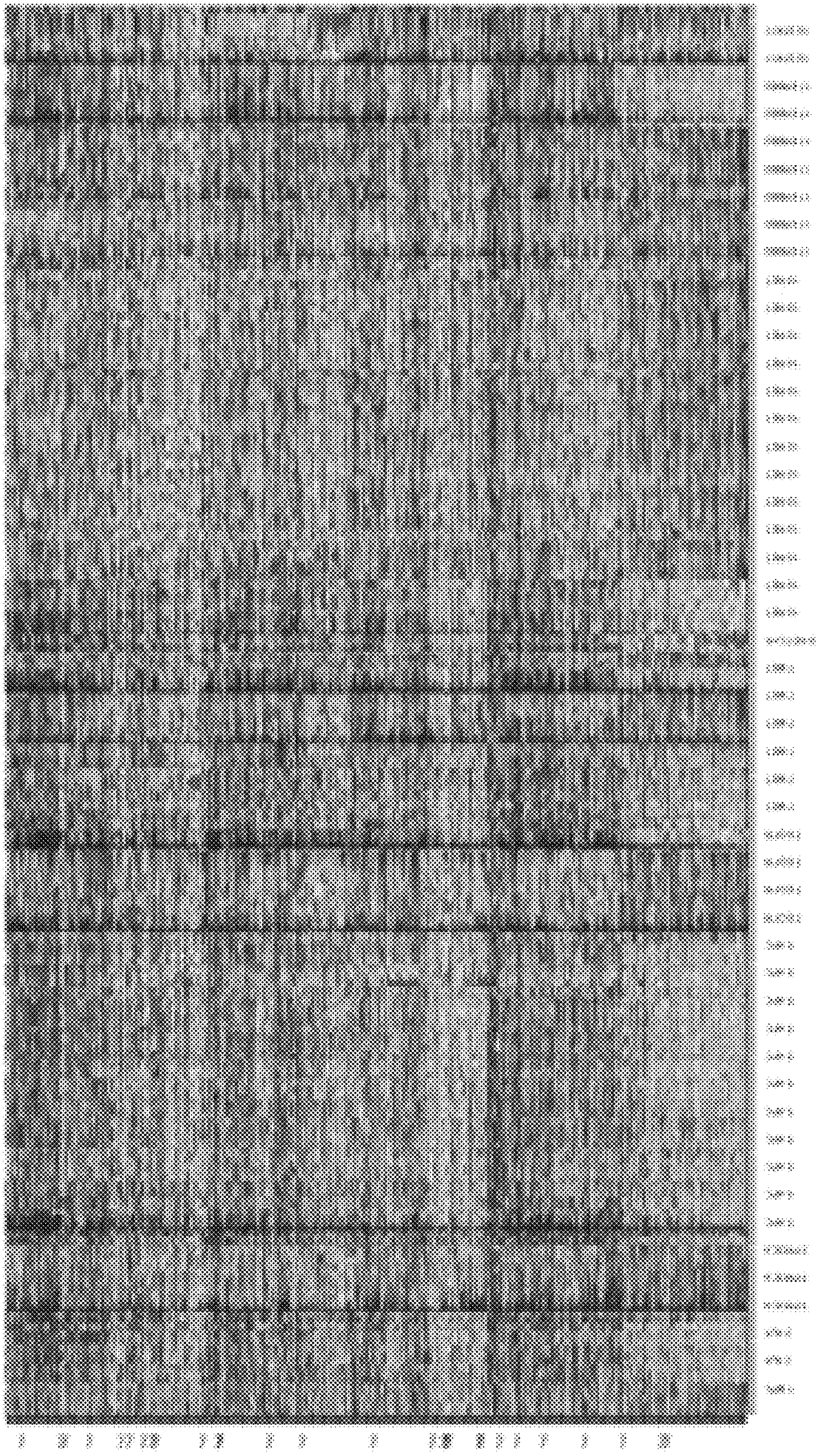
FIG. 5 shows a heat plot generated by unsupervised clustering of plasma deregulation scores across multiple genomic regions in a 5,000 samples, each from a different non-small cell lung carcinoma (NSCLC) patient. Y-axis reflects each of the 5,000 patient samples. X-axis reflects a panel of genomic locations analyzed. The color reflects the plasma deregulation score for each genomic location for each sample.

For example, FIG. 5 shows a heat plot generated by unsupervised clustering of plasma deregulation scores across multiple genomic regions in a 5,000 samples, each from a different non-small cell lung carcinoma (NSCLC) patient. Y-axis reflects each of the 5,000 patient samples. X-axis reflects a panel of genomic locations analyzed. The color reflects the plasma deregulation score for each genomic location for each sample. The entire data set was clustered using unsupervised clustering algorithm. Based on this heat map, we can use this data to identify regions that can be used as hot spots for variant-free classification of patients. Such classification can be used to identify patients to be included in a clinical trial, to be given a certain therapy, to be taken off a therapy treatment, etc.

The horizontal (longer) axis may denote genomic location across a plurality of genomic locations in a genome. The vertical (shorter) axis may denote clinical samples (e.g., each row illustrates data from one clinical sample). Such a heat plot can reveal areas of relatively high plasma deregulation (e.g., in areas of red, orange, and yellow colors) and areas of relatively low plasma deregulation (e.g., in areas of blue and green colors).

Figure 6:
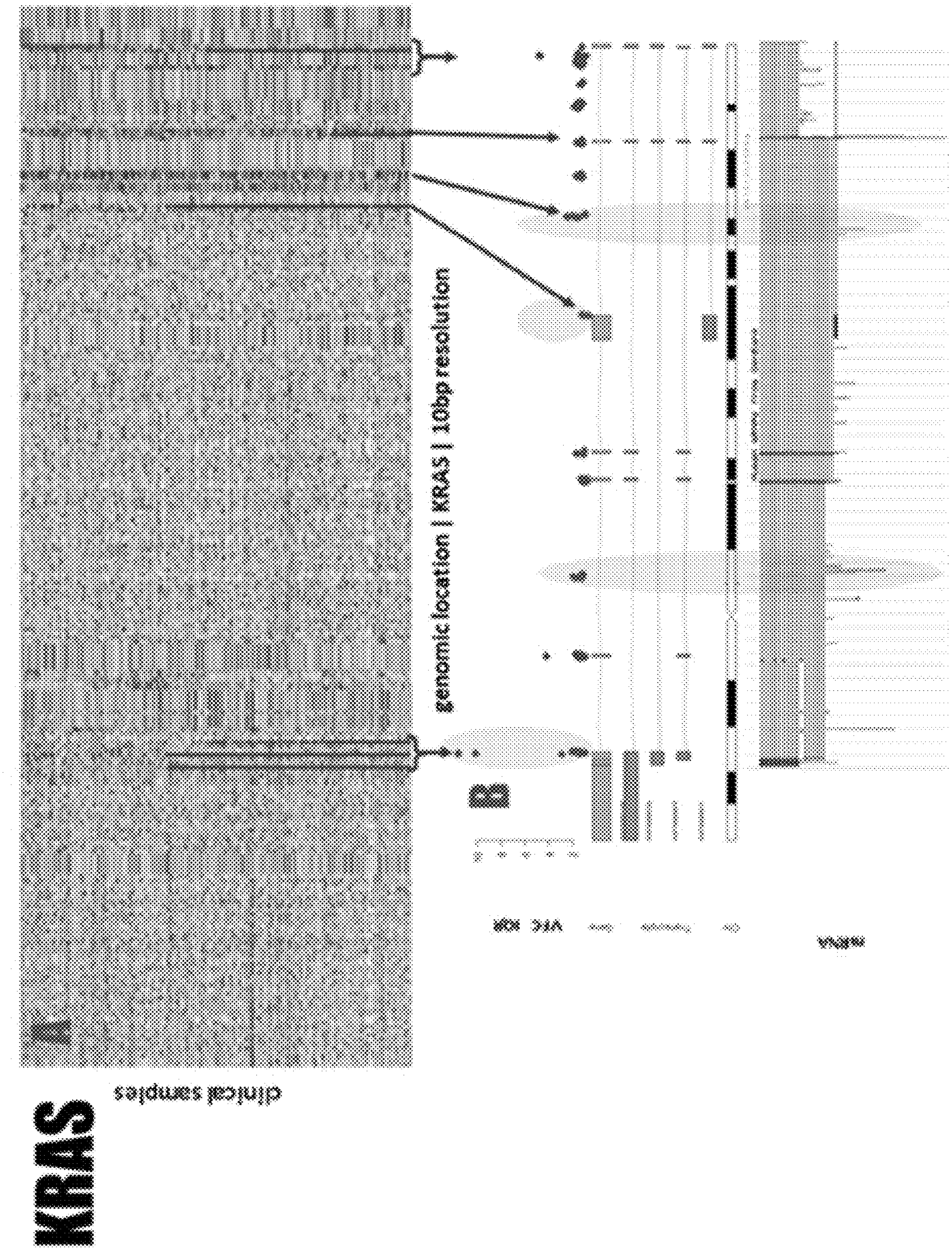
FIG. 6 shows a heat map generated across a small range of genomic locations, e.g., the KRAS gene. In this case, a plasma deregulation score has 10 bp resolution, e.g., it is calculated every 10 bp. The Y-axis provides information for 2,000 clinical samples. The X-axis provides the plasma deregulation score across the KRAS gene at a resolution of 10 bp.

As another example of a multi-parametric model, a heat map can be generated across genomic locations (e.g., at 10 base-pair ("bp") resolution) to visualize a single gene (e.g., KRAS) across a large number of clinical samples (e.g., 2000), as shown in FIG. 6 (part A). The horizontal axis may denote genomic location across a plurality of genomic locations (e.g., that span a KRAS gene) in a genome. The vertical axis may denote clinical samples (e.g., each row illustrates data from one clinical sample). In this analysis, KRAS variant-free coverage values (VFCs) with at least one reported variant are visualized in the heat plot (FIG. 6 (part A)). The top high var (variable) bins are placed in genomic order and overlaid with transcript isoforms and mRNA profiles (FIG. 6 (part B)).

Observed features of plasma deregulation scores generated from one or more uni-parametric and/or multi-parametric models across a large number of clinical samples may be incorporated within well-known somatic mutation detection and quantification methods approaches to improve detection sensitivity of such somatic mutation detection and quantification methods. For example, in current methods to detect and quantify copy number variations (e.g., CNVs) in cell-free nucleic acids such as cfDNA, a typical coverage metric (e.g., a calculated ratio of a number of molecules comprising a variant to a reference number of molecules without a variant) may be adjusted or replaced by a metric corresponding to shifts in a multi-parametric model.

Observed features of plasma deregulation scores generated from one or more uni-parametric and/or multi-parametric models across a large number of clinical samples may be clustered and subjected to enrichment analysis to produce a plasma profile association with underlying somatic changes. This approach may lead to a calculation or determination of probabilistic likelihoods for a set of one or more somatic mutations (e.g., known tumor markers) to be present in a patient from whom a cfDNA sample was obtained, by using variant-free plasma deregulation scores.

One or more uni-parametric models generated from a cell-free DNA sample of a subject may be incorporated into a classifier (e.g., a machine learning engine) that is trained to classify said sample as having or not having each of a set of single nucleotide variants (SNVs) or other genetic variants. These SNVs or other genetic variants may be found in one or more genes selected from Table 1. This classifier may be a variant-free classifier (e.g., does not classify based on somatic mutation identification). This classifier may be a variant-aware classifier (e.g., does classify based on somatic mutation identification).

A variant-free classifier may determine the presence or absence of a sequence aberration at a locus in a genome without taking into account a base identity at each of a plurality of base positions in any locus or sub-locus of the genome, wherein said plurality of base identities are indicative of a known somatic mutation. A sub-locus may be a plurality of contiguous base positions such that said plurality is a subset of a locus in a genome. A variant-free classifier may use a uni-parametric or multi-parametric analysis to determine the presence or absence of the sequence aberration in a locus in a subject. This locus may be a reported tumor marker. This locus may be a tumor marker that was not previously reported.

A variant-aware classifier may determine the presence or absence of a sequence aberration at a first locus in a genome by taking into account a base identity at each of a plurality of base positions in one or more loci or sub-loci of the genome, wherein said plurality of base identities are indicative of a known somatic mutation, and wherein the first locus is not among the one or more loci or sub-loci of the genome. In other words, a variant-aware classifier may identify a sequence aberration at a given locus by incorporating information about known somatic mutations detected at any other loci in a genome.

Alternatively, one or more multi-parametric models generated from a cell-free DNA sample of a subject may be incorporated into a classifier (e.g., a machine learning engine) that is trained to classify said sample as having or not having each of a set of single nucleotide variants (SNVs) or other genetic variants. These SNVs or other genetic variants may be selected from Table 1. This classifier may be a variant-free classifier (e.g., does not classify based on somatic mutation identification). This classifier may be a variant-aware classifier (e.g., does classify based on somatic mutation identification). Multi-parametric models may comprise one or more data sets including any information that is associated with one or more genetic loci, e.g., values indicating a quantitative measure of a characteristic selected from: (i) DNA sequences mapping to a genetic locus, (ii) DNA sequences starting at a genetic locus, (iii) DNA sequences ending at a genetic locus; (iv) a dinucleosomal protection or mononucleosomal protection of a DNA sequence; (v) DNA sequences located in an intron or exon of a reference genome; (vi) a size distribution of DNA sequences having one or more characteristics; (vii) a length distribution of DNA sequences having one or more characteristics, or (viii) any combination thereof.

Alternatively, one or more uni-parametric models and one or more multi-parametric models generated from a cell-free DNA sample of a subject may be incorporated into a classifier (e.g., a machine learning engine) that is trained to classify said sample as having or not having each of a set of single nucleotide variants (SNVs) or other genetic variants. These SNVs or other genetic variants may be selected from Table 1. This classifier may be a variant-free classifier (e.g., does not classify based on somatic mutation identification). This classifier may be a variant-aware classifier (e.g., does classify based on somatic mutation identification). Uni-parametric models may comprise one or more data sets including any information that is associated with one or more genetic loci, e.g., values indicating a quantitative measure of a characteristic selected from: (i) DNA sequences mapping to a genetic locus, (ii) DNA sequences starting at a genetic locus, (iii) DNA sequences ending at a genetic locus; (iv) a dinucleosomal protection or mononucleosomal protection of a DNA sequence; (v) DNA sequences located in an intron or exon of a reference genome; (vi) a size distribution of DNA sequences having one or more characteristics; (vii) a length distribution of DNA sequences having one or more characteristics, or (viii) any combination thereof.

In addition to metrics such as plasma deregulation score, multi-parametric analysis may also reveal tumor-relevant information of a subject. In one example, the number of reads in any given position in a genome may yield insights toward the tumor status of a subject from which the cell-free nucleic acid sample was acquired, such as tissue of origin, tumor burden, tumor aggressiveness, tumor druggability, tumor evolution and clonality, and tumor resistance to treatment.

In another example, the number of reads in any given position in a genome interposed with the length of the reads at that position in the genome, and may yield insight into tumor status of a subject from which the cell-free DNA sample was acquired, such as tissue of origin, tumor burden, tumor aggressiveness, tumor druggability, tumor evolution and clonality, and tumor resistance to treatment.

The patterns, e.g., height of peaks, width of peaks, appearance of new peaks, shift of peaks, and/or smears, in a model can serve as an indicator of a phenotype. In some instances, a nucleosome profile of an individual is compared to a reference multi-parametric model or pattern to determine a phenotype or change in phenotype.

In an aspect, disclosed herein is a method for generating an output indicative of a presence or absence of a genetic aberration in deoxyribonucleic acid (DNA) fragments from a cell-free sample (or cell-free DNA) obtained from a subject. The method may comprise constructing (e.g., by a computer) a distribution of the DNA fragments from the cell-free sample (or cell-free DNA) over a plurality of base positions in a genome. Next, the output indicative of a presence or absence of the genetic aberration in the subject may be determined using the distribution. The presence or absence may be determined (i) without comparing the distribution of the DNA fragments to a reference distribution from a source external to a genome of the subject, (ii) without comparing parameters derived from the distribution of the DNA fragments to reference parameters, and/or (iii) without comparing the distribution of the DNA fragments to a reference distribution from a control of the subject. In some embodiments, the genetic aberration comprises a copy number variation (CNV) and/or a single nucleotide variant (SNV). In some embodiments, the distribution comprises one or more multi-parametric distributions.

In an aspect, disclosed herein is a method for processing biological samples of a subject for DNA fragments with dinucleosomal protection and/or DNA fragments with mononucleosomal protection. The processing may comprise obtaining a biological sample of a subject. The biological sample may comprise deoxyribonucleic acid (DNA) fragments. The assaying may comprise generating a signal indicative of a presence or absence of (i) DNA fragments with dinucleosomal protection associated with a genetic locus from one or more genetic loci and/or (ii) DNA fragments with mononucleosomal protection associated with the genetic locus. Such generated signals may be used to generate an output indicative of a presence or absence of (i) DNA fragments with dinucleosomal protection associated with a genetic locus from one or more genetic loci and/or (ii) DNA fragments with mononucleosomal protection associated with the genetic locus. The assaying may comprise enriching the biological sample for DNA fragments for a set of one or more genetic loci. Such genetic loci may comprise tumor-associated genetic loci and/or non-tumor-associated genetic loci. The assaying may comprise sequencing the DNA fragments of the biological sample.

In another aspect, disclosed herein is a method for generating an output indicative of a presence or absence of a genetic aberration in deoxyribonucleic acid (DNA) fragments from a cell-free sample (or cell-free DNA) obtained from a subject. The generating may comprise constructing (e.g., by a computer) a distribution of the DNA fragments from the cell-free sample (or cell-free DNA) (e.g., over a plurality of base positions in a genome). Next, for each of one or more genetic loci, a quantitative measure may be calculated (e.g., by a computer) which indicative of a ratio of (1) a number of the DNA fragments with dinucleosomal protection associated with a genetic locus from the one or more genetic loci, and (2) a number of the DNA fragments with mononucleosomal protection associated with the genetic locus, or vice versa. Next, the output indicative of a presence or absence of the genetic aberration in the one or more genetic loci in the subject may be generated. The generation may use the quantitative measure for each of the one or more genetic loci. In some embodiments, the distribution comprises one or more multi-parametric distributions.

Reference Models

A reference multi-parametric model may be derived from different samples obtained from the same subject at different points in time. Some or all of such samples can comprise cell-free DNA. Alternatively, one or more of these samples can be derived directly from the tumor (e.g., via a biopsy or fine needle aspirate). Models derived from such samples can be used to monitor a patient's cancer, observe clonality in the cancer, detect new mutations, and drug resistance.

A reference multi-parametric model may be derived from stromal tissue from the surrounding tumor microenvironment of the subject. DNA used for such model can be derived during biopsy, for example. A model derived from stromal tissue can be used to create a baseline multi-parametric model. This can allow for early observations of new variations in the tumor derived cell-free DNA.

A reference multi-parametric model may be derived from sheared genomic (non-cell free) DNA from a healthy asymptomatic individual. The sheared DNA can be used to simulate a healthy individual's cell free DNA sample. For example, such sheared DNA samples may be used for normalization of fragmentome signals. For example, sheared DNA can be generated and used in experiments to validate and optimize capture efficiency of a set of one or more probes (e.g., in a targeted assay).

A reference multi-parametric model may be derived from a fragmentome (e.g., nucleosomal) profile of a given tissue type. Examples of nucleosomal occupancy profiling techniques include, Statham et al., Genomics Data, Volume 3, March 2015, Pages 94-96 (2015).

Using the multi-parametric models of reference samples, one can determine fragmentome (e.g., nucleosomal) patterns or profiles associated with apoptotic processes and necrotic processes. Detection of such patterns can then be used, independently or in conjunction, to monitor a condition in a subject. For example, as a tumor expands, the ratio of necrosis to apoptosis in the tumor micro-environment may change. Such changes in necrosis and/or apoptosis can be detected using the methods described herein using fragmentome profiling.

A distance function may be derived from a fragmentome profile by calculating the difference between (1) a uni-parametric or multi-parametric model of a subject and (2) a reference uni-parametric or multi-parametric model (e.g., typical of a healthy population).

Fragmentome Signatures

In an example, cohorts of subjects having a phenotype (e.g., asymptomatic healthy individuals, or individuals having a particular type of cancer) can have their fragmentome profile assayed using the methods herein. The fragmentome profiles of the cohort members are analyzed and a fragmentome signature of the cohort is determined. A subject tested de novo can have their profile classified by a trained classifier (a trained database) into one or more classes using the fragmentome signatures of two or more cohorts.

Cohorts of individuals may all have a shared characteristic. This shared characteristic may be selected from the group consisting of: a tumor type, an inflammatory condition, an apoptotic condition, a necrotic condition, a tumor recurrence, and resistance to a treatment. An apoptotic condition may be, for example, a disease or condition that causes a higher likelihood of cell death by apoptosis than necrosis, as compared to a healthy subject. The apoptotic condition may be selected from the group consisting of: an infection and cellular turnover. A necrotic condition may be, for example, a disease or condition that causes a higher likelihood of cell death by necrosis than apoptosis, as compared to a healthy subject. The necrotic condition may be selected from the group consisting of: a cardiovascular condition, sepsis, and gangrene.

In some instances, a cohort comprises individuals having a specific type of cancer (e.g., breast, colorectal, pancreatic, prostate, melanoma, lung or liver). To obtain the nucleosome signature of such cancer, each such individual provides a blood sample. Cell-free DNA is obtained from such blood samples. The cell-free DNA of such cohorts is sequenced (either with or without selective enrichment of a set of regions from the genome). Sequence information in the form of sequence reads from the sequencing reactions are mapped to the human genome. Optionally, molecules are collapsed into unique molecule reads either before or after the mapping operation.

Since cell-free DNA fragments in a given sample represent a mix of cells from which the cell-free DNA arose, the differential nucleosomal occupancy from each cell type may result in a contribution toward the mathematical model representative of a given cell-free DNA sample. For example, a distribution of fragment lengths may have arisen due to differential nucleosomal protection across different cell types, or across tumor vs. non-tumor cells. This method may be used to develop a set of clinically useful assessments based on the uni-parametric, multi-parametric, and/or statistical analysis of sequence data.

The models may be used in a panel configuration to selectively enrich regions (e.g., fragmentome profile associated regions) and ensure a high number of reads spanning a particular mutation, important chromatin-centered events like transcription start sites (TSSs), promoter regions, junction sites, and intronic regions may also be considered.

For example, differences in fragmentome profiles are found at or near junctions (or boundaries) of introns and exons. Identification of one or more somatic mutations may be correlated with one or more multi-parametric or uni-parametric models to reveal genomic locations where cfDNA fragments are distributed. This correlation analysis may reveal one or more intron-exon junctions where fragmentome profile disruptions are most pronounced. For example, a fragmentome profile disruption may be due to a different isoform of protein being expressed, causing a binding site is being altered, thereby changing the nucleosomal protection of cfDNA fragments that can be empirically observed as a differential signature and distribution of cfDNA fragments at intron-exon junctions, where the specific locations of the intron-exon junctions are associated with a start of the isoform. Intron-exon boundaries may be included in panel configuration to selectively enrich these regions, which may give better discrimination (e.g., determination of differential likelihood) of a disease or other abnormal biological state. This approach may improve panel design by focusing on exon-intron junctions instead of, or in addition to, entire exon regions.

Fragmentome profiles can be combined with existing panels of somatic mutations. In some instances, the use of SNV information in combination with fragmentome profiling can increase sensitivity or accuracy of an SNV call. For example, if a certain SNV is predominantly present in shorter fragments than average (e.g., less than 155, 154, 153, 152, 151, 150, 149, or 148 bp in length), then it is more likely that the SNV is a somatic mutation. If an SNV is found predominantly in longer fragments than average (e.g., more than 155, 156, 157, 158, 159, 160, 161, 162, 163, 164, 165, or 166) then it is more likely that the SNV is a germline SNV. Therefore, an assay of the disclosure may involve determining SNV in unique molecules from a cell free DNA sample as well as fragment size of each unique molecule and adjusting the confidence score of the calling of a somatic SNV based on the size distribution of the unique molecules which include the SNV.

The fragmentome profiling analysis may comprise performing a uni-parametric or multi-parametric analysis of cell-free DNA representative of a subject. From a given subject's sequence data, one or more expected distributions may be generated for each base position across the reference genome, where each expected distributions describes one or more of: the number of reads that map to the given position, the cell-free DNA fragment lengths that map to the given position, the number of cell-free DNA fragments that start at the given position, and the number of cell-free DNA fragments that end at the given position.

By performing base pair-wise comparisons between sample and reference at a given locus of a genome, observations of any deviations from this pattern (e.g., increased or decreased number of reads than expected at a given base position, or a shift in the distribution) reveal tumor-relevant information, such as tumor burden, tumor type, tumor clonality or heterogeneity, tumor aggressiveness, etc. Such deviations are downstream consequences of nucleosomal positioning variation and of cellular processes.

For example, abnormal cellular processes such as infection, inflammation, and tumor growth and invasiveness influence the relative contributions of apoptotic and necrotic pathways to shed DNA into bloodstream, where the cell-free DNA fragments circulate and are collected as part of blood samples for liquid biopsy applications. Since apoptotic processes cut across nucleosomes, these processes may give rise to longer reads (e.g., longer fragments) where nucleosomes are present. Since the nucleosomal protection is different in tumor cells than normal cells, different data patterns may be observed across cohorts, e.g., between cancer and normal, or between two tumor types.

To perform a fragmentome profiling analysis, a collection of cell-free DNA molecules may be provided from a blood sample collected from a subject. The cell-free DNA may be in the form of short fragments (most of which are less than 200 base pairs in length). The cell-free DNA may be subjected to library preparation and high-throughput sequencing to generate sequence information representative of cell-free DNA molecules from the sample. After alignment, multi-parametric analysis may be performed on the aligned sequence information to generate a multi-parametric model representative of the cell-free DNA molecules from the sample.

A uni-parametric analysis may be performed on a set of two data sets using said sequence information to generate a uni-parametric model representative of the cell-free DNA molecules from the sample, wherein the uni-parametric model has two dimensions. A data set may comprise a vector of quantitative values. A uni-parametric model may comprise two data sets, for example, such that one data set comprises a y-axis and one data set comprises an x-axis.

A multi-parametric analysis may be performed on a plurality of three or more data sets using said sequence information to generate a multi-parametric model representative of the cell-free DNA molecules from the sample, wherein the multi-parametric model has three or more dimensions. A multi-parametric model may comprise three data sets, for example, such that one data set comprises a z-axis (or shaded color), one data set comprises a y-axis, and one data set comprises an x-axis.

The data sets chosen for a uni-parametric or multi-parametric analysis may be selected from the group consisting of: (a) start position of fragments sequenced, (b) end position of fragments sequenced, (c) number of unique fragments sequenced that cover a mappable position, (d) fragment length, (e) a likelihood that a mappable base-pair position will appear at a terminus of a sequenced fragment, (f) a likelihood that a mappable base-pair position will appear within a sequenced fragment as a consequence of differential nucleosome occupancy, and (g) a sequence motif of fragments sequenced. A sequence motif is a sequence of 2-8 base pairs long located at a terminus of a fragment, which may be used to identify patterns in the sequence information and may be incorporated into classification schemes.

A uni-parametric analysis may comprise mapping one parameter to each of two or more positions or regions of the genome. This parameter may be selected from the group consisting of: (a) start position of fragments sequenced, (b) end position of fragments sequenced, (c) number of unique fragments sequenced that cover a mappable position, (d) fragment length, (e) a likelihood that a mappable base-pair position will appear at a terminus of a sequenced fragment, and (f) a likelihood that a mappable base-pair position will appear within a sequenced fragment as a consequence of differential nucleosome occupancy. These two or more positions or regions of a genome may include at least one region associated with one or more of the genes of interest, which are listed in Table 1.

A multi-parametric analysis may comprise mapping two or more parameters to each of two or more positions or regions of the genome. These parameters may be selected from the group consisting of: (a) start position of fragments sequenced, (b) end position of fragments sequenced, (c) number of unique fragments sequenced that cover a mappable position, (d) fragment length, (e) a likelihood that a mappable base-pair position will appear at a terminus of a sequenced fragment, and (f) a likelihood that a mappable base-pair position will appear within a sequenced fragment as a consequence of differential nucleosome occupancy. These two or more positions or regions of a genome may include at least one region associated with one or more of the genes of interest, which are listed in Table 1.

TABLE 1

| Point Mutations (SNVs) | | | | | | Amplifications (CNVs) | | Fusions | Indels |
|---|---|---|---|---|---|---|---|---|---|
| AKT1 | ALK | APC | AR | ARAF | ARID1A | AR | BRAF | ALK | EGFR |
| ATM | BRAF | BRCA1 | BRCA2 | CCND1 | CCND2 | CCND1 | CCND2 | FGFR2 | (exons |
| CCNE1 | CDH1 | CDK4 | CDK6 | CDKN2A | CDKN2B | CCNE1 | CDK4 | FGFR3 | 19 & 20) |
| CTNNB1 | EGFR | ERBB2 | ESR1 | EZH2 | FBXW7 | CDK6 | EGFR | NTRK1 | ERBB2 |
| FGFR1 | FGFR2 | FGFR3 | GATA3 | GNA11 | GNAQ | ERBB2 | FGFR1 | RET | (exons |
| GNAS | HNF1A | HRAS | IDH1 | IDH2 | JAK2 | FGFR2 | KIT | ROS1 | 19 & 20) |
| JAK3 | KIT | KRAS | MAP2K1 | MAP2K2 | MET | KRAS | MET | | MET |
| MLH1 | MPL | MYC | NF1 | NFE2L2 | NOTCH1 | MYC | PDGFRA | | (exon 14 |
| NPM1 | NRAS | NTRK1 | PDGFRA | PIK3CA | PTEN | PIK3CA | RAF1 | | skipping) |
| PTPN11 | RAF1 | RB1 | RET | RHEB | RHOA | | | | |
| RIT1 | ROS1 | SMAD4 | SMO | SRC | STK11 | | | | |
| TERT | TP53 | TSC1 | VHL | | | | | | |

Cell-free DNA may comprise a footprint representative of its underlying chromatin organization, which may capture one or more of: expressing-governing nucleosomal occupancy, RNA Polymerase II pausing, cell death-specific DNase hypersensitivity, and chromatin condensation during cell death. Such a footprint may carry a signature of cell debris clearance and trafficking, e.g., DNA fragmentation carried out by caspase-activated DNase (CAD) in cells dying by apoptosis, but also may be carried out by lysosomal DNase II after the dying cells are phagocytosed, resulting in different cleavage maps. Genome partitioning maps can be constructed by genome wide identification of differential chromatin states in malignant vs non-malignant conditions associated with aforementioned properties of chromatin via aggregation of significant windows into regions of interest. Such regions of interest are generally referred to as genome partitioning maps.

The two or more positions or regions of a genome may be identified by (i) providing one or more genome partitioning maps, and (ii) selecting from the genome partitioning maps the positions or regions of a genome, each such position or region of a genome mapping to a gene of interest. The two or more positions or regions of a genome may be each between 2 and 500 base pairs in length. These positions or regions of the genome represent localized genomic regions associated with genes of interest for further analysis.

The multi-parametric analysis may comprise generating a heat map of the two or more regions of the genome. This heat map may give a visual representation of how the two or more parameters vary across the positions of a given genome. The two or more regions of the genome may include at least one region selected from one or more of the genes listed in Table 1. Heat maps representative of a large number (e.g., more than 100) of subjects within a cohort or across cohorts can be combined to generate one or more reference heat maps that are representative of the given cohort or group of cohorts to which the subjects belong. For example, cohorts may include subjects that share a characteristic, e.g., a diagnosed disease (e.g., a tumor type), a disease state in common (e.g., a healthy control), or a disease outcome in common (e.g., a tumor recurrence or resistance to treatment).

The multi-parametric analysis may further comprise applying one or more mathematical transforms to generate a multi-parametric model. The multi-parametric model may be a joint distribution model of two or more variables selected from the group consisting of: (a) start position of fragments sequenced, (b) end position of fragments sequenced, (c) number of unique fragments sequenced that cover a mappable position, (d) fragment length, (e) a likelihood that a mappable base-pair position will appear at a terminus of a sequenced fragment, (f) a likelihood that a mappable base-pair position will appear within a sequenced fragment as a consequence of differential nucleosome occupancy, and (g) a sequence motif. From a multi-parametric model, one or more peaks may be identified. Each such peak may have a peak distribution width and a peak coverage.

Uni-parametric or multi-parametric models representative of a large number (e.g., at least 50, 100, 200, 300, 500, 700, 1000, 2000, 3000, 5000, or more) of subjects within a cohort or across cohorts may be combined to generate one or more reference uni-parametric or multi-parametric models, respectively, that are representative of the given cohort or group of cohorts to which the subjects belong. For example, cohorts may include subjects that have a common diagnosed disease (e.g., a tumor type), a common disease state (e.g., a healthy control), or a common disease outcome (e.g., a tumor recurrence).

The uni-parametric or multi-parametric analysis may further comprise measuring RNA expression of the cell-free DNA molecules. The uni-parametric or multi-parametric analysis may further comprise measuring methylation of the cell-free DNA molecules. The uni-parametric or multi-parametric analysis may further comprise measuring nucleosomal mapping of the cell-free DNA molecules. Since nucleosomal occupancy is linked to guanine-cytosine (GC) content of sequenced fragments, methylation level can be indirectly assessed, for example, by examining TSS areas where methylation repression can be inferred from nucleosomal occupancy. In these areas, changes in coverage and/or width of peaks can be observed as a result of methylation (e.g., due to different wrapping around histones). Similarly, nucleosomal mapping of cfDNA molecules may be indirectly assessed.

The uni-parametric or multi-parametric analysis may further comprise identifying the presence of one or more somatic single nucleotide variants (SNVs) in the cell-free DNA molecules. The uni-parametric or multi-parametric analysis may further comprise identifying the presence of one or more germline single nucleotide variants (SNVs) in the cell-free DNA molecules.

One genomic parameter may be incorporated into a uni-parametric analysis. One or more genomic parameters may be incorporated into the multi-parametric analysis. The genomic parameter(s) may be chosen from: (i) tissue type, (ii) gene expression patterns, (iii) transcription factor binding site (TFBS) occupancy, (iv) methylation site, (v) set of detectable somatic mutations, (vi) level of detectable somatic mutations, (vii) set of detectable germline mutations, and (viii) level of detectable germline mutations.

Deviations from the reference uni-parametric or multi-parametric model may be detected. Such deviations may include: (i) an increase in the number of reads outside a nucleosome region, (ii) an increase in the number of reads within a nucleosome region, (iii) a broader peak distribution relative to a mappable genomic location, (iv) a shift in location of a peak, (v) identification of a new peak, (vi) a change in depth of coverage of a peak, (vii) a change in start position around a peak, and (viii) a change in fragment sizes associated with a peak. These deviations may be indicative of a nucleosomal map disruption representative of the cell-free DNA derived from the sample.

A localized genomic region is a short region of the genome that may range in length from about 2 to about 200 base pairs. Each localized genomic region may contain a pattern or cluster of significant structural variation or instability. Genome partitioning maps may be provided to identify relevant localized genomic regions. A localized genomic region may contain a pattern or cluster of significant structural variation or structural instability. A cluster is a hotspot region within a localized genomic region. The hotspot region may contain one or more significant fluctuations or peaks. A structural variation is a variation in nucleosomal positioning. A structural variation may be selected from the group consisting of: an insertion, a deletion, a translocation, a gene rearrangement, methylation status, a micro-satellite, a copy number variation, a copy number-related structural variation, or any other variation which indicates differentiation.

A genome partitioning map may be obtained by: (a) providing samples of cell-free DNA from two or more subjects in a cohort, (b) performing a multi-parametric analysis of each of the samples of cell-free DNA to generate a multi-parametric model for each of said samples, and (c) analyzing the multi-parametric models to identify one or more localized genomic regions, each of which contains a pattern or cluster of significant structural variation or instability.

A method is provided for analyzing a sample comprising cell-free DNA derived from a subject, in which sequence information representative of cell-free DNA molecules from the sample is obtained, and statistical analysis is performed on said sequence information to classify a set of one or more uni-parametric models as being associated with one or more nucleosomal occupancy profiles representing distinct cohorts.

A method is provided for analyzing a sample comprising cell-free DNA derived from a subject, in which sequence information representative of cell-free DNA molecules from the sample is obtained, and statistical analysis is performed on said sequence information to classify the multi-parametric model as being associated with one or more nucleosomal occupancy profiles representing distinct cohorts.

The statistical analysis may comprise providing one or more genome partitioning maps listing relevant genomic intervals representative of genes of interest for further analysis. The statistical analysis may further comprise selecting a set of one or more localized genomic regions based on the genome partitioning maps. The statistical analysis may further comprise analyzing one or more localized genomic regions in the set to obtain a set of one or more nucleosomal map disruptions. The statistical analysis may comprise one or more of: pattern recognition, deep learning, and unsupervised learning.

A nucleosomal map disruption is a measured value that characterizes a given localized genomic region in terms of biologically relevant information. A nucleosomal map disruption may be associated with a driver mutation chosen from the group consisting of: wild-type, somatic variant, germline variant, and DNA methylation.

One or more nucleosomal map disruptions may be used to classify the uni-parametric or multi-parametric model as being associated with one or more nucleosomal occupancy profiles representing distinct cohorts. These nucleosomal occupancy profiles may be associated with one or more assessments. An assessment may be considered as part of a therapeutic intervention (e.g., treatment options, selection of treatment, further assessment by biopsy and/or imaging).

An assessment may be selected from the group consisting of: indication, tumor type, tumor severity, tumor aggressiveness, tumor resistance to treatment, and tumor clonality. An assessment of tumor clonality may be determined from observing heterogeneity in nucleosomal map disruption across cell-free DNA molecules in a sample. An assessment of relative contributions of each of two or more clones is determined.

A disease score may be determined as a health status indicator of the subject from whom the cell-free DNA sample was obtained. This disease score may be determined as a function of one or more of: (i) one or more of the assessments, (ii) one or more healthy reference multi-parametric models associated with the disease, and (iii) one or more diseased reference multi-parametric models associated with the disease.

The genome partitioning maps may be applied toward the selection of a set of structural variations. The selection of a structural variation may be a function of one or more of: (i) one or more reference multi-parametric models associated with one or more diseases, (ii) efficiency of one or more probes targeting the structural variation, and (iii) prior information regarding portions of the genome where an expected frequency of structural variations is higher than the average expected frequency of structural variations across the genome.

The methods of analyzing one or more cell-free DNA samples may be applied toward configuring a multi-modular panel. This multi-modular panel configuration may comprise analyzing one or more of: (i) one or more somatic mutations, (ii) information of distribution of nucleosomal positions in the human genome, and (iii) prior information regarding the coverage biases in cell-free DNA molecules originating from normal tissues or cell types and from tissues or cell types containing somatic mutations. Subsequent to the above analysis, the multi-modular panel configuration may also comprise selecting for inclusion in the multi-modular panel a set comprising one or more of the following: (i) one or more structural variations, at least one of which indicates an increased likelihood of one or more diseases being present in the subject from whom the cell-free DNA sample was acquired, (ii) one or more somatic mutations, at least one of which indicates an increased likelihood of one or more diseases being present in the subject from whom the cell-free DNA sample was acquired, and (iii) one or more chromatin-centered events. The chromatin-centered events may comprise one or more of transcription start sites, promoter regions, junction sites, and intronic regions.

The methods of analyzing one or more cell-free DNA samples may be applied toward detecting or monitoring a condition. Such detecting or monitoring of a condition may comprise obtaining sequence information representative of cell-free DNA molecules from the sample; and using macroscale information (e.g., information other than base identities) pertaining to said molecules to detect or monitor said condition.

The methods of analyzing one or more cell-free DNA samples may be applied toward detecting absolute copy number (CN) related structural variations based on a multi-parametric model. The CN-related structural variations represent areas of relatively higher or lower deviation of a multi-parametric model based on genome partitioning maps. The CN-related structural variations may represent one or more nucleosomal map disruptions to determine one or more assessments, e.g., tumor burden or tumor type. With appropriate healthy reference uni-parametric or multi-parametric models and diseased reference uni-parametric or multi-parametric models, deviations in a subject's uni-parametric or multi-parametric model may be interpreted as nucleosomal map disruptions. One or more of these nucleosomal map disruptions may be combined to determine one or more assessments, e.g., tumor heterogeneity.

Panel Configurations

The fragmentome profiling technique described herein can further be used for modular panel configuration. Such modular panel configuration allows for designs of a set of probes or baits that selectively enrich regions of the genome that are relevant for nucleosomal profiling. By incorporating this "fragmentome awareness" or "nucleosomal awareness," sequence data from many individuals can be gleaned to optimize the procedure of modular panel configuration, e.g., the determination of which genomic locations to target and the optimal concentration of probes for these genomic locations.

For example, changes in chromatin structure, e.g., nucleosomal re-positioning at transcription start sites (TSSs) or disruption of topologically associated domains architecture, may play an integral role in the regulation of gene transcription and have been associated with many aspects of human health, including diseases. Therefore, comparing genome-wide chromatin accessibility between non-malignant versus malignant cohorts may allow identification of locations of instrumental epigenetic changes that accompany disease development. For example, from studies of public atlases of nucleosomal occupancy, chromatin accessibility, transcription factor binding sites, and DNase sensitivity maps, as well as direct discovery of de novo differential chromatin architectures (e.g., via whole genome sequencing (WGS)) in representative cohorts of non-malignant and malignant cases (e.g., subjects), focused footprints may be produced that are enriched in chromatin markers. Such chromatin markers may be specific to certain tissues, cell types, cell death types, and malignancy types (e.g., tumor types), and may be targeted at sufficient resolution and coverage via targeted enrichment assays.

By incorporating knowledge of both somatic variations and structural variations and instability, panels of probes, baits or primers can be configured to target specific portions of the genome ("hotspots") with known patterns or clusters of structural variation or instability. For example, statistical analysis of sequence data reveals a series of accumulated somatic events and structural variations, and thereby enables clonal evolution studies. The data analysis reveals important biological insights, including differential coverage across cohorts, patterns indicating the presence of certain subsets of tumors, foreign structural events in samples with high somatic mutation load, and differential coverage attributed from blood cells versus tumor cells.

In another example, fragmentome profiling can be applied toward generating a low-multiplexed polymerase chain reaction (PCR) panel for one or more genes. the low-multiplexed PCR panel may be generated by (a) providing one or more genome partitioning maps; (b) providing a plurality of probes that cover one or more localized genomic regions in one or more of the genome partitioning maps; and (c) selecting from the plurality of probes, one or more probes having optimal PCR performance, wherein each of said probes covers a given localized genomic region associated with each of the genes.

The assessment of optimal PCR performance is measured by maximum depth of coverage of a probe associated with each of the genes. Thus, for each gene, one or more optimal probes may be chosen for inclusion in a PCR panel.

In an example, a low-multiplexed PCR panel comprises at least 1, 2, 3, 4, 5, or 6 genes, wherein any subset of the panel can be simultaneously combined into a single multiplexed PCR assay. A low-multiplexed PCR panel may be used to perform on cell-free DNA or cell-free RNA molecules an assay selected from the group consisting of: digital PCR, droplet digital PCR, quantitative PCR, and reverse-transcription PCR. Since a low-multiplexed PCR assay does not have the ability to tile multiple probes and primers across a given gene of interest, the use of such an optimized panel will ensure the selection of an optimal set of a small number of probes for inclusion in the PCR panel.

Classification

The methods and systems herein can be applied to a classifier. The classifier can be trained or untrained. The classifier is used to identify patterns associated with a condition or state of a condition. A classifier may be implemented on a computer.

In as aspect, a classifier may determine genetic aberrations in a test subject using DNA from a cell-free sample (or cell-free DNA) obtained from the test subject. This classifier may comprise (a) an input of a set of distribution scores for each of one or more samples (or cell-free DNA) from subjects, wherein each distribution score is representative of a number of bases present in DNA from a cell-free sample (or cell-free DNA) from a subject that map to each of a plurality of positions in a genome; and (b) an output of classifications of one or more genetic aberrations.

A classifier may comprise a machine learning engine. The distribution scores may represent length of each molecule from which a base position is mapped. The distribution scores may represent counts of each molecule overlapping a base position. The distribution scores may represent counts of each molecule starting at a base position. The distribution scores may represent counts of each molecule ending at a base position.

A classifier may be used to determine genetic aberrations in a test subject using DNA from a cell-free sample (or cell-free DNA) obtained from the test subject by providing a set of distribution scores for a test subject, and generating a classification of the test subject using the classifier.

A classifier may be trained by a training set. A training set may comprise a set of distribution scores for each of a plurality of samples from subjects and a set of classifications for each of the plurality of samples. The set of distribution scores may comprise (a) a set of reference distribution scores for each of a plurality of samples from control subjects, wherein each reference distribution score is representative of a number of bases present in DNA from a cell-free sample (or cell-free DNA) from a control subject that map to each of a plurality of positions in a genome or (b) a set of phenotypic distribution scores for each of a plurality of samples from subjects having an observed phenotype, wherein each phenotypic distribution score is representative of a number of bases present in DNA from a cell-free sample (or cell-free DNA) from a subject having the observed phenotype that map to each of a plurality of positions in a genome. The set of classifications may comprise (c) a set of reference classifications for each of the plurality of samples from control subjects or (d) a set of phenotypic classifications for each of the plurality of samples from subjects having an observed phenotype.

The control subjects associated with the set of reference distribution scores or the set of reference classifications may be asymptomatic healthy individuals. The subjects having an observed phenotype associated with the set of phenotypic distribution scores or the set of phenotypic classifications may comprise (a) subjects with a tissue-specific cancer, (b) subjects with a particular stage of cancer, (c) subjects with an inflammatory condition, (d) subjects that are asymptomatic to cancer but have a tumor that will progress into cancer, or (e) subjects with cancer having positive or negative response to a particular drug or drug regimen.

The classifier may further comprise an input of a set of genetic variants at one or more loci of the genome. The set of genetic variants may comprises one or more loci of reported tumor markers (e.g., a reported tumor marker in COSMIC).

A method is provided for creating a trained classifier, comprising (a) providing a plurality of different classes, wherein each class represents a set of subjects with a shared characteristic (e.g., from one or more cohorts); (b) providing a uni-parametric or multi-parametric model representative of the cell-free DNA molecules from each of a plurality of samples belonging to each of the classes, thereby providing a training data set; and (c) training a learning algorithm on the training data set to create one or more trained classifiers, wherein each trained classifier classifies a test sample into one or more of the plurality of classes.

As an example, a trained classifier may use a learning algorithm selected from the group consisting of: a random forest, a neural network, a support vector machine, and a linear classifier. Each of the plurality of different classes may be selected from the group consisting of: healthy, breast cancer, colon cancer, lung cancer, pancreatic cancer, prostate cancer, ovarian cancer, melanoma, and liver cancer.

A trained classifier may be applied to a method of classifying a sample from a subject. This method of classifying may comprise: (a) providing a set of one or more uni-parametric models representative of the cell-free DNA molecules from a test sample from the subject; and (b) classifying the test sample using a trained classifier. After the test sample is classified into one or more classes, performing a therapeutic intervention on the subject based on the classification of the sample.

A trained classifier may be applied to a method of classifying a sample from a subject. This method of classifying may comprise: (a) providing a multi-parametric model representative of the cell-free DNA molecules from a test sample from the subject; and (b) classifying the test sample using a trained classifier. After the test sample is classified into one or more classes, performing a therapeutic intervention on the subject based on the classification of the sample.

Figure 8:
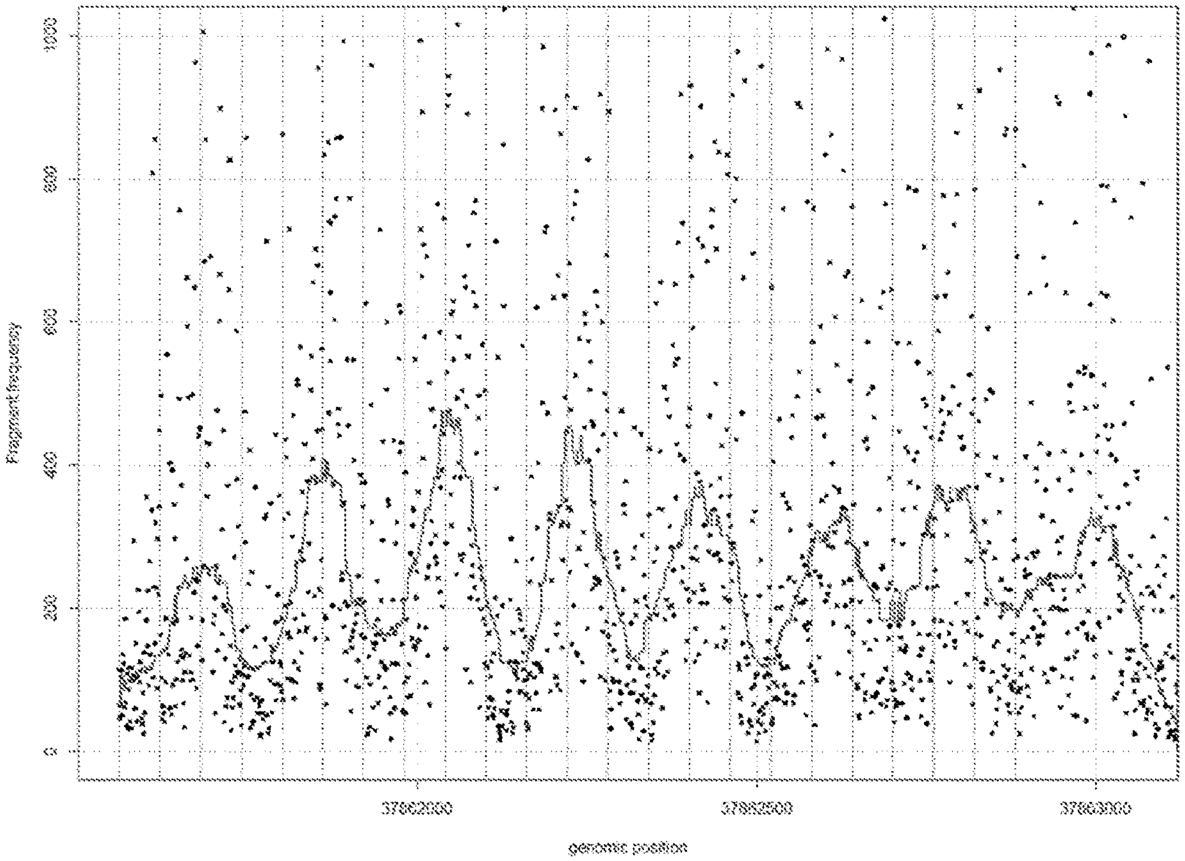
FIG. 8 illustrates an aspect of a multi-parametric model, in particular plots of the fragment frequency at each genomic position within a range of the genome.
Figure 9:
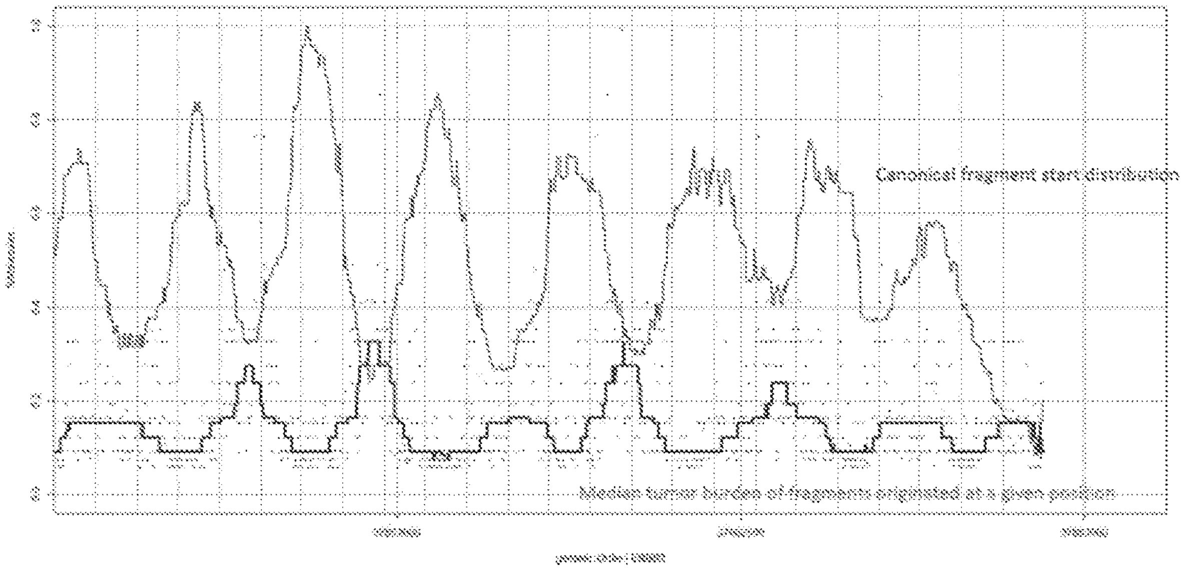
FIG. 9 illustrates an aspect of a multi-parametric model, in particular plots of the fragment frequency at each genomic position within a range of the genome.

FIGS. 8 and 9 each illustrate one aspect that may be incorporated into a multi-parametric model, in particular plots of the fragment frequency at each genomic position within a range of the genome. In each figure, the fragment frequency fluctuates with genomic position as a result of differential nucleosomal positioning. In FIG. 8, a semi-periodic line shows the average fragment frequency (y-axis) across the genomic positions (x-axis), which illustrates a varying fragmentome signal as a result of differential nucleosomal occupancy. In FIG. 9, two semi-periodic lines show the canonical fragment start distribution (y-axis) and the median tumor burden of fragments originated at a given position (y-axis), respectively, across the genomic positions (x-axis), which illustrate both a varying fragmentome signal as a result of differential nucleosomal occupancy and a higher median tumor burden of fragments originating at a given position at positions of lower canonical fragment start distribution.

Figure 10:
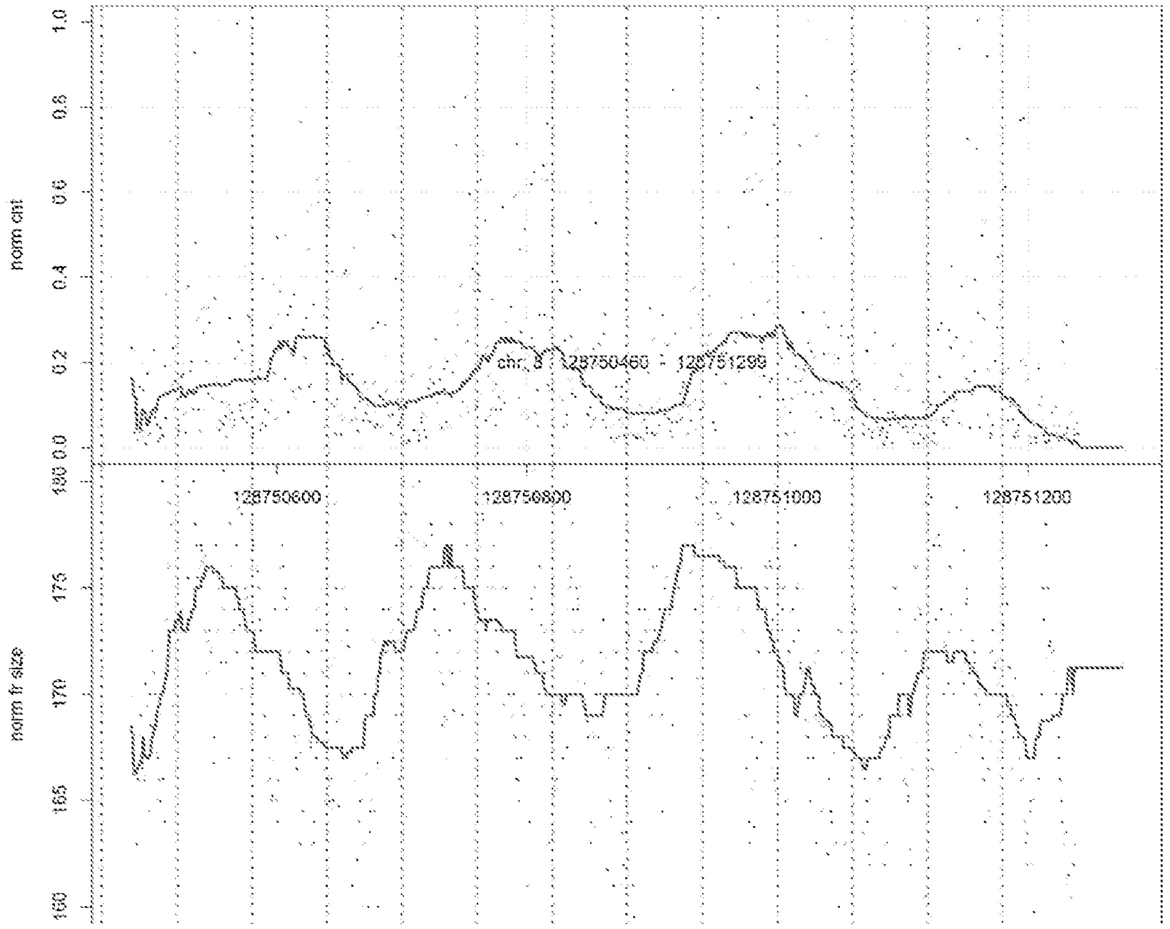
FIG. 10 illustrates two aspects of a multi-parametric model, in particular plots of the normalized counts of molecules and the normalized fragment size (i.e., length) at each genomic position within a range of the genome.
Figure 11:
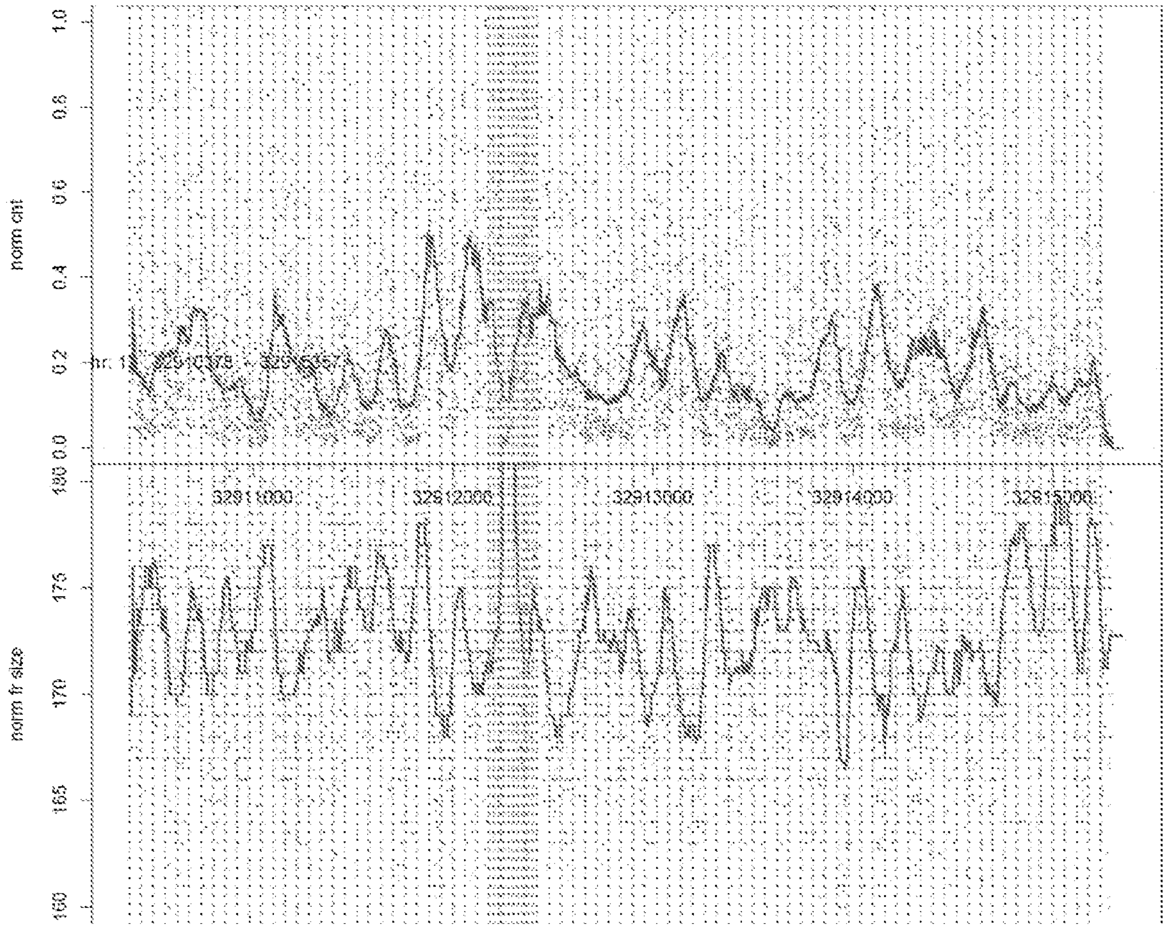
FIG. 11 illustrates two aspects of a multi-parametric model, in particular plots of the normalized counts of molecules and the normalized fragment size (i.e., length) at each genomic position within a range of the genome.

FIGS. 10 and 11 illustrate two aspects of a multi-parametric model, in particular plots of the normalized counts of molecules (top panel) and the normalized fragment size (i.e., length; bottom panel) at each genomic position within a range of the genome. In each figure, both the normalized counts of molecules and the normalized fragment size fluctuate with genomic position as a result of differential nucleosomal positioning.

Figure 12:
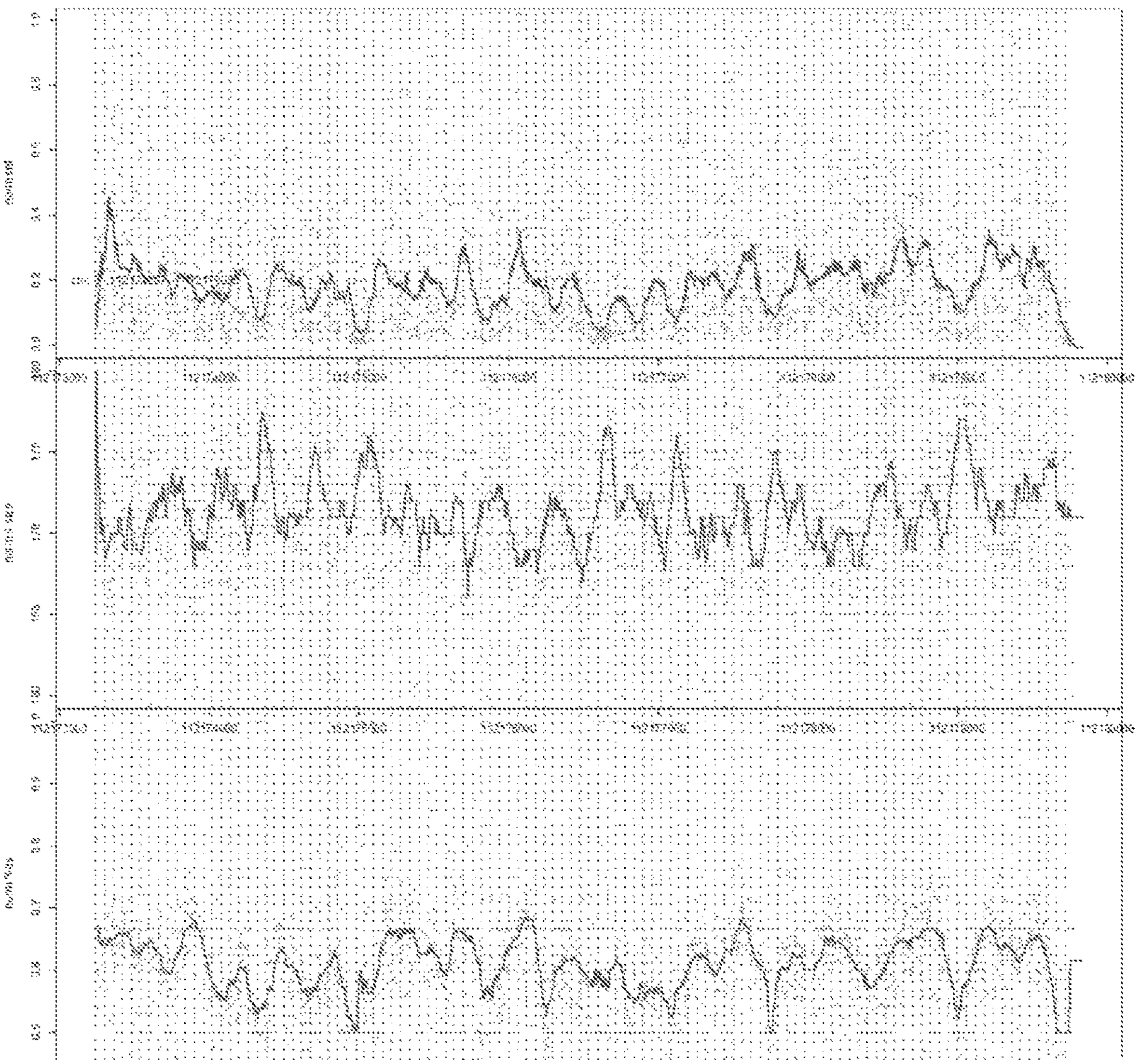
FIG. 12 illustrates three aspects of a multi-parametric model, in particular the normalized counts of molecules, the normalized fragment size (i.e., length), and the percentage of normalized double-strands at each genomic position within a range of the genome.

FIG. 12 illustrates three aspects of a multi-parametric model, in particular the normalized counts of molecules, the normalized fragment size (i.e., length), and the percentage of normalized double-strands at each genomic position within a range of the genome. All three aspects of the multi-parametric model fluctuate with genomic position as a result of differential nucleosomal positioning. In particular, this fluctuation shows some periodicity in the multi-parametric model. This periodicity is typically about 10.5 base pairs.

Figure 13:
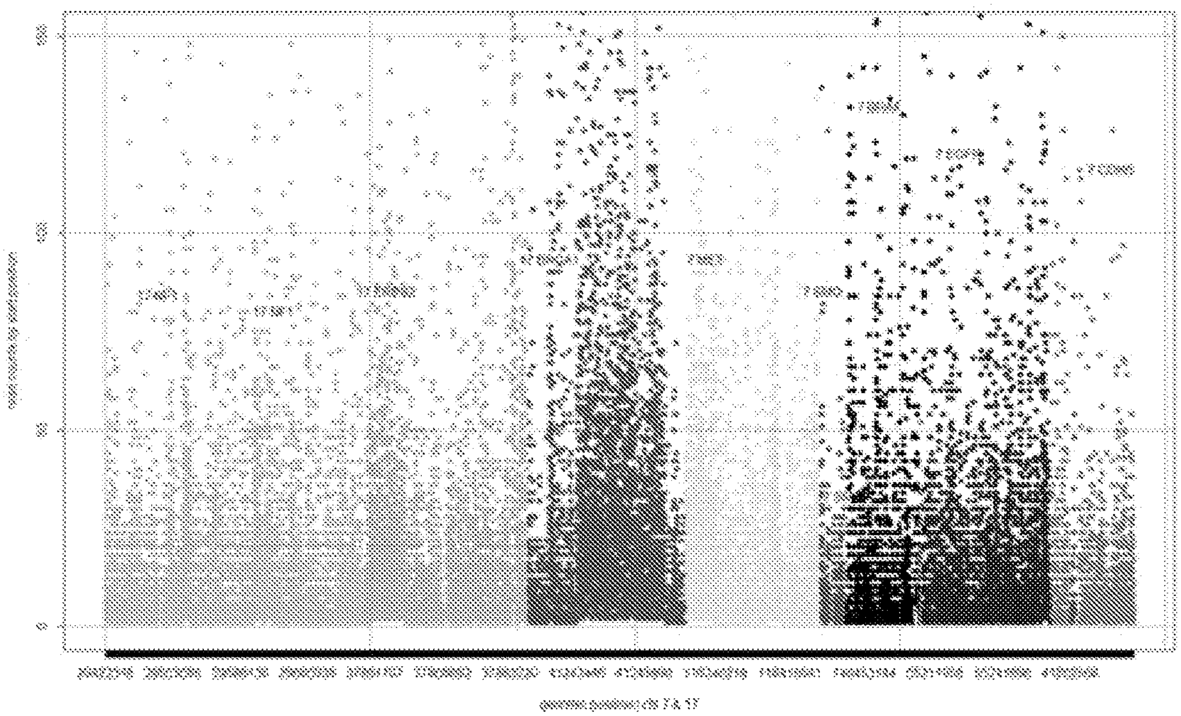
FIG. 13 illustrates one aspect of a multi-parametric model, in particular the read counts (y-axis) at each genomic position (x-axis) within a range of the genome.

FIG. 13 illustrates one aspect of a multi-parametric model, in particular the read counts (y-axis) at each genomic position (x-axis) within a range of the genome. This range of the genome corresponds to several tumor-relevant genes, including NF1, ERBB2, BRCA1, MET, SMO, BRAF, EGFR, and COK6.

Figure 14:
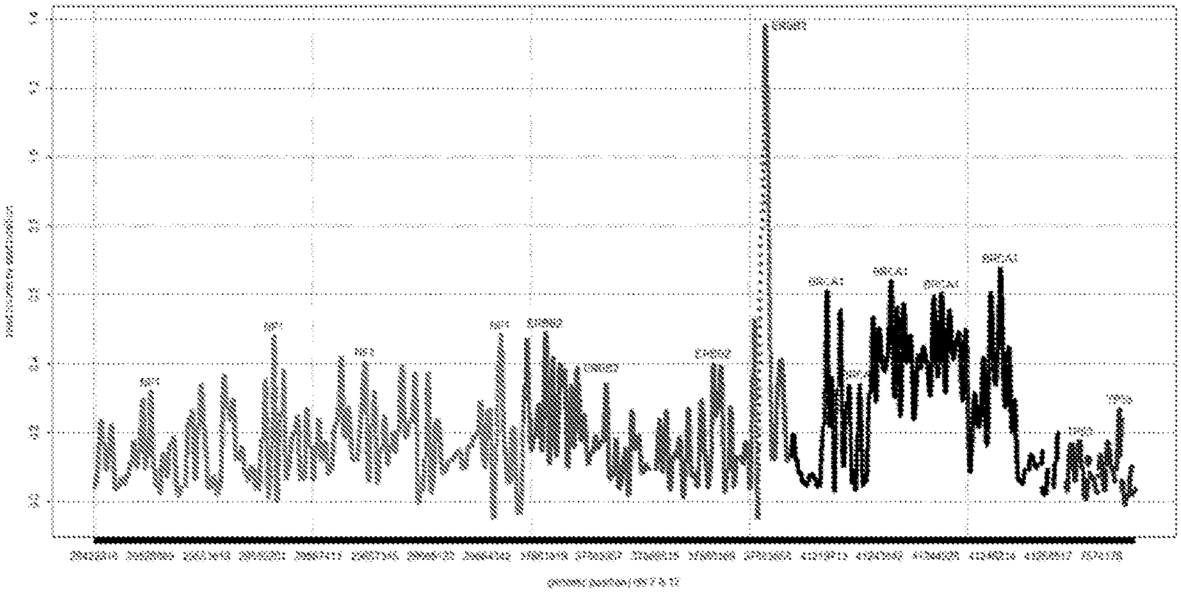
FIG. 14 illustrates an example of a mathematical transform that can be performed as part of the multi-parametric analysis to generate a multi-parametric model.

FIG. 14 illustrates an example of a mathematical transform that can be performed as part of the multi-parametric analysis to generate a multi-parametric model. In particular, a Fast Fourier Transform (FFT) is applied to generate a plot of read counts by start position at each genomic position within a range of the genome. This range of the genome corresponds to several tumor-relevant genes, including NF1, ERBB2, BRCA1, and TP53. As shown, in particular, the ERBB2 gene exhibits a read count value that is significantly higher (about twice or more) than the other genes indicated, which indicates that an ERBB2 mutation is likely present.

Figure 15:
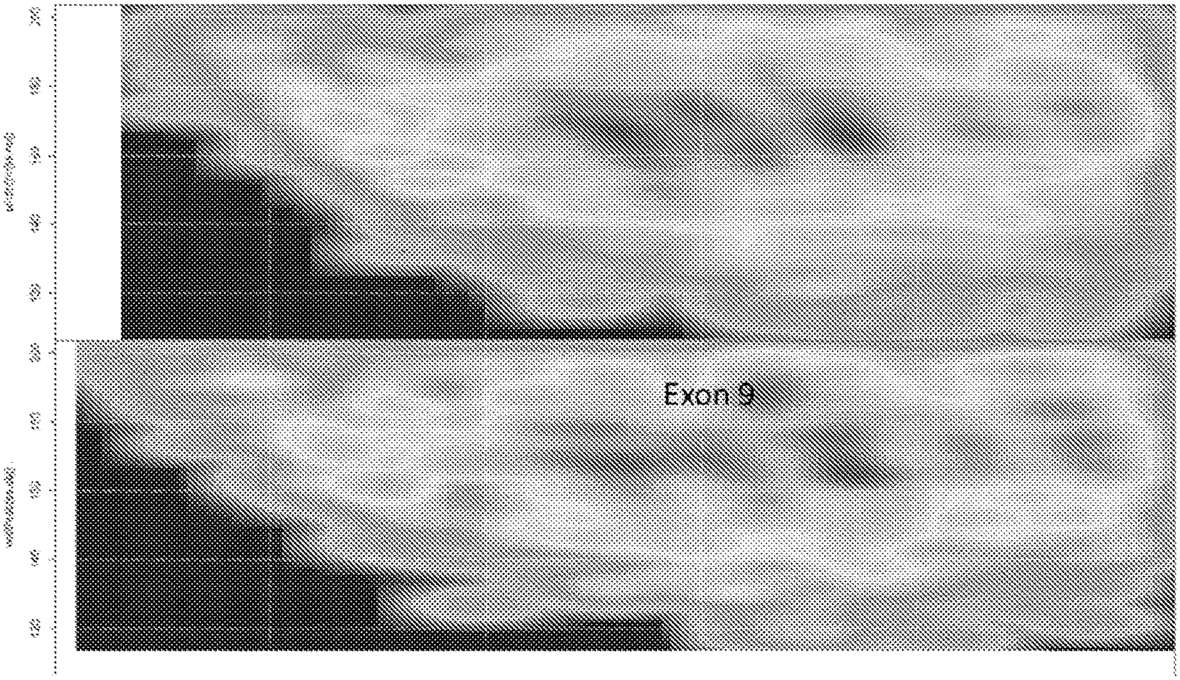
FIG. 15 illustrates an example of two multi-parametric models of two different subjects in a given region of a genome.

FIG. 15 illustrates an example of two multi-parametric models of two different subjects in a given region of a genome. In particular, this region of the genome corresponds to a tumor-relevant gene, TP53. From the multi-parametric model (in this case, a heat map) corresponding to a subject with a tumor (bottom panel), deviations can be seen relative to the subject without tumor (top panel), especially near the area marked by Exon 9. Such deviations include a less smooth topography of the heat map and the presence of more variable regions (e.g., peaks).

Figure 16:
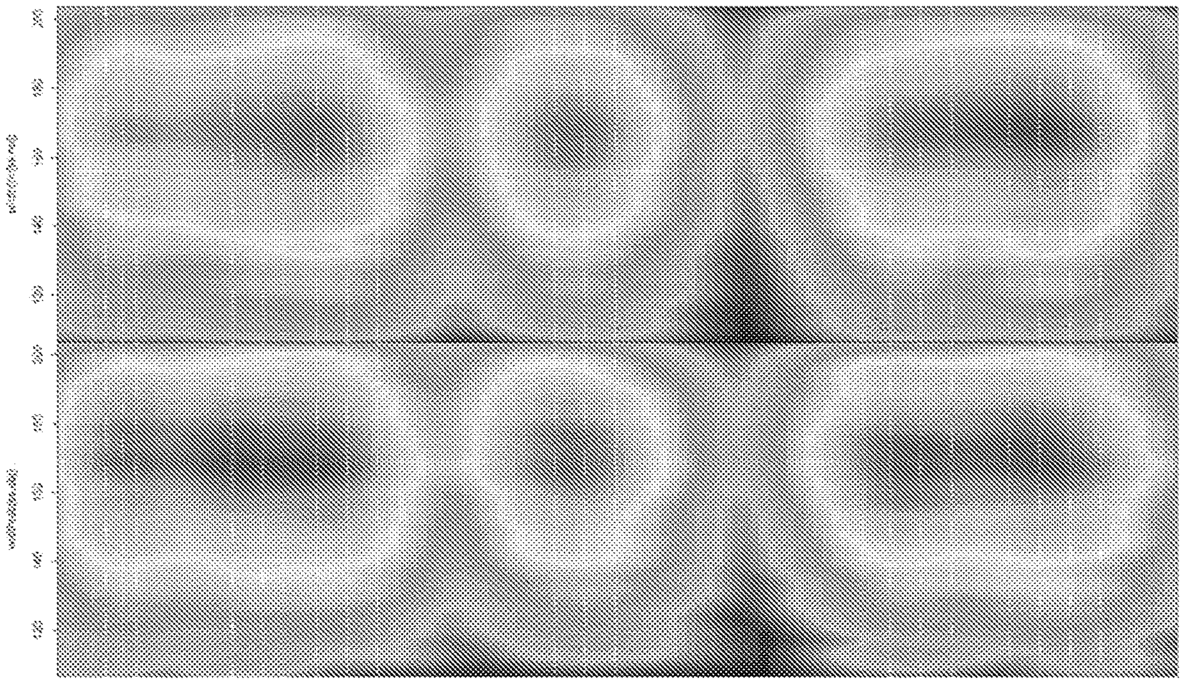
FIG. 16 illustrates an example of two multi-parametric models of two different subjects in a given region of a genome.

FIG. 16 illustrates an example of two multi-parametric models of two different subjects in a given region of a genome. In particular, this region of the genome corresponds to a tumor-relevant gene, NF1. TP53. From the multi-parametric model (in this case, a heat map) corresponding to a subject with a tumor (bottom panel), deviations can be seen relative to the subject without tumor (top panel). Such deviations include a less smooth topography of the heat map and the presence of more variable regions (e.g., peaks).

Figure 17:
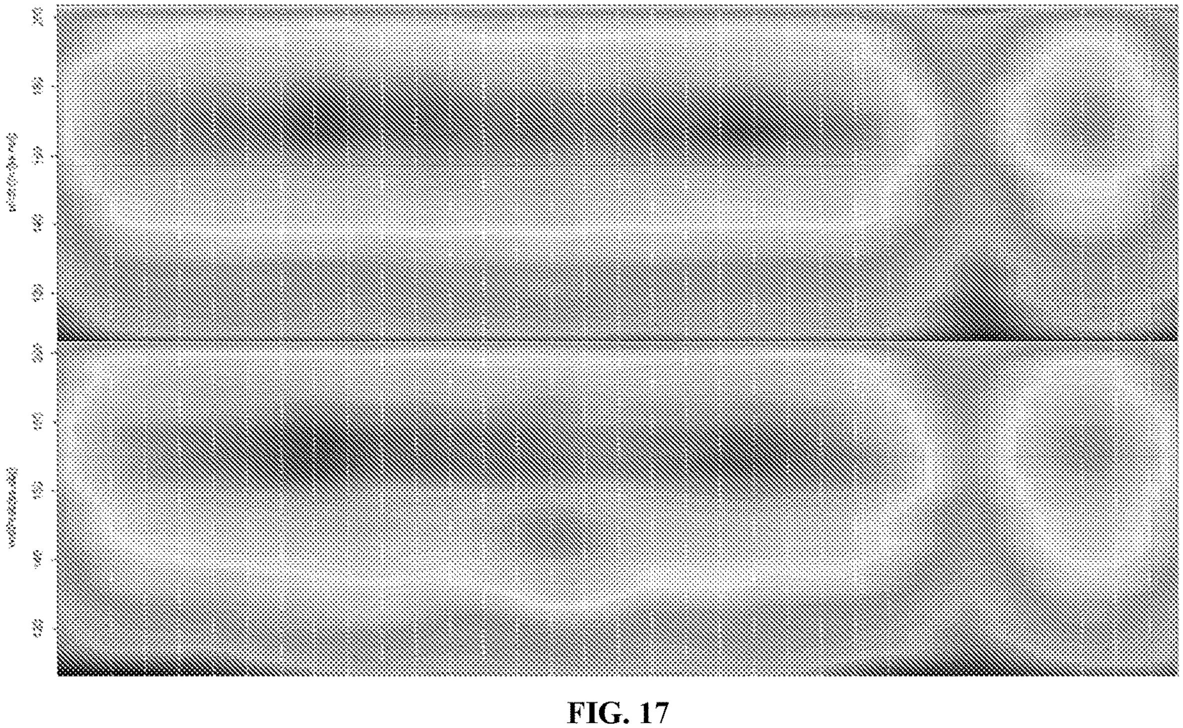
FIG. 17 illustrates an example of two multi-parametric models of two different subjects in a given region of a genome.

FIG. 17 illustrates an example of two multi-parametric models of two different subjects in a given region of a genome. In particular, this region of the genome corresponds to a tumor-relevant gene, ERBB2. From the multi-parametric model (in this case, a heat map) corresponding to a subject with a tumor (bottom panel), deviations can be seen relative to the subject without tumor (top panel). Such deviations include a less smooth topography of the heat map and the presence of more variable regions (e.g., peaks).

Figure 18:
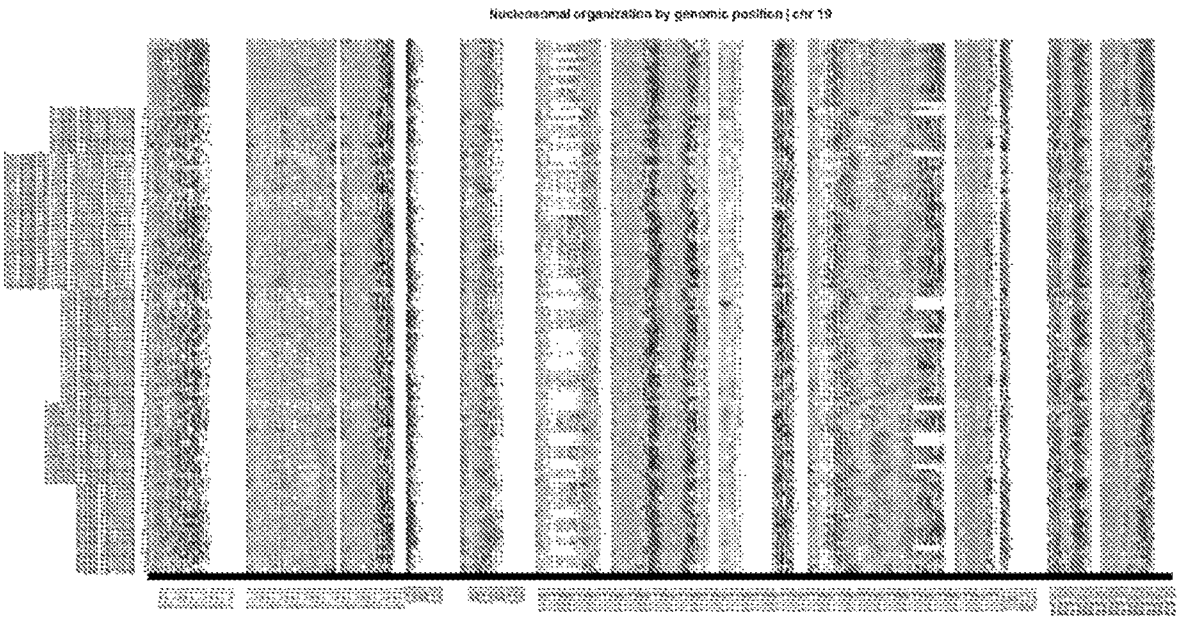
FIG. 18 illustrates an example of nucleosomal organization versus genomic position in a given region of a genome.
Figure 19:
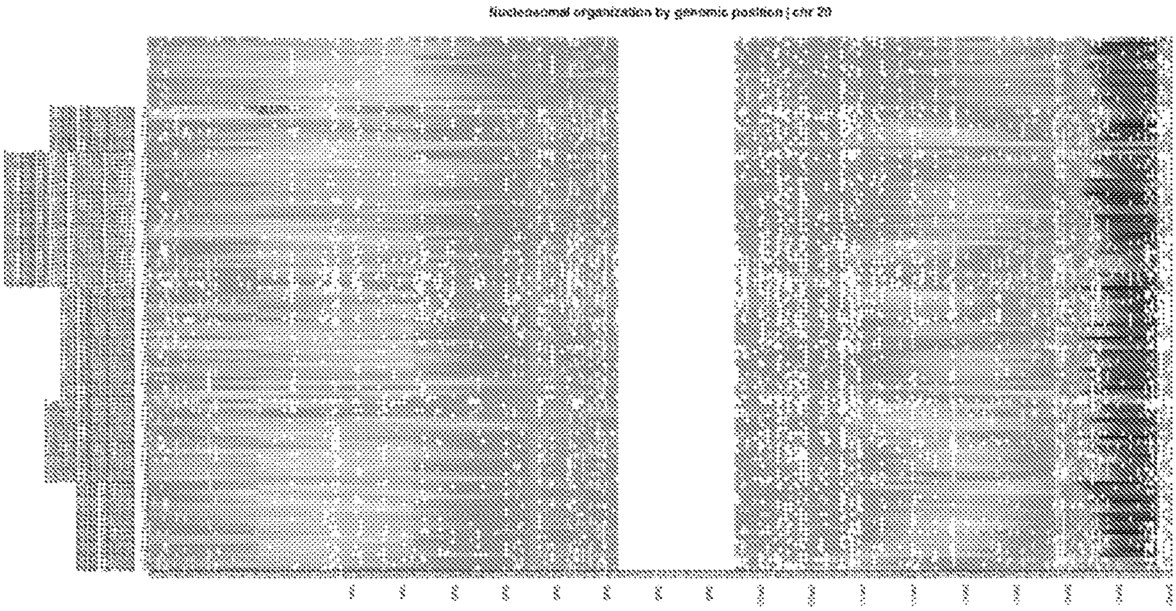
FIG. 19 illustrates an example of nucleosomal organization versus genomic position in a given region of a genome.

FIGS. 18 and 19 illustrate examples of nucleosomal organization versus genomic position in a given region of a genome. In particular, each figure illustrates the nucleosomal organization (coverage denoted by shaded color) versus genomic position (x-axis) in a different human chromosome (Chromosome 19 in FIG. 18 and Chromosome 20 in FIG. 19), measured across different subjects (y-axis). FIGS. 18 and 19 illustrate that similar clusters of fragmentome signals can be observed across different subjects in a cohort, regardless of the base identities in these genomic regions.

Figure 20:
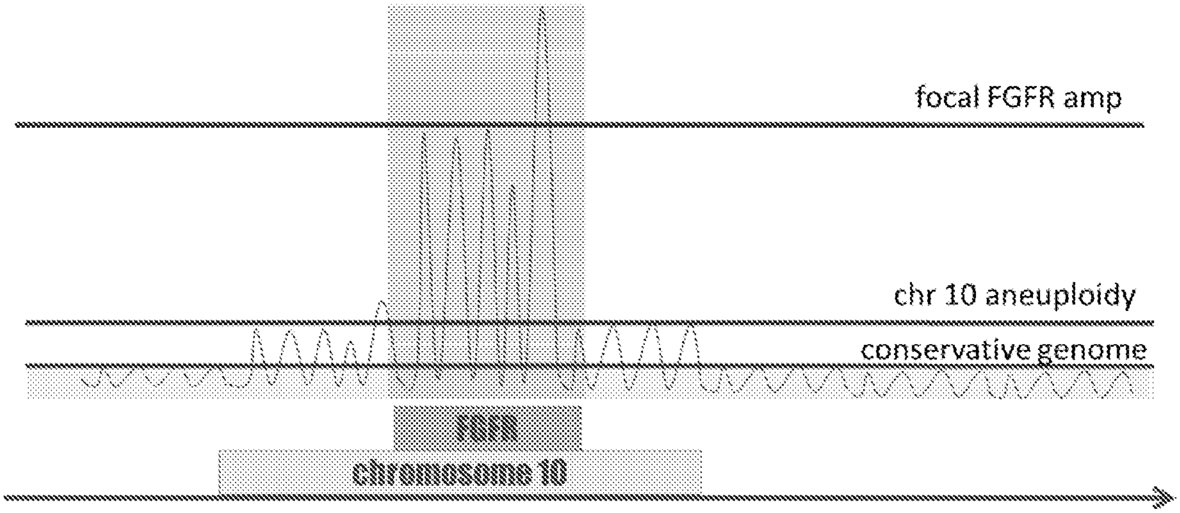
FIG. 20 illustrates an example of the process for determining absolute Copy Number (CN).

FIG. 20 illustrates an example of the process for determining absolute Copy Number (CN). First, locate nucleosome locations and match them to expected in normal cohort. Then, for every nucleosome window in FGFR, determine a collection of ultraconservative non-chr10 nucleosome sites and determine a collection of ultraconservative chr10 nucleosome sites. Finally, integrate over position vs. insert size density of FGFR nucleosome site.

Figure 21A:
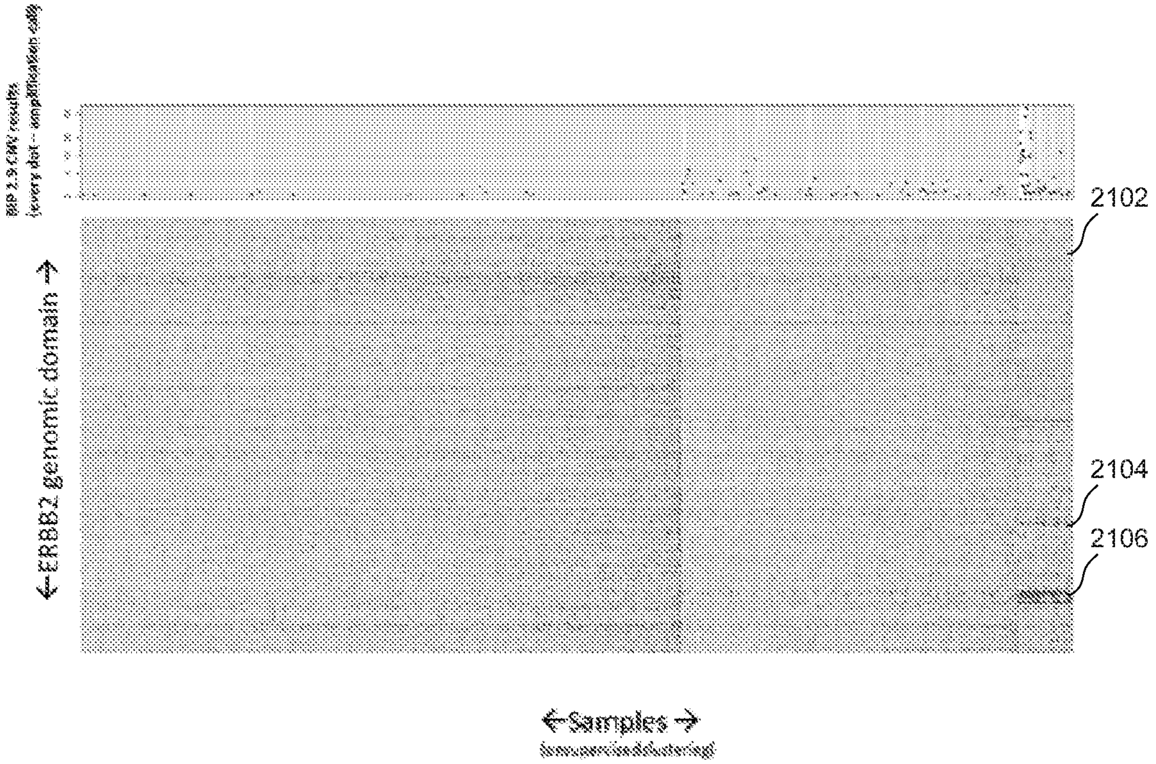
FIGS. 21A and 21B illustrate an example of using fragmentome profiling to infer activation of copy number amplified genes by whole-sequencing of plasma DNA.
Figure 21B:
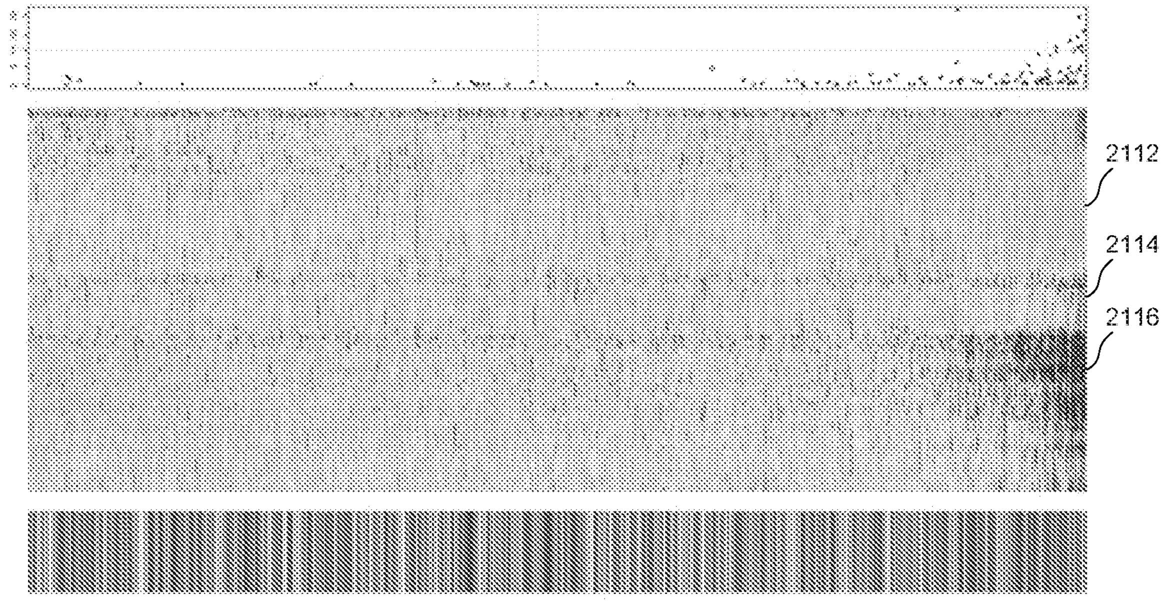

FIGS. 21A and 21B illustrate an example of using fragmentome profiling to infer activation of copy number amplified genes by whole-sequencing of plasma DNA. FIG. 21A shows a plot of normalized dinucleosomal-to-mononucleosomal count ratio in ERBB2 in 2,076 clinical samples. By visual inspection of this heat map, regions of high amplification activity (e.g., shown in yellow color 2104 and red color 2106) can be observed against a background of normal to low amplification activity (e.g., shown in green color 2102). FIG. 21B shows a zoomed-in portion of the right side of the plot of FIG. 21A, showing a cluster enriched in high-amplitude CNV calls (e.g., as shown in yellow color 2114 and red color 2116) against a background of green or blue color 2112. The bottom panel of FIG. 21B shows genomic regions that have been clustered together by similar fragmentome signals (e.g., as a result of contiguous portion of genomic regions corresponding to a common gene locus).

For each clinical sample, only ERBB2 fragments (e.g., cfDNA fragments mapping to the ERBB2 gene) were excised and subjected to fragmentome profiling. ERBB2 is well known as a marker for certain types of cancer, such as breast cancer and gastric cancer, and as a marker for resistance to treatment in subjects with cancer. For each clinical sample, dinucleosomal-to-mononucleosomal count ratio was determined across an ERBB2 genomic domain (e.g., genomic region) by (1) counting a number of fragments with dinucleosomal protection (e.g., a fragment size of at least 240 base pairs ("bp")), (2) counting a number of fragments with mononucleosomal protection (e.g., a fragment size of less than 240 base pairs ("bp")), (3) taking a ratio of (1) to (2), and (4) normalizing the ratio to the sample median (e.g., median such ratio value across the sample). Then, for each clinical sample, the sample's di-nucleosomal-to-mononucleosomal count ratio was plotted with CNV measurements associated with that sample (e.g., with every amplification call shown as a purple dot; top panel).

Unsupervised clustering of this data plot across 2,076 clinical samples revealed the presence of 3 clusters of high amplification activity (as indicated by the highest fragmentome signal expressed by read counts) (e.g., shown in yellow color 2104 and red color 2106) against a background of normal to low amplification activity (e.g., shown in green color 2102), with one on the right being most pronounced to the eye. This cluster is enriched in high-amplitude CNV calls, while others are smeared across a cluster in the middle and less so across a cluster on the right. The clusters may be interpreted as an indication that copy number amplified genes (e.g., genes associated with ERBB2) have been activated for the clinical samples associated with the visible clusters (e.g., in red and yellow colors). Thus, a fragmentome profile (e.g., in ERBB2) can be correlated to amplification status. Such observations may be made even for genomic regions without associated high-amplitude CNV calls (perhaps because of a low sensitivity of circulating tumor DNA (e.g., ctDNA) which enables only limited detection). These observations may be interpreted as indicating a higher likelihood that those genomic regions are actively transcribing a fragmentome-profiled gene (e.g., ERBB2). Such fragmentome profiling can be incorporated into existing CNV detection methods (e.g., by performing a liquid biopsy assay) to increase sensitivity and specificity. Similar analyses may be performed across a plurality of genes to observe relatively high and low activation of copy number amplification among the plurality of genes.

The results of FIGS. 21A and 21B show that cfDNA fragments may reveal insight into a tumor microenvironment of cancer cells by performing fragmentome profiling comprising analysis of fragment sizes and fragment positions. In this case, activation of copy number amplified genes (e.g., ERBB2) in actively shed from cells in a tumor microenvironment can be observed as an ERBB2 dinucleosomal protection signature independently from performing high-amplitude CNV calls. This approach may be advantageous over existing CNV detection and calling approaches because the latter are very difficult to sensitively detect in circulating tumor DNA (e.g., ctDNA) given low allele fractions typically in circulation. Such fragmentome approaches may also be appropriate to measure and predict the presence of other genetic variants such as SNVs, indels, and fusions, especially when such genetic variants do not result in an observable phenotype difference. Fragmentome profiling across subjects in a cohort with a shared disease, e.g., for conjunction of location, fragment length, or distance function in different dimensions (fragment length, location) relative to normal samples may reveal molecular subtypes within the cohort (e.g., different molecular subtypes of lung cancer within a cohort of lung cancer patients), thereby stratifying the subjects in the cohort.

Assays for Differences in Nucleosomal Fragment Lengths

Disclosed herein is a method for processing a biological sample of a subject, comprising (a) obtaining said biological sample of said subject, wherein said biological sample comprises deoxyribonucleic acid (DNA) fragments; (b) assaying said biological sample to generate a signal(s) indicative of a presence or absence of DNA fragments with (i) dinucleosomal protection associated with a genetic locus from one or more genetic loci, and (ii) mononucleosomal protection associated with the genetic locus; and (c) using said signal(s) to generate an output indicative of said presence or absence of DNA fragments with (i) dinucleosomal protection associated with a genetic locus from one or more genetic loci, and (ii) mononucleosomal protection associated with the genetic locus.

The method may involve enriching the biological sample for DNA fragments for a set of one or more genetic loci.

Also disclosed herein is a method for analyzing a biological sample that comprises cell-free DNA fragments derived from a subject, wherein the method comprises detecting DNA fragments from the same genetic locus which correspond to each of mononucleosomal protection and dinucleosomal protection.

Also disclosed herein is a method for analyzing a biological sample of a subject, wherein the method comprises:

(i) sequencing cfDNA fragments in the sample, to provide DNA sequences; (ii) mapping DNA sequences obtained in (i) to one or more genomic regions in a reference genome for the subject's species; and (iii) for one or more genomic regions having a mapped DNA sequence, calculating the number of sequences which correspond to mononucleosomes and the number of sequences which correspond to dinucleosomes. The numbers of mono- and di-nucleosomal sequences obtained in (iii) can be compared.

Thus, in general terms, cfDNA fragments corresponding to mononucleosomal and dinucleosomal protection of the same genetic locus (or loci) are separately assayed. As shown herein, changes in the measured levels of these fragments can reveal a change in biological state within the subject e.g., FIG. 27B shows an increase in dinucleosomal fragments in breast cancer patient samples with a high ERBB2 copy number. The methods may therefore include an additional step of using the detected or calculated signal (e.g., using a classifier, as discussed elsewhere herein) to assess the biological state of the subject from whom the sample was taken (e.g., to diagnose a disease). In particular, a change in the quantity of mono- or di-nucleosomal fragments can be used to assess the subject's biological state.

The fragments can be assayed in various ways e.g., by sequencing cfDNA fragments as discussed elsewhere herein, or by separating cfDNA fragments by size (e.g., on an agarose gel) and quantifying them.

These methods can consider the quantitative ratio of mononucleosomal and dinucleosomal fragments seen at the locus (e.g., the ratio can change as a biological state changes), the quantity of fragments seen at the locus (e.g., levels of both types of fragment can increase, even though the ratio stays the same), or the emergence or disappearance of fragments (e.g., dinucleosomal fragments may be undetectable in one biological state, but detectable in another state). Each of these signals can be considered in the method.

The methods can focus on a particular genetic locus (or loci) of interest e.g., which are known to exhibit a change in mononucleosomal and/or dinucleosomal signal according to biological state. In other embodiments, however, the methods may detect a signal which can then be correlated with a change in biological state. For instance, cfDNA can be sequenced and the sequences can be mapped onto a reference genome, as discussed elsewhere herein. In some embodiments, for loci where a change in mononucleosomal and/or dinucleosomal signal has already been correlated with a difference in biological state (e.g., diseased vs. non-diseased, or mutant vs. wild-type, or low vs. high copy number, etc.), the signal at these loci can be assessed (e.g., using a classifier, as discussed elsewhere herein). In other embodiments, the mono-/di-nucleosomal signal(s) at one or more loci can be compared to the signal(s) at the same loci in a sample taken from a subject having a different biological state, and any differences can be assessed (e.g., using samples from further subjects) to see if they correlate with that difference in biological state or to construct a classifier, as discussed elsewhere herein.

A method may therefore include a step of comparing the quantity of mono-/di-nucleosomal fragments with values obtained from a reference sample. Such comparisons can use classifiers as described elsewhere herein.

A locus considered with these methods may generally be within a single gene or a promoter region of a single gene.

In addition to considering dinucleosomal fragments, these methods can additionally (or instead) consider other oligonucleosomal fragments (tri-, tetra-, etc.) although, as shown in FIG. 1E, such fragments are less abundant and so are not so readily detected. Oligonucleosomal fragments (di-, tri-, etc.) can be considered individually or collectively.

Assays for mono- and oligonucleosomal DNA fragments are known in the art. For instance, the Cell Death Detection ELISA$^{PLUS}$ product is commercially available, and has been applied to cfDNA in serum (Holdenrieder et al., 2005), but it does not distinguish between the length of the DNA fragments or between fragments at different loci.

Computer Systems

Figure 22:
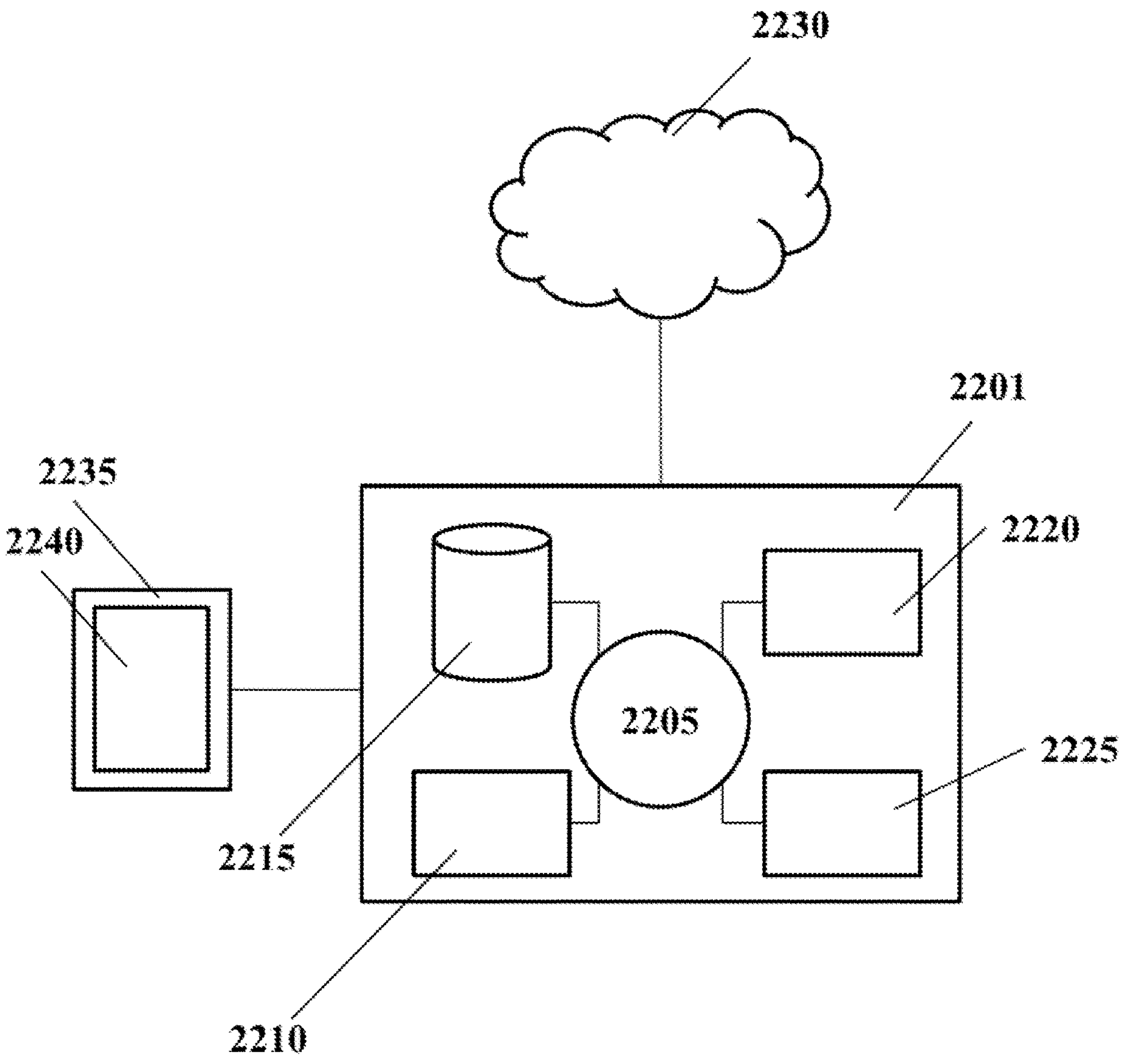
FIG. 22 shows a computer system that is programmed or otherwise configured to implement methods provided herein.

The present disclosure provides computer systems that are programmed to implement methods of the disclosure. FIG. 22 shows a computer system 2201 that is programmed or otherwise configured to analyze a sample comprising cell-free nucleic acid derived from a subject. The computer system 2201 can regulate various aspects of methods of the present disclosure. The computer system 2201 can be an electronic device of a user or a computer system that is remotely located with respect to the electronic device. The electronic device can be a mobile electronic device.

The computer system 2201 includes a central processing unit (CPU, also "processor" and "computer processor" herein) 2205, which can be a single core or multi core processor, or a plurality of processors for parallel processing. The computer system 2201 also includes memory or memory location 2210 (e.g., random-access memory, read-only memory, flash memory), electronic storage unit 2215 (e.g., hard disk), communication interface 2220 (e.g., network adapter) for communicating with one or more other systems, and peripheral devices 2225, such as cache, other memory, data storage and/or electronic display adapters. The memory 2210, storage unit 2215, interface 2220 and peripheral devices 2225 are in communication with the CPU 2205 through a communication bus (solid lines), such as a motherboard. The storage unit 2215 can be a data storage unit (or data repository) for storing data. The computer system 2201 can be operatively coupled to a computer network ("network") 2230 with the aid of the communication interface 2220. The network 2230 can be the Internet, an internet and/or extranet, or an intranet and/or extranet that is in communication with the Internet. The network 2230 in some cases is a telecommunication and/or data network. The network 2230 can include one or more computer servers, which can enable distributed computing, such as cloud computing. The network 2230, in some cases with the aid of the computer system 2201, can implement a peer-to-peer network, which may enable devices coupled to the computer system 2201 to behave as a client or a server.

The CPU 2205 can execute a sequence of machine-readable instructions, which can be embodied in a program or software. The instructions may be stored in a memory location, such as the memory 2210. The instructions can be directed to the CPU 2205, which can subsequently program or otherwise configure the CPU 2205 to implement methods of the present disclosure. Examples of operations performed by the CPU 2205 can include fetch, decode, execute, and writeback.

The CPU 2205 can be part of a circuit, such as an integrated circuit. One or more other components of the system 2201 can be included in the circuit. In some cases, the circuit is an application specific integrated circuit (ASIC).

The storage unit 2215 can store files, such as drivers, libraries and saved programs. The storage unit 2215 can store user data, e.g., user preferences and user programs. The computer system 2201 in some cases can include one or more additional data storage units that are external to the computer system 2201, such as located on a remote server that is in communication with the computer system 2201 through an intranet or the Internet.

The computer system 2201 can communicate with one or more remote computer systems through the network 2230. For instance, the computer system 2201 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2201 via the network 2230.

Methods as described herein can be implemented by way of machine (e.g., computer processor) executable code stored on an electronic storage location of the computer system 2201, such as, for example, on the memory 2210 or electronic storage unit 2215. The machine executable or machine readable code can be provided in the form of software. During use, the code can be executed by the processor 2205. In some cases, the code can be retrieved from the storage unit 2215 and stored on the memory 2210 for ready access by the processor 2205. In some situations, the electronic storage unit 2215 can be precluded, and machine-executable instructions are stored on memory 2210.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2201 can include or be in communication with an electronic display 2235 that comprises a user interface (UI) 2240 for providing, for example, information that is relevant to an analysis of a sample comprising cell-free nucleic acid derived from a subject. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2205.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Example 1: Cell-Free DNA Fragmentation Patterns Reveal Changes Associated with Somatic Mutations in the Primary Tumors and Improve Sensitivity and Specificity of Somatic Variant Detection Cell-free DNA (cfDNA) isolated from circulating blood plasma comprises DNA fragments surviving clearance of dying cells and bloodstream trafficking. In cancer, these fragments carry a footprint of tumor somatic variation as well as their microenvironment, enabling non-invasive plasma-based tumor genotyping in clinical practice. However, the fraction of cancer-derived DNA is typically low, challenging accurate detection in early stages and prompting the search for orthogonal somatic variant-free patterns associated with cancerous state. Since genomic distribution of cfDNA fragments has been shown to reflect nucleosomal occupancy in hematopoietic cells, an experiment was performed (a) to observe heterogeneous patterns of cfDNA positioning in cancer in association with distinct mutations in patient tumors and (b) to integrate cfDNA positioning into existing analysis approaches may allow increased sensitivity and specificity of detection.

Distributions of cfDNA fragment length and position, and associated somatic genomic profiles of over 15 thousand patients with advanced-stage clinical cancer were determined by a highly accurate, deep-coverage (15,000×) ctDNA NGS test targeting 70 genes. An integrative analysis of variant-free fragmentome profiling was performed, and the fragmentome profile was tested for association with detected somatic alterations using statistical methods. Distinct classes of fragmentomic subtypes (e.g., sub-types with differential fragmentome profiles revealed by visual observation, clustering, or other approaches) were observed to be significantly enriched in samples with well-characterized driver alterations and genomic molecular subtypes. An independent cohort of samples with known HER2 immunohistochemistry status was interrogated to confirm discovered association between patterns of cfDNA positioning and HER2 amplifications.

Overall, fragmentome profiling revealed an ERBB2 (e.g., HER2) amplification signature that was significantly associated with the HER2 immunohistochemistry (IHC) status of tumors, resulting in a 42% increase in sensitivity of HER2 amplification detection and a 7% increase in specificity of HER2 amplification detection. Observed lung adenocarcinoma fragmentomic subtypes co-occurred with mutually exclusive genomic alterations and previously described intrinsic molecular subtypes of lung cancer. Together, these results suggest that integrative analysis of cfDNA fragmentation landscapes may aid further development of cfDNA based biomarkers for a variety of human conditions. Thus, fragmentome profiling may enable classification of cancer cfDNA and may provide independent evidence for observed somatic variation and underlying tumor microenvironment, leading to higher sensitivity and accuracy of variant detection. This suggests a path toward integrated detection of clinically-relevant classes with distinct pathogenesis of cancer subtypes and therapy selection.

Example 2: Cell-Free DNA Fragmentation Patterns (Fragmentome Profiling or "Fragmentomics" Analysis) Reveal Changes Associated with Tumor-Associated Somatic Mutations Cell-free DNA (cfDNA) isolated from circulating blood plasma comprises DNA fragments surviving clearance of dying cells and bloodstream trafficking. In cancer, these fragments carry a footprint of tumor somatic variation as well as their microenvironment, enabling non-invasive plasma-based tumor genotyping in clinical practice. However, the fraction of cancer-derived DNA is typically low, challenging accurate detection in early stages and prompting the search for orthogonal somatic variant-free patterns associated with cancerous state. Because genomic distribution of cfDNA fragments has been shown to reflect nucleosomal occupancy in hematopoietic cells, an experiment was performed (a) to observe heterogeneous patterns of cfDNA positioning in cancer in association with distinct mutations in patient tumors and (b) to integrate cfDNA positioning into existing analysis approaches may allow increased sensitivity and specificity of detection.

Distributions of cfDNA fragment length and position, and associated somatic genomic profiles of over 15 thousand patients with advanced-stage clinical cancer were determined by a highly accurate, deep-coverage (>15,000×) ctDNA NGS test targeting 70 genes. An integrative analysis of variant-free fragmentome profiling ("fragmentomics" analysis) was performed, and the fragmentome profile was tested for association with detected somatic alterations using statistical methods. Distinct classes of fragmentomic sub-types (e.g., sub-types with differential fragmentome profiles revealed by visual observation, clustering, or other approaches) were observed to be significantly enriched in samples with well-characterized driver alterations and genomic molecular subtypes.

Figure 23:
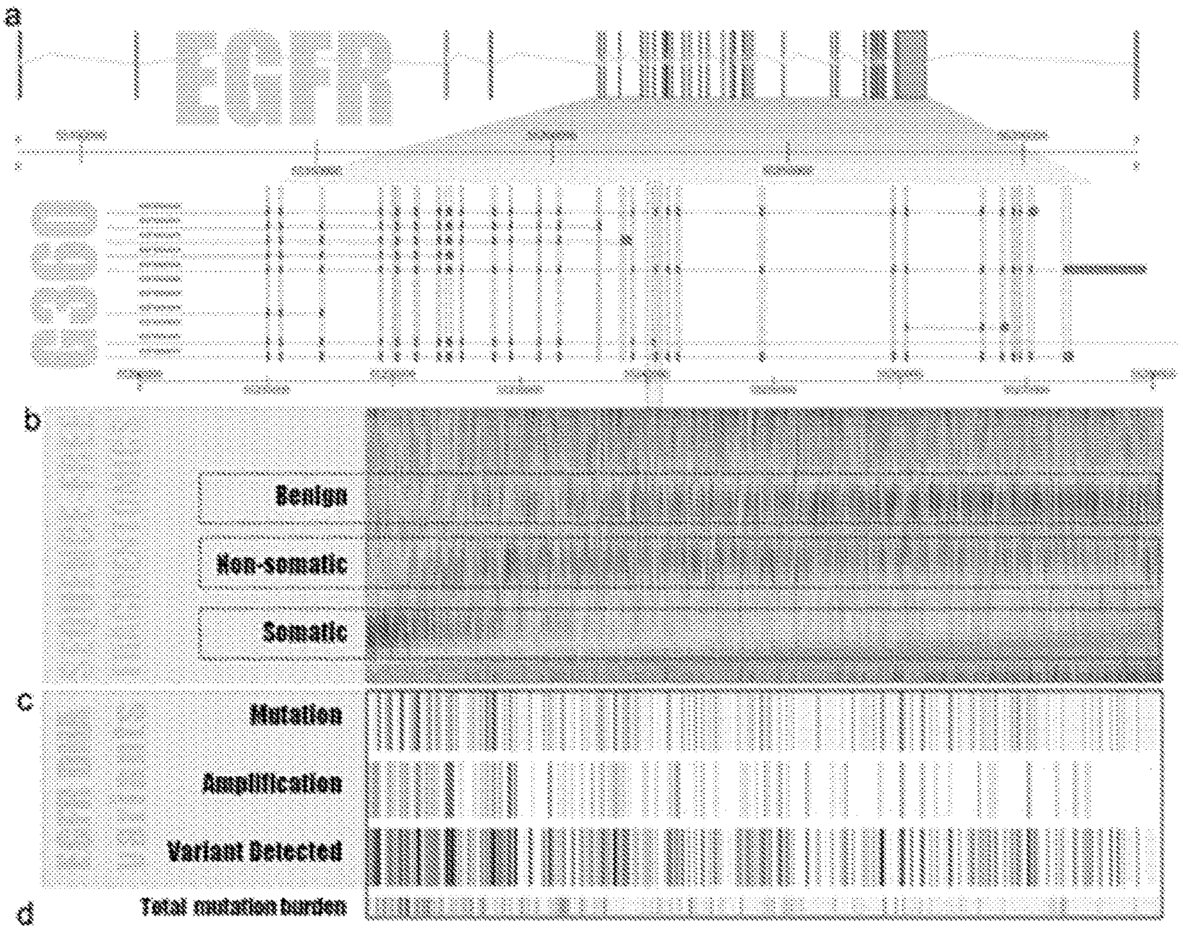
FIG. 23 shows a single-nucleosome resolution fragmentation pattern (e.g., from fragmentome profiling or "fragmentomics" analysis) across tumor types.

Using signal deconvolution of the cfDNA fragmentation patterns, a single-nucleosome resolution fragmentation pattern across tumor types was produced, as seen for the EGFR gene in FIG. 23. As seen in part a, there are multiple genomic regions of the EGFR gene that may contain tumor-associated markers for cancer detection (e.g., which may be assayed by a liquid biopsy). As seen in part b, "sequence-free fragmentomics" analysis reveals variants across genomic regions of the EGFR gene, including benign, non-somatic, and somatic variants. As seen in part c, such EGFR DNA variants may comprise mutations (SNVs) and amplifications (e.g., CNVs). As seen in part d, a total mutation burden is indicated from the detection of variants including SNVs and CNVs by fragmentome analysis.

Figure 24:
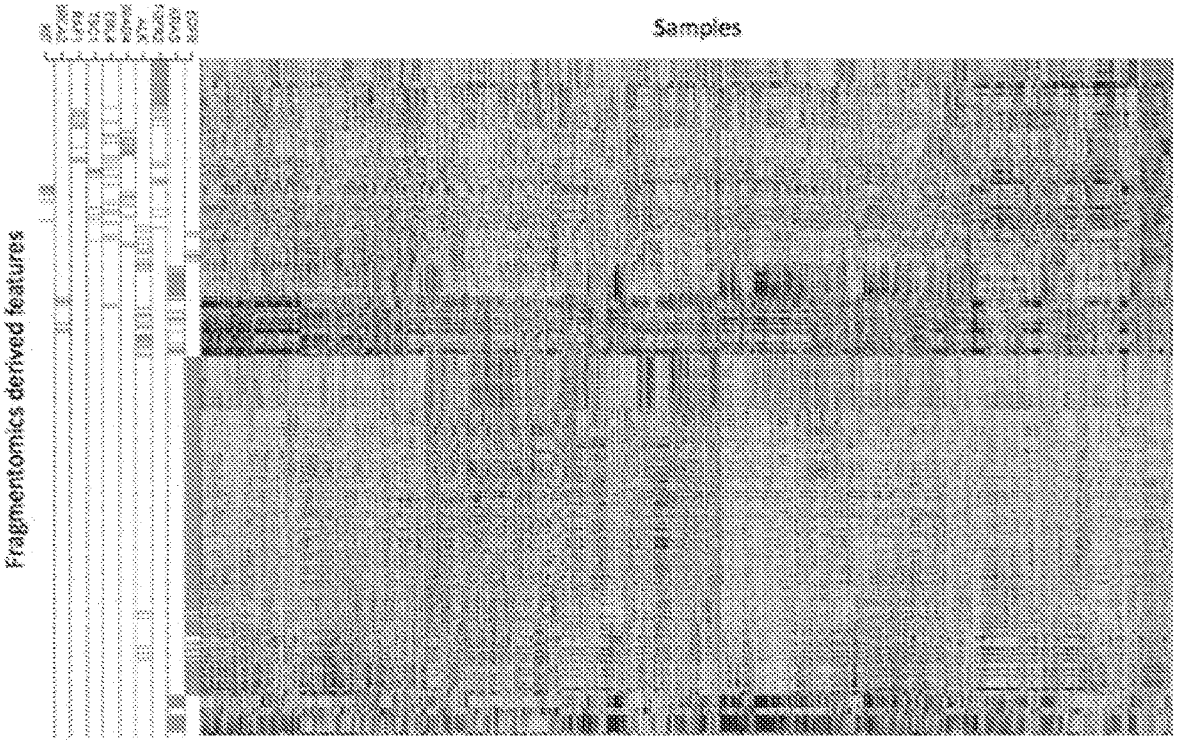
FIG. 24 shows an example of features derived from fragmentome profiling ("fragmentomics") of a cohort comprising 768 patients with late-stage lung adenocarcinoma.

An independent cohort of samples from a validation cohort of 768 patients with late-stage (advanced stage) lung adenocarcinoma was interrogated to assess fragmentomics profiles and to confirm discovered association between patterns of cfDNA positioning and lung cancer-specific nucleosome features. Minimum redundancy feature selection (e.g., as described in Ding et al., J Bioinform Comput Biol 2005 Apr; 3(2):185-205) was performed on the generated fragmentome profiles from the validation cohort of late-stage lung adenocarcinoma patients. This unsupervised clustering analysis identified a subset of lung-cancer specific features (including somatic mutations associated with EGFR, KRAS, FGFR2, ALK, EML4, TSC1, RAF1, BRCA2, and KIT genes), as shown in FIG. 24. Each row (y-axis) denotes one of the 768 cfDNA samples drawn from a patient, and each column (x-axis) denotes a different genomic position corresponding to different genes. In particular, the fragmentome pattern revealed significant clusters of somatic mutations in EGFR, KRAS, and FGFR2 (commonly observed among patients with lung adenocarcinoma and other types of lung cancer, e.g., by genotyping analysis). Thus, fragmentome profile analysis confirmed discovered associations between patterns of cfDNA positioning (fragmentomics) and lung cancer-specific nucleosome features.

Example 3: Cell-Free DNA Fragmentation Patterns (Fragmentome Profiling or "Fragmentomics" Analysis) can be Modeled as a Density for Anomaly Detection A fragmentome profile can be modeled in 3D coordinate space as a density of observed fragment starts and length associated with specific conditions (e.g., malignant or non-malignant, with a malignant condition representing an anomalous case). Such fragmentome profiles may be obtained using a variety of assay methods, such as digital droplet polymerase chain reaction (ddPCR), quantitative polymerase chain reaction (qPCR), and array-based comparative genomic hybridization (CGH). Such "liquid biopsy" assays may be commercially available, such as, for example, a circulating tumor DNA test from Guardant Health, a Spotlight 59 oncology panel from Fluxion Biosciences, an UltraSEEK lung cancer panel from Agena Bioscience, a FoundationACT liquid biopsy assay from Foundation Medicine, and a PlasmaSELECT assay from Personal Genome Diagnostics. Such assays may report measurements of minor allele fraction (MAF) values for each of a set of genetic variants (e.g., SNVs, CNVs, indels, and/or fusions).

Fragmentome profiles may be subjected to analysis by an anomaly detection algorithm to identify abnormal conditions (e.g., malignant cancer in a subject). Anomaly detection is widely used in data mining and may be performed with the use of mixture models and the expectation-maximization (EM) algorithm. Anomaly detection may comprise mixture modeling, a common probabilistic clustering technique in which a distribution of fragment starts and length can be formally described as a K-component (representing K different chromatin configurations) mixture model, as shown in FIG. 25.

Under the above model, a cfDNA start position ("start") and length signal (e.g., the start and length of each of a plurality of cfDNA fragments) may be processed to define a frontier delimiting a contour of a distribution of non-malignant observations for a subset of DNA fragments associated with a particular chromatin unit (e.g., those that have survived cell death and cell clearance). If further observations lie within such a frontier-delimited subspace, these observation points are considered as originating from the same non-malignant population as the initial observations. Otherwise, further observations that lie outside the frontier can be indicative of an abnormal (e.g., originating from a malignant population) cell state. This indication of abnormality may be determined with a given confidence level. Various techniques of data analysis may be used for applying mixture models to cluster sub-populations in a heterogeneous set of observations, including: The One-Class SVM [Estimating the support of a high-dimensional distribution Scholkopf, Bernhard, et al. Neural computation 13.7 (2001): 1443-1471.], Fitting an elliptic envelope [Rousseeuw, P. J., Van Driessen, K. "A fast algorithm for the minimum covariance determinant estimator" Technometrics 41(3), 212 (1999)], and Isolation Forest [Liu, Fei Tony, Ting, Kai Ming and Zhou, Zhi-Hua. "Isolation forest." Data Mining, 2008. ICDM'08. Eighth IEEE International Conference on.], each of which is incorporated herein by reference.

Figure 26A:
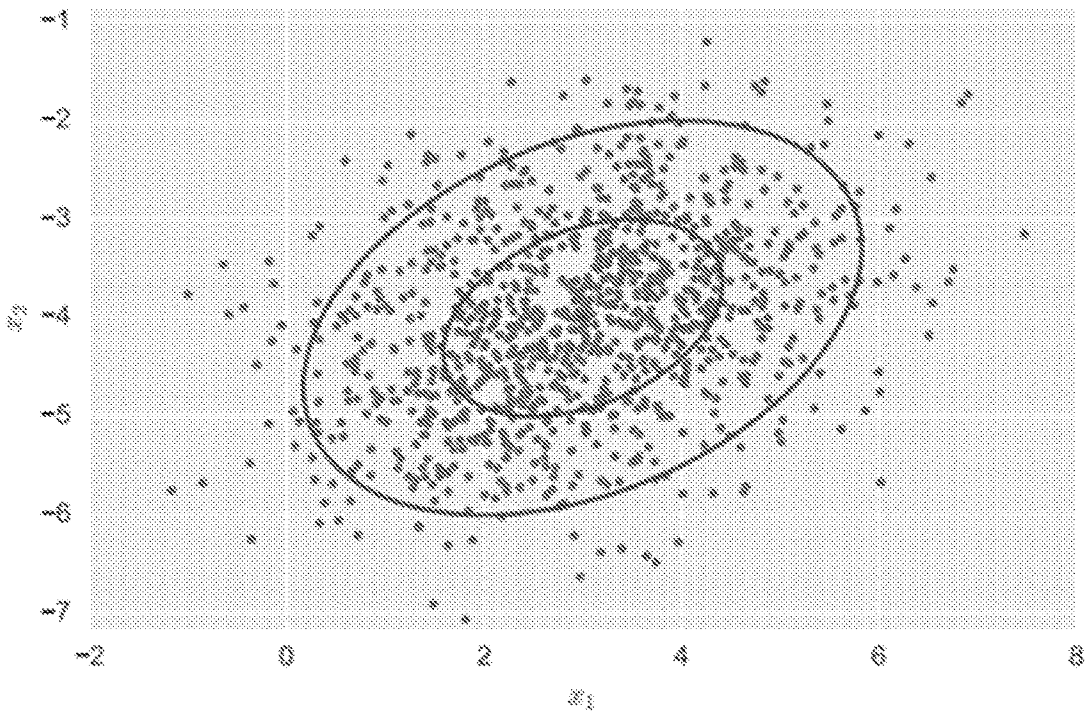
FIG. 26A shows an example of elliptic envelopes which are fitted to a bivariate normal mixture model to identify anomalous cfDNA fragmentome signals.

A method of fitting elliptic envelopes may be applied to the bivariate normal mixture defined above (and shown in FIG. 25). The first operation comprises establishing a contour line associated with fragments arriving from the same histone-protected DNA unit. Such derivation of iso-lines in a multivariate normal is described below and establishes the contour line as an ellipsoid. Given a set of non-malignant control plasma samples, genomic space can be subdivided into non-overlapping segments, which segments define clusters of protected DNA observed in a population of cfDNA fragments. Next, a bivariate normal or bivariate t-distribution model P(x) is built to obtain a probability of a particular fragment coming from a non-malignant cell. If the probability p is below a threshold £, then such a fragment is considered to be anomalous. Summing densities of anomalous fragments across all genomic segments (with proper attention to chromosomes X and Y) results in a quantitative measure of malignancy burden (e.g., tumor burden) that represents a fraction of cfDNA fragments that originated outside non-malignant chromatin configurations (i.e., cfDNA fragments that are anomalous in origin). If a training set comprising a physiologically diverse set of cfDNA samples obtained from a plurality of non-malignant controls (e.g., healthy control subjects), then any detected malignant contribution (e.g., detected anomaly) may be indicative of a cancer origin. Such a malignancy load determination may be performed, by fitting elliptic envelopes to the bivariate normal mixture (as shown in FIG. 26A), such that:

$$(x-\mu)^T\Sigma^{-1}(x-\mu)=c$$

where Σ is the covariance matrix. This equation represents an ellipse. In a simple case, in which μ=(0,0) and Σ is diagonal, the following equation is obtained:

$$(x/\sigma_x)^2+(y/\sigma_y)^2=c$$

In the case that Σ is not diagonal, a diagonalization may be performed to arrive at the same result. Diagonalization techniques are described in, for example, [Hyndman, R. J. (1996) Computing and graphing highest density regions. *The American Statistician,* 50(2), 120-126.], which is incorporated herein by reference.

The following algorithms were performed to train and test the bivariate normal mixture model using cfDNA populations from reference samples (e.g., healthy controls).

First, training was performed using a dataset comprising 40 non-malignant adult plasma samples. For every human chromosome, fragment length was ignored and a kernel density estimate was computed using the "density" function in the statistical software package R. The algorithm (1) disperses the mass of the empirical distribution function over a regular grid of at least 5000 points, then (2) uses a fast Fourier transform to convolve this approximation with a discretized version of the kernel, and then (3) uses linear approximation to evaluate the density at the specified points. The kernel density estimate method is described in, for example, [Venables, W. N. and Ripley, B. D. (2002) Modern Applied Statistics with S. New York: Springer], which is incorporated herein by reference.

Next, valleys were established in the calculated density, in order to establish boundaries of chromatin protection units. A valley is defined as the lowest value in a series where a change in direction has occurred. Next, for every defined segment, a 2D binned kernel density estimate was computed using the KernSmooth package in the statistical software package R. The KernSmooth algorithm is described, for example, in [Wand, M. P. (1994). Fast Computation of Multivariate Kernel Estimators. Journal of Computational and Graphical Statistics, 3, 433-445.], which is incorporated herein by reference. Next, a set of grid points was produced in each coordinate direction (with genomic position as the x-axis and fragment length as the y-axis). Next, the matrix of density estimates was calculated over the mesh induced by the grid points.

The kernel used was the standard bivariate normal density. For each $(x_1, x_2)$ pair on the pre-defined grid, the bivariate Gaussian kernel is centered on that location, and the heights of the kernel, scaled by the bandwidths, at each data point are summed. The grid can be defined as sparsely as necessary (e.g., every 3 bp, 5 bp, etc.), A grid size of 15 bp for both directions was used to minimize memory usage. The bandwidths refer to the kernel bandwidth smoothing parameters, with larger values of bandwidth making smoother estimates and smaller values of bandwidth making less smooth estimates. Heuristic tuning was performed, with a bandwidth of 30 bp, by examining different bandwidths performance in a 12p11.1 region that contains over 400 strongly-positioned nucleosomal profiles (i.e., those profiles that preserve the same nucleosomal structure across multiple tissues, cell lineages and organisms). Such strongly-positioned nucleosomal profiles are described in, for example, Gaffney, D. J. et al. Controls of nucleosome positioning in the human genome. PLoS Genet. 8, e1003036 (2012)], which is incorporated herein by reference. Alternatively, formal bandwidth estimation (available at the URL www.ssc.wisc.edu/~-bhansen/718/NonParametricsl.pdf) may be used to minimize mean integrated squared error.

Next, using the estimated mean and covariance, a 99.995% elliptic envelope was established using the mvtnorm library in the statistical software package R. The algorithm comprises inverting the variance-covariance matrix using the solve( ) function, and the height metric was calculated as the negative of the logarithm of the bivariate normal density using the ellipse( ) function. Other values of elliptic envelopes may be used, such as, for example, at least 60%, at least 65%, at least 70%, at least 75%, at least 80%, at least 85%, at least 90%, at least 95%, at least 96%, at least 97%, at least 98%, at least 99%, at least 99.9%, at least 99.99%, at least 99.999%, or at least 99.9995%.

The training operations described above have established regions in the 3D fragment start position and length space that represented non-malignant clusters with 99.995% confidence. Next, testing of the bivariate normal mixture model was performed using a dataset comprising cfDNA samples obtained from cohorts of lung and colon cancer patients, where the cfDNA samples were derived from both pre-resection and post-resection blood draws. Similarly to training, the testing portion of the algorithm comprised computing 2D kernel density estimates. Next, malignant burden (malignant load, tumor burden, or tumor load) was calculated as a weighted sum of densities outside non-malignant elliptical envelopes. The weights were set as the inverse of the 2D kernel density estimates for the non-malignant training set.

Figure 26B:
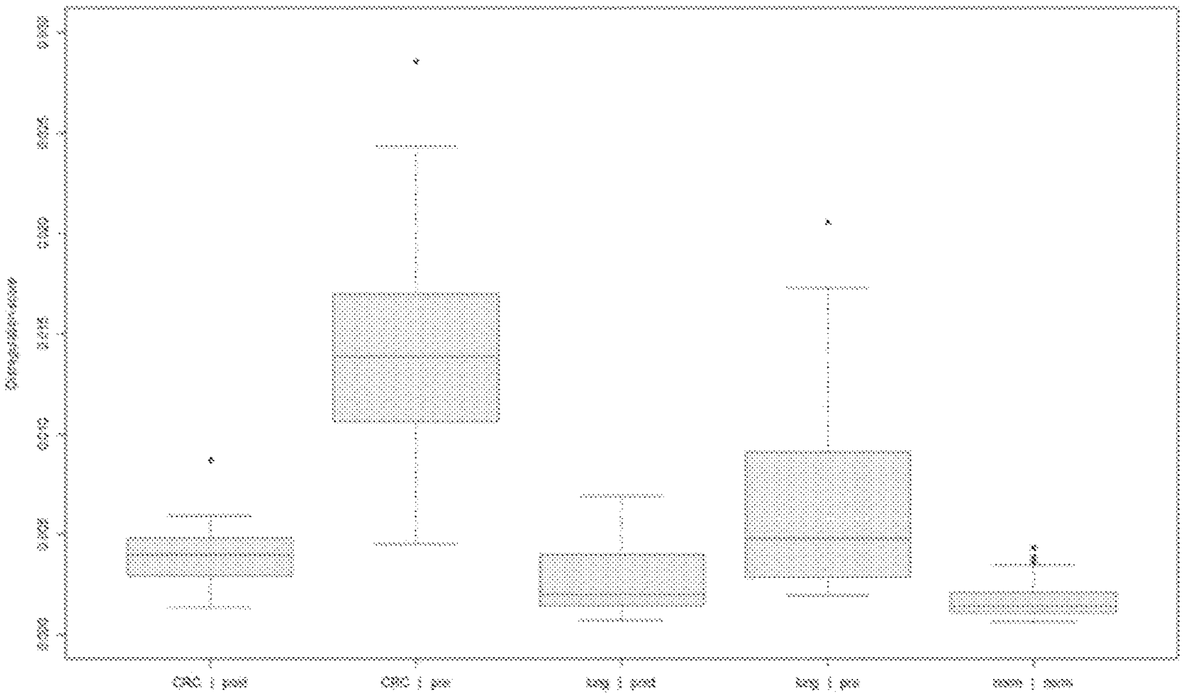
FIG. 26B shows an example of distributions of deregulation scores generated by fragmentome analysis of cfDNA samples across 5 different cohorts (colorectal cancer post-op, colorectal cancer pre-op, lung cancer post-op, lung cancer pre-op, and normal).

FIG. 26B shows an example of distributions of deregulation scores generated by fragmentome analysis of cfDNA samples across 5 different cohorts (colorectal cancer post-op, colorectal cancer pre-op, lung cancer post-op, lung cancer pre-op, and normal), using the bivariate normal mixture model described above. "Post-op" refers to subjects whose cfDNA was analyzed from blood draws made after a surgical resection operation. "Pre-op" refers to subjects whose cfDNA was analyzed from blood draws made prior to a surgical resection operation. Note that deregulation scores (and hence malignant burden) of the colorectal cancer post-op and lung cancer post-op cohorts had lower values and were similar to those of the normal (e.g., healthy) cohort. In contrast, deregulation scores (and hence malignant burden) of the colorectal cancer pre-op and lung cancer pre-op cohorts had significantly higher values than those of the normal (e.g., healthy) cohort. Moreover, the deregulation scores (and hence malignant burden) of the colorectal cancer pre-op and lung cancer pre-op cohorts had significantly higher variation within these cohorts compared to the other three (colorectal cancer post-op, lung cancer post-op, and normal subjects).

Example 4: Cell-Free DNA Fragmentation Patterns (Fragmentome Profiling or "Fragmentomics" Analysis) Reveal Changes Associated with Tumor-Associated Copy Number Variation (CNV)

Cell-free DNA (cfDNA) isolated from circulating blood plasma comprises DNA fragments surviving clearance of dying cells and bloodstream trafficking. In cancer, these fragments carry a footprint of tumor copy number variation as well as their microenvironment, enabling non-invasive plasma-based tumor genotyping in clinical practice. However, the fraction of cancer-derived DNA is typically low, challenging accurate detection in early stages and prompting the search for orthogonal copy number variant-free patterns associated with cancerous state. Because genomic distribution of cfDNA fragments has been shown to reflect nucleosomal occupancy in hematopoietic cells, an experiment was performed (a) to observe heterogeneous patterns of cfDNA positioning in cancer in association with distinct CNVs in patient tumors and (b) to integrate cfDNA positioning into existing analysis. Such approaches may allow increased sensitivity and specificity of detection.

ERBB2 nucleosome dynamics were studied by performing a liquid biopsy assay to measure MAFs for late-stage targeted exomes. A multi-parametric model comprising a 2D heat map of DNA fragment size versus DNA fragment start position (e.g., with DNA fragment coverage as the third dimension) was used to derive a binned approximation to the ordinary kernel density estimate of fragment counts by start position via linear binning, discrete convolutions via FFT and bivariate Gaussian kernel fit, the results of which are shown in FIG. 27A.

Figure 27A:
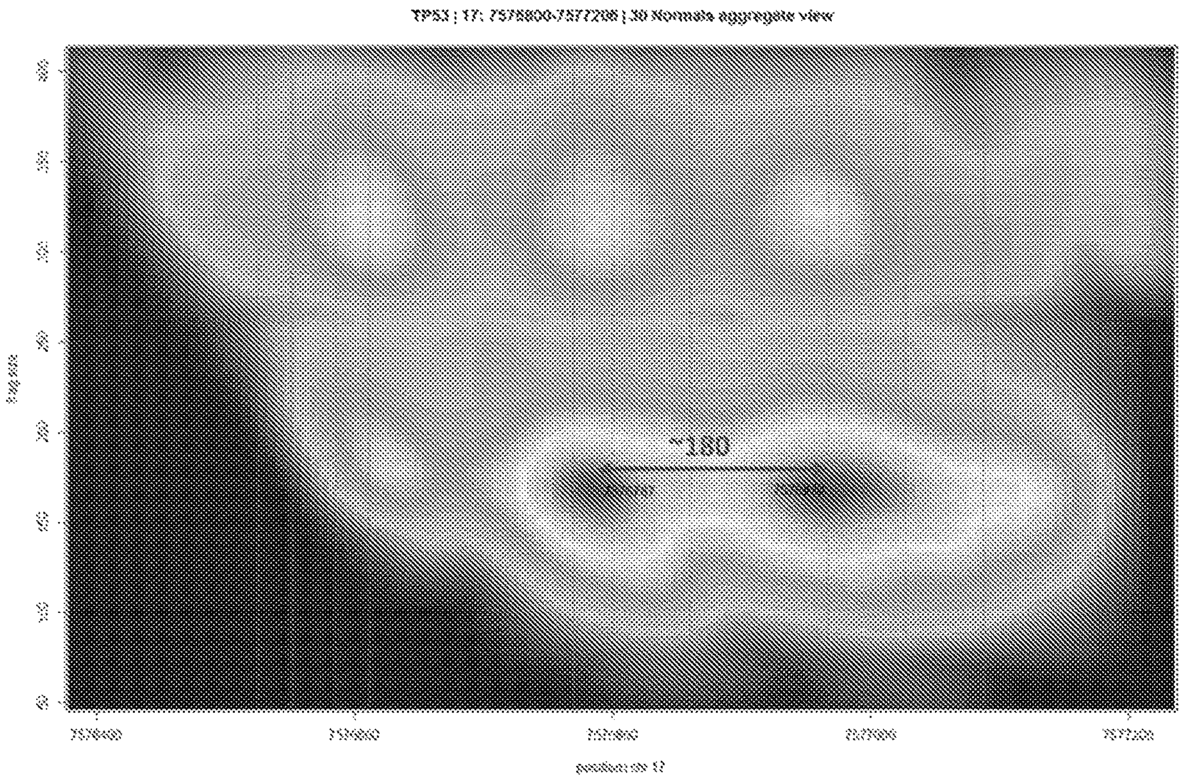
FIG. 27A illustrates an example of a multi-parametric model comprising fragment size (e.g., fragment length) and genomic position of a subject in a region of a genome associated with the TP53 gene, exon #7.
Figure 27B:
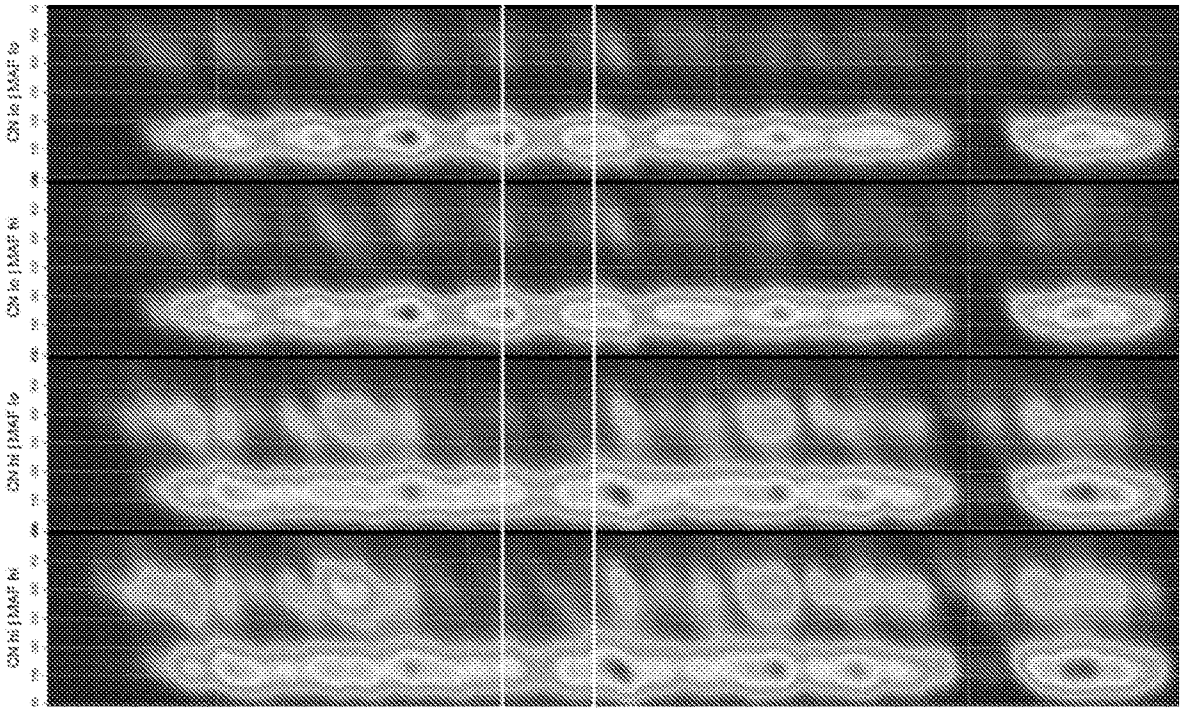
FIG. 27B shows 2D fragment start position (x-axis) and fragment length (y-axis) density heat maps of an ERBB2 promoter region in four aggregated late-stage breast cancer cohorts of 20 samples (as shown from top to bottom): (i) a cohort comprising low mutation burden and near-diploid ERBB2 copy number (CN), (ii) a cohort comprising high mutation burden and near-diploid ERBB2 copy number (CN), (iii) a cohort comprising low mutation burden and high ERBB2 copy number (CN) (e.g., greater than about 4), and (iv) a cohort comprising high mutation burden and high ERBB2 copy number (CN) (e.g., greater than about 4).

FIG. 27A illustrates an example of a multi-parametric model comprising fragment size (e.g., fragment length) (y-axis) and genomic position (x-axis) of a subject in a region of a genome associated with the TP53 gene, exon number 7 (with fragment count in the z-axis denoted by color shading). This multi-parametric model can be used to visualize the effects of cell-free nucleosome positioning. From the multi-parametric model (in this case, a heat map) corresponding to a subject with a tumor, two peaks can be observed, which are separated by about 180 base positions (e.g., along the horizontal axis corresponding to position). In addition, three peaks corresponding to mononucleosomal protection can be observed (e.g., corresponding to a fragment size in a range of about 160 to about 180 base positions (bp)). In addition, three peaks corresponding to dinucleosomal protection can be observed (e.g., corresponding to a fragment size in a range of about 320 to about 340 base positions (bp)). Each of these peaks may comprise a position (e.g., at the center of the peak along the horizontal axis), a fragment size (e.g., at the center of the peak along the vertical axis), and a peak width (e.g., along one of the axes).

Figure 27C:
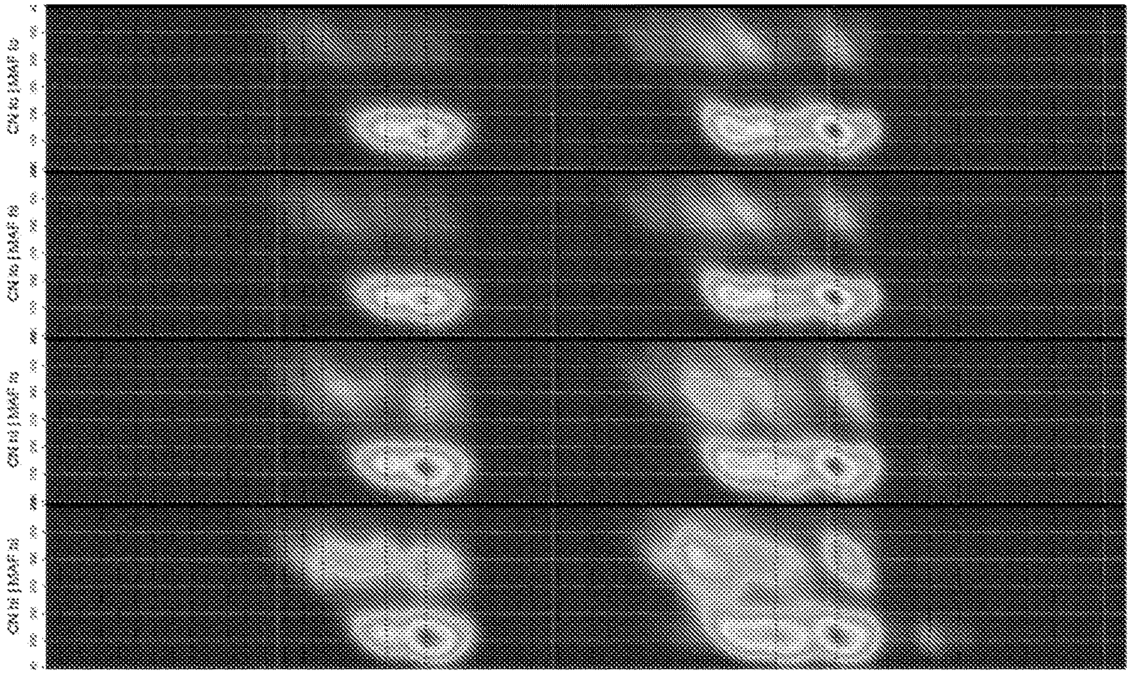
FIG. 27C shows 2D fragment start position (x-axis) and fragment length (y-axis) density heat maps of an ERBB2 enhancer region in four aggregated late-stage breast cancer cohorts of 20 samples (as shown from top to bottom): (i) a cohort comprising low mutation burden and near-diploid ERBB2 copy number (CN), (ii) a cohort comprising high mutation burden and near-diploid ERBB2 copy number (CN), (iii) a cohort comprising low mutation burden and high ERBB2 copy number (CN) (e.g., greater than about 4), and (iv) a cohort comprising high mutation burden and high ERBB2 copy number (CN) (e.g., greater than about 4).

Both regulatory elements (e.g., the promoter and enhancer regions associated with the ERBB2 gene) were examined by whole-genome analysis in a cohort of 20 ERBB2-negative and ERBB2-positive late-stage breast cancer patients. Such studies revealed sufficient fragment coverage with anticipated chromatin structure of nucleosomal clearance in ERBB2-positive cases as well as a presence of dinucleosomal clusters associated with expression, as shown in FIGS. 27B and 27C.

FIG. 27B shows 2D fragment start position (x-axis) and fragment length (y-axis) density heat maps of an ERBB2 promoter region in four aggregated late-stage breast cancer cohorts of 20 samples (as shown from top to bottom): (i) a cohort comprising low mutation burden and near-diploid ERBB2 copy number (CN), (ii) a cohort comprising high mutation burden and near-diploid ERBB2 copy number (CN), (iii) a cohort comprising low mutation burden and high ERBB2 copy number (CN) (e.g., greater than about 4), and (iv) a cohort comprising high mutation burden and high ERBB2 copy number (CN) (e.g., greater than about 4).

The cohort comprising low mutation burden and near-diploid ERBB2 copy number (CN) represents subjects who likely have a low tumor burden and low CNV in the ERBB2 gene in the tumor. The cohort comprising high mutation burden and near-diploid ERBB2 copy number (CN) represents subjects who likely have a high tumor burden but low CNV in the ERBB2 gene in the tumor. As seen in the heat maps in the top two rows of FIG. 27B, subjects with low CNV in the ERBB2 gene in the tumor exhibited similar fragmentome profiles across both low mutation burden and high mutation burden cases.

The cohort comprising low mutation burden and high ERBB2 copy number (CN) (e.g., greater than about 4) represents subjects who likely have a low tumor burden but have high CNV in the ERBB2 gene in the tumor. The cohort comprising high mutation burden and high ERBB2 copy number (CN) (e.g., greater than about 4) represents subjects who likely have a high tumor burden and have high CNV in the ERBB2 gene in the tumor. As seen in the heat maps in the bottom two rows of FIG. 27B, subjects with high CNV in the ERBB2 gene in the tumor exhibited similar fragmentome profiles across both low mutation burden and high mutation burden cases. In addition, the subjects with high CNV in the ERBB2 gene exhibited fragmentome profiles with (i) the appearance of more dinucleosomal peaks (located in the upper portion of each row's heat map along the vertical axis corresponding to fragment length) and (ii) a greater distance between two peaks and "smearing" (e.g., less pronounced peaks, which have larger widths and hence begin to merge together) of other peaks.

FIG. 27C shows 2D fragment start position (x-axis) and fragment length (y-axis) density heat maps of an ERBB2 enhancer region in four aggregated late-stage breast cancer cohorts of 20 samples (as shown from top to bottom): (i) a cohort comprising low mutation burden and near-diploid ERBB2 copy number (CN), (ii) a cohort comprising high mutation burden and near-diploid ERBB2 copy number (CN), (iii) a cohort comprising low mutation burden and high ERBB2 copy number (CN) (e.g., greater than about 4), and (iv) a cohort comprising high mutation burden and high ERBB2 copy number (CN) (e.g., greater than about 4).

The cohort comprising low mutation burden and near-diploid ERBB2 copy number (CN) represents subjects who likely have a low tumor burden and low CNV in the ERBB2 gene in the tumor. The cohort comprising high mutation burden and near-diploid ERBB2 copy number (CN) represents subjects who likely have a high tumor burden but low CNV in the ERBB2 gene in the tumor. As seen in the heat maps in the top two rows of FIG. 27C, subjects with low CNV in the ERBB2 gene in the tumor exhibited similar fragmentome profiles across both low mutation burden and high mutation burden cases.

The cohort comprising low mutation burden and high ERBB2 copy number (CN) (e.g., greater than about 4) represents subjects who likely have a low tumor burden but have high CNV in the ERBB2 gene in the tumor. The cohort comprising high mutation burden and high ERBB2 copy number (CN) (e.g., greater than about 4) represents subjects who likely have a high tumor burden and have high CNV in the ERBB2 gene in the tumor. As seen in the heat maps in the bottom two rows of FIG. 27C, subjects with high CNV in the ERBB2 gene in the tumor exhibited similar fragmentome profiles across both low mutation burden and high mutation burden cases. In addition, the subjects with high CNV in the ERBB2 gene exhibited fragmentome profiles with the appearance of more dinucleosomal peaks (located in the upper portion of each row's heat map along the vertical axis corresponding to fragment length).

Figure 28A:
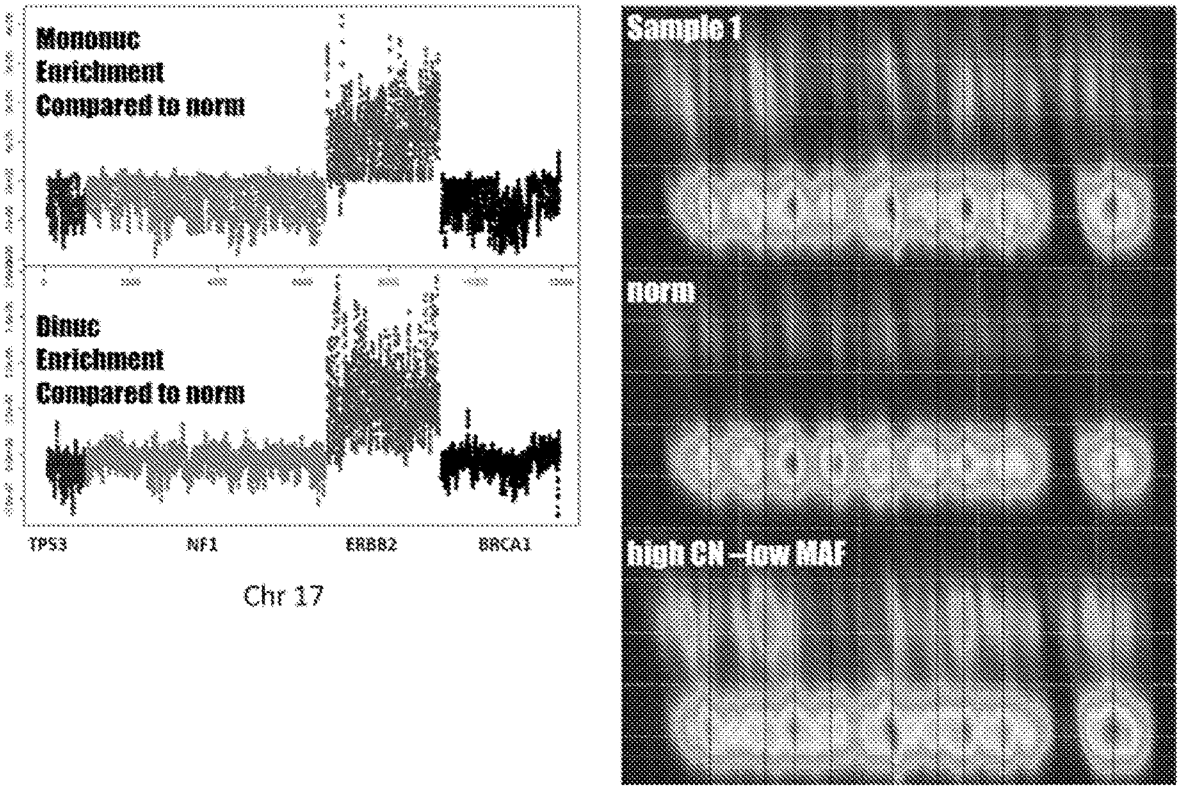
FIG. 28A shows aligned 2D fragment start position (x-axis) and fragment length (y-axis) density heat maps (as shown from top to bottom): (i) a heat map of an ERBB2 enhancer region (top right), generated from a single sample (from an ERBB2 positive subject), (ii) an aggregated cohort heat map generated from a plurality of healthy controls, and (iii) an aggregated cohort heat map generated from a plurality of high ERBB2 CN and low mutation burden subjects. In addition, a coverage plot of mononucleosomal and dinucleosomal counts (e.g., number of fragments counted in the test sample that start at that genomic position) are shown at 4 different genomic regions (e.g., corresponding to TP53, NF1, ERBB2, and BRCA1 genes).
Figure 28B:
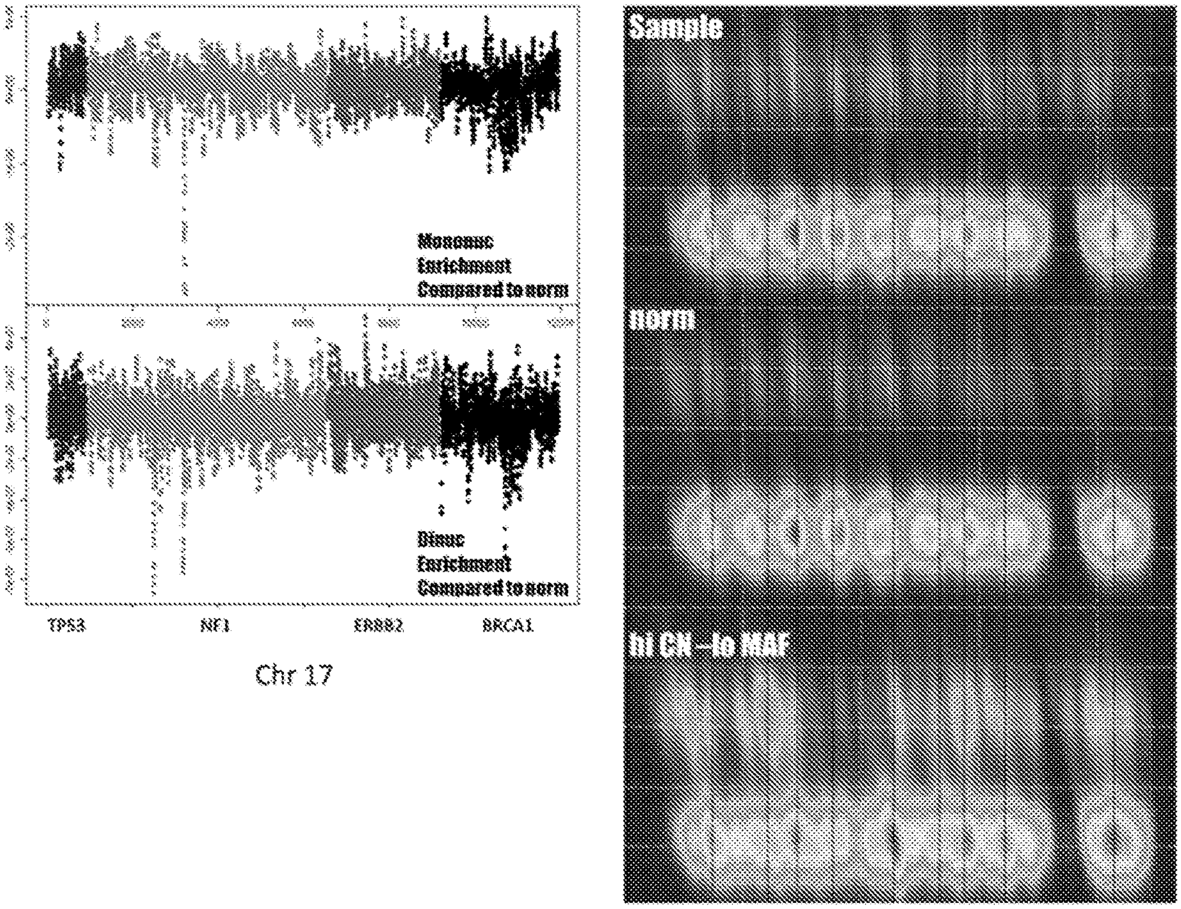
FIG. 28B shows aligned 2D fragment start position (x-axis) and fragment length (y-axis) density heat maps (as shown from top to bottom): (i) a heat map of an ERBB2 enhancer region (top right), generated from a single sample (from an ERBB2 negative subject), (ii) an aggregated cohort heat map generated from a plurality of healthy controls, and (iii) an aggregated cohort heat map generated from a plurality of high ERBB2 CN and low mutation burden subjects. In addition, a coverage plot of mononucleosomal and dinucleosomal counts is shown at 4 different genomic regions (e.g., corresponding to TP53, NF1, ERBB2, and BRCA1 genes).

Fragmentome analysis of individual subject samples confirmed the feasibility of chromatin structure detection using a targeted assay such as a liquid biopsy assay, as shown in FIGS. 28A and 28B.

FIG. 28A shows aligned 2D fragment start position (x-axis) and fragment length (y-axis) density heat maps (right side; as shown from top to bottom): (i) a heat map of an ERBB2 enhancer region (top right), generated from a single sample (from an ERBB2 positive subject), (ii) an aggregated cohort heat map generated from a plurality of healthy controls, and (iii) an aggregated cohort heat map generated from a plurality of high ERBB2 CN/low mutation burden subjects. In addition, a coverage plot of mononucleosomal and dinucleosomal counts (e.g., number of fragments counted in the test sample that start at that genomic position) are shown at 4 different genomic regions (e.g., corresponding to TP53, NF1, ERBB2, and BRCA1 genes) (left side). The test sample exhibits a fragmentome profile (right) that is more similar to that of the high ERBB2 CN and low mutation burden cohort (e.g., with the appearance of peaks of dinucleosomal fragments, or "dinucleosomal peaks") than the cohort of healthy controls. In addition, the test sample exhibits a coverage plot (left) of mononucleosomal and dinucleosomal counts which are both significantly elevated in the ERBB2 gene region (e.g., by several times) compared to the other 3 genes (TP53, NF1, and BRCA1). Thus, the fragmentome profile and the coverage plot of the test sample both indicate and confirm that the test subject is likely ERBB2 positive. By performing fragmentome profiling, a presence of a CN genetic aberration in ERBB2 gene was measured and obtained without taking into account a base identity of each base position in a locus of the ERBB2 gene.

FIG. 28B shows aligned 2D fragment start position (x-axis) and fragment length (y-axis) density heat maps (as shown from top to bottom): (i) a heat map of an ERBB2 enhancer region (top right), generated from a single sample (from an ERBB2 negative subject), (ii) an aggregated cohort heat map generated from a plurality of healthy controls, and (iii) an aggregated cohort heat map generated from a plurality of high ERBB2 CN/low mutation burden subjects. In addition, a coverage plot of mononucleosomal and dinucleosomal counts (e.g., number of fragments counted in the test sample that start at that genomic position) are shown at 4 different genomic regions (e.g., corresponding to TP53, NF1, ERBB2, and BRCA1 genes). The test sample exhibits a fragmentome profile (right) that is more similar to that of the cohort of healthy controls (e.g., with the absence of peaks of dinucleosomal fragments, or "dinucleosomal peaks") than the high ERBB2 CN and low mutation burden cohort. In addition, the test sample exhibits a coverage plot (left) of mononucleosomal and dinucleosomal counts which are not elevated in the ERBB2 gene region compared to the other 3 genes (TP53, NF1, and BRCA1). Thus, the fragmentome profile and the coverage plot of the test sample both indicate and confirm that the test subject is likely ERBB2 negative. By performing fragmentome profiling, an absence of a CN genetic aberration in ERBB2 gene was measured and obtained without taking into account a base identity of each base position in a locus of the ERBB2 gene.

In an aspect, disclosed herein is a method for generating an output indicative of a presence or absence of a genetic aberration in deoxyribonucleic acid (DNA) fragments from a cell-free sample (or cell-free DNA) obtained from a subject. The method may comprise the identification of one or more peaks from a fragmentome profile (e.g., a 2D heat map plot). Such identification may comprise constructing a distribution of the DNA fragments from the cell-free sample (or cell-free DNA) over a plurality of base positions in a genome. Next, one or more peaks at one or more base positions of the plurality of base positions may be identified in the distribution of the DNA fragments. Each such peak may comprise a peak value and a peak distribution width. Next, the presence or absence of the genetic aberration in the subject may be determined. Such determination may be based at least on (i) the one or more base positions, (ii) the peak value, and/or (iii) the peak distribution width. In some embodiments, the one or more peaks comprise a dinucleosomal peak and/or a mononucleosomal peak.

In some embodiments, the output indicative of a presence or absence of the genetic aberration is determined based at least on a quantitative measure indicative of a ratio of a first peak value associated with the dinucleosomal peak and a second peak value associated with the mononucleosomal peak, or vice versa. For example, a ratio of a dinucleosomal peak value (and/or peak distribution width ("peak width")) to a mononucleosomal peak value (and/or peak width) may be used to indicate whether a fragmentome profile of a test sample can be pattern matched to a fragmentome profile (having similar peak locations, peak values, and/or peak widths) of one or more healthy control subjects (or cohorts) and/or one or more diseased subjects (or cohorts).

Once a multi-parametric distribution (e.g., a 2D density plot or heat map) is generated, a multimodal density may be estimated; however, such estimation may be challenging even in one dimension. For a unimodal model, the density shape may be described by parameters (e.g., skewness and kurtosis) that may be generated using well-known methods of multivariate distribution analysis. For a multimodal model, multimodal density analysis (e.g., of parameters such as fragment start positions ("fragment start")) may be performed to determine a number of modes and a location of each such mode, since modes are a dominant feature mimicking epigenetic cap analysis gene expression (CAGE) peaks of chromatin marks, and may be potentially symptomatic of underlying chromatin organization.

A multimodal density analysis may comprise use of a mixture model, which provides a decomposition of the sampled population into a set of homogeneous components in a way that is consistent with the multimodal density configuration. Various methods and approaches may be used to determine the modal behavior of multivariate normal mixtures, e.g., machine learning algorithms. As an example, image processing and image segmentation algorithms, such as a watershed transformation suitable for a topographic map, may be performed on a multi-parametric distribution (e.g., a fragmentome 2D densities). Such watershed transformation approaches may represent the fragmentome profile such that the brightness of each point representing its height, thus multimodal density analysis may comprise determining the one or more lines that run along the tops of ridges of such watershed plots. Using such transformation approaches, fragmentome profiles were analyzed to map canonical nucleosomal architecture via topographic modeling of bivariate normal mixtures, as shown in FIG. 29A.

Figure 29A:
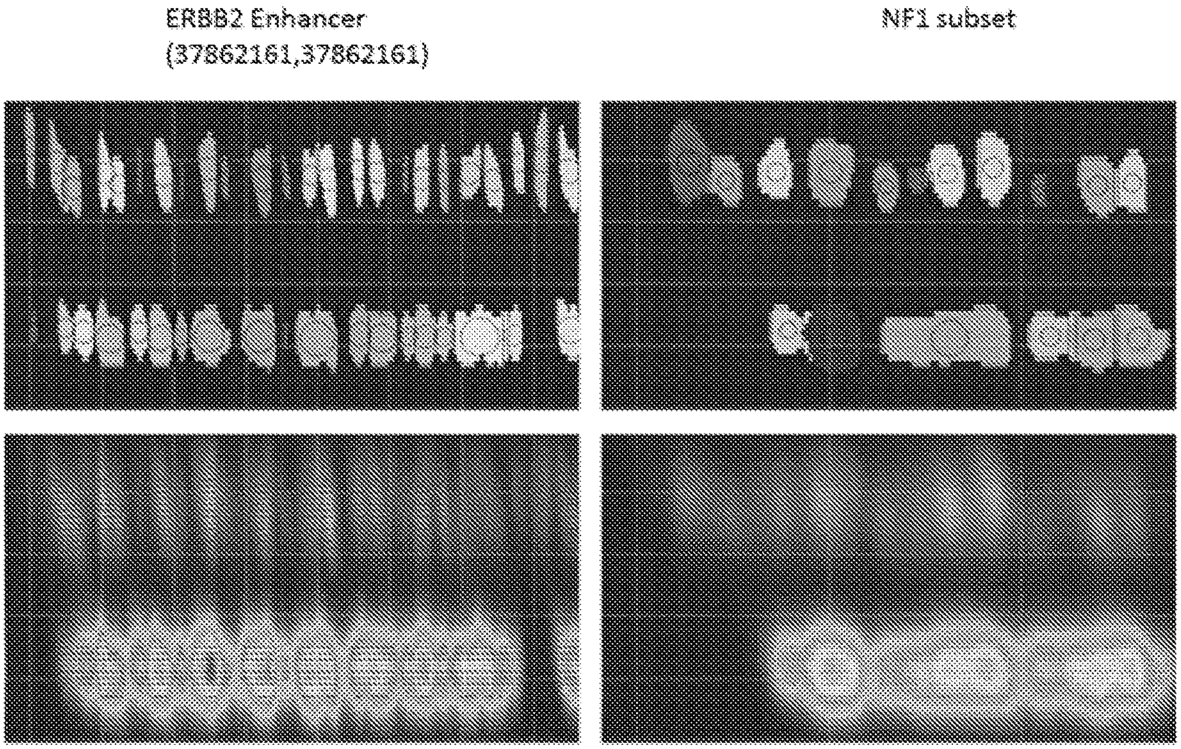
FIGS. 29A and 29B show plots of 2D nucleosome mapping for ERBB2 and NF1 exonic domains (without amplification). At the bottom of each figure, a 2D density estimate and image processing are shown. At the top of each figure, a nucleosomal mask for an observed canonical domain across 30 near-diploid ERBB2 clinical cases is shown.

FIG. 29A shows a 2D nucleosome mapping for ERBB2 and NF1 exonic domains (without amplification). Such a nucleosome mapping may be obtained, for example, by performing a ridgeline reconstruction of a fragmentome profile associated with the ERBB2 promoter region and an adjacent gene NF1 on chromosome 17. In this process, nucleosome masks were fitted to the fragmentome profile.

Here, the signal represents contours of nucleosomal boundaries and the variation of the densities on such contours. At the bottom of the figure, a 2D density estimate and image processing are shown. At the top of the figure, a nucleosomal mask for an observed canonical domain across 30 near-diploid ERBB2 clinical cases (e.g., subjects whose liquid biopsy assays reported MAF values indicative of low or no CNV). Healthy subjects were examined and subjected to fragmentome profiling, and contours were determined where nucleosomes are expected to be present. Such analysis comprised the use of delta signals, wherein each delta signal comprises a difference between the distribution of the DNA fragments (e.g., of a test sample) and a reference distribution (e.g., a canonical distribution of healthy controls). A mask was constructed based on healthy controls, and this mask was applied to the test sample. The resulting plot indicates that this test sample has a fragmentome profile that is quite similar to that of the cohort of healthy controls.

The nucleosome masking approach was then applied to an entire targeted domain of chromosome 17 (chr17) and extended to a larger clinical cohort of 7,000 samples which were assayed by a liquid biopsy assay, which samples represented advanced cancer patients across 4 tissue types (prostate, colon, breast, and lung). Fragmentome signals were deconvolved to produce a canonical nucleosomal mask of a chr17 targeted domain that included the 4 genes of ERBB2, NF1, BRCA1, and TP53.

Figure 30:
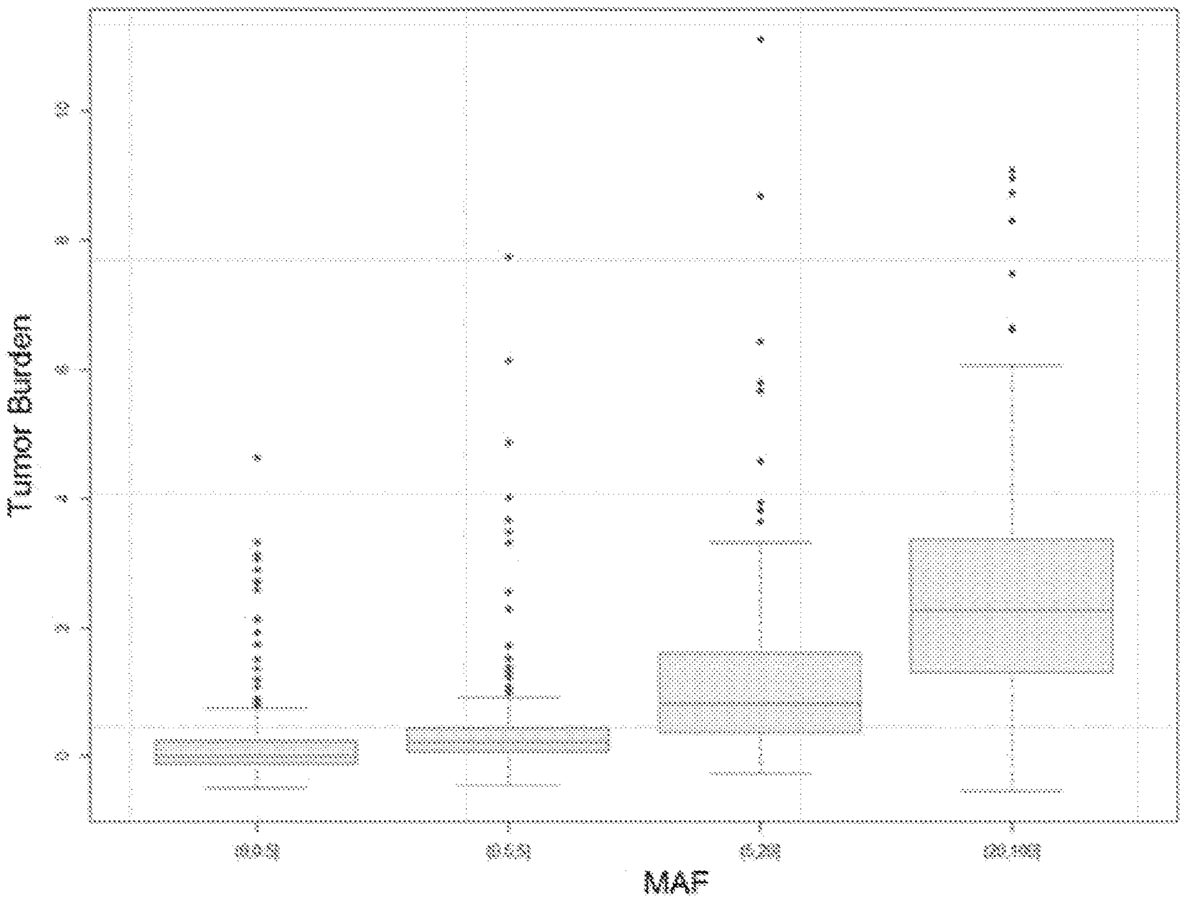
FIG. 30 shows a plot of inferred chromosome 17 tumor burden across 4 different cohorts which had previously been assayed for maximum MAF by a liquid biopsy assay: (i) a cohort with a maximum MAF in a range of (0, 0.5], (ii) a cohort with a maximum MAF in a range of (0.5,5], (iii) a cohort with a maximum MAF in a range of (5,20], and (iv) a cohort with a maximum MAF in a range of (20,100].
Figure 31A:
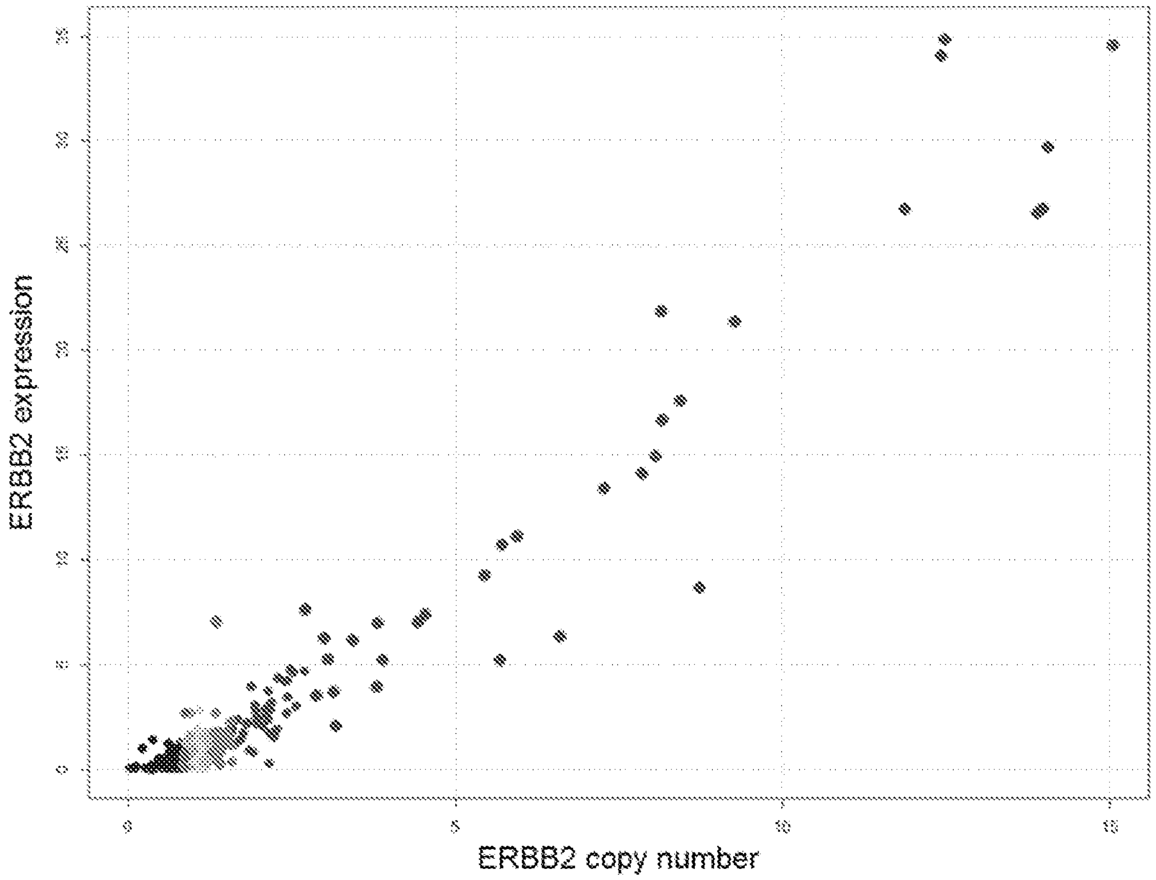
FIG. 31A shows a plot of ERBB2 expression component vs. ERBB2 copy number.

Next, nucleosome-specific features derived from a pan-cancer near-diploid ERBB2 copy number training set were used to estimate ERBB2 expression component and chromosome 17 tumor burden by contrasting residual masks of the ERBB2 gene to those in neighboring genes across 811 advanced stage breast carcinoma samples which were assayed for tumor-associated minor allele frequencies (MAF). Specifically, tumor burden was assessed as an iterative residual measurement across non-ERBB2 domain, robustified against focal amplification events (as shown in FIG. 30) and ERBB2 expression measure was calculated as residual density estimate in ERBB2 dinucleosomal vs mononucleosomal channels for ERBB2 expression vs. copy number estimates (as shown in FIG. 31A) across 811 breast cancer samples. ERBB2 copy number was determined as a residual density in ERBB2 mononucleosomes, corrected for mutational burden, and assessed outside ERBB2 boundaries.

Figure 29B:
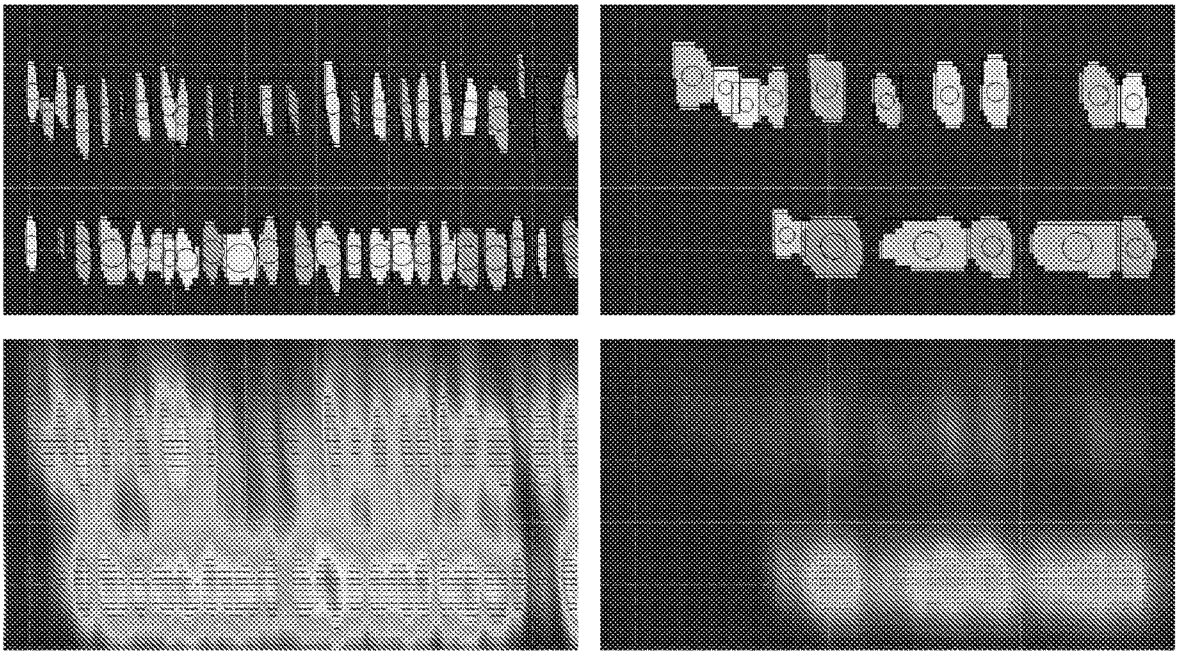

FIG. 29B shows a 2D nucleosome mapping for ERBB2 and NF1 exonic domains (without amplification). At the bottom of the figure, a 2D density estimate and image processing are shown. At the top of the figure, a nucleosomal mask for an observed canonical domain across 30 ERBB2 clinical cases is shown. In this process, pattern matching was performed using a comparison between the test sample and the canonical healthy profile (e.g., by performing signal deconvolution and pattern recognition on the deconvolved signals). Multiple approaches may be used for the comparison to observe differences. For example, a log likelihood can be calculated to measure a distance (or delta signal) between an observed signal to (i) one or a plurality of canonical masks (e.g., from healthy controls), (ii) one or a plurality of positive abnormal profiles, or (iii) a combination of both. As another example, an image processing algorithm may be performed for fragmentome profile comparisons. Such distances or delta signals may then be compared to determine if a given test sample has a fragmentome profile that is indicative of the subject being more likely to be in a healthy or a diseased state. Comparisons to a plurality of reference distributions (e.g., one or more healthy and one or more diseased) may be incorporated into a single comparison.

FIG. 30 shows a plot of inferred chromosome 17 tumor burden across 4 different cohorts which had previously been assayed for maximum MAF by a liquid biopsy assay: (i) a cohort with a maximum MAF in a range of (0, 0.5], (ii) a cohort with a maximum MAF in a range of (0.5,5], (iii) a cohort with a maximum MAF in a range of (5,20], and (iv) a cohort with a maximum MAF in a range of (20,100]. The cell clearance of the tumor (e.g., the tendency of the tumor to shed cells and cell-free DNA into circulation) may be measured by calculating a quantitative measure of the NF1 gene or other non-cancer marker. For example, such a quantitative measure may be a ratio of a number of measured fragments with dinucleosomal protection to a number of measured fragments with mononucleosomal protection. A distribution of DNA fragments from a cell-free sample (or cell-free DNA) obtained from a subject (e.g., a multi-parametric distribution or a uni-parametric distribution) may be deconvolved into one or more components at a genetic locus. Such components may comprise one, two, three of copy number (CN), cell clearance, and gene expression. The deconvolution may comprise constructing a distribution of a coverage of the DNA fragments from the cell-free sample (or cell-free DNA) over a plurality of base positions in a genome. Next, the deconvolution may comprise, for each of one or more genetic loci, deconvolving the distribution of the coverage, thereby generating fractional contributions associated with a copy number (CN) component, a cell clearance component, and/or a gene expression component.

FIG. 31A shows a plot of ERBB2 expression component vs. ERBB2 copy number. Here, ERBB2 expression measurements (y-axis) were calculated as a residual density estimate in ERBB2 dinucleosomal vs mononucleosomal channels across 811 breast cancer samples. The ERBB2 promoter region was examined to observe chromatin reorganization events associated with a copy number change. Since copy number changes are related to expression, expression can be estimated from fragmentome signals. For a cohort of subjects with ERBB2 status previously confirmed as HER2 positive via FISH and/or immunohistochemistry (IHC), fragmentome profiles were examined in the ERBB2 promoter region in this cohort, and a mask of ERBB2 positive expression was identified. Similarly, a mask for an ERBB2 negative cohort (again, verified clinically by FISH and/or IHC) was generated to identify a mask for ERBB2 negative expression. Thus, for a given test sample, analysis of the associated fragmentome profile (e.g., as a mixture of ERBB-positive profiles and ERBB2-negative profiles) can reveal a likelihood (e.g., a log likelihood associated with pattern matching) of matching either the ERBB2 positive or the ERBB2 negative fragmentome pattern. For each subject in the cohort, ERBB2 copy number was measured from coverage numbers of associated fragmentome profiles.

Figure 31B:
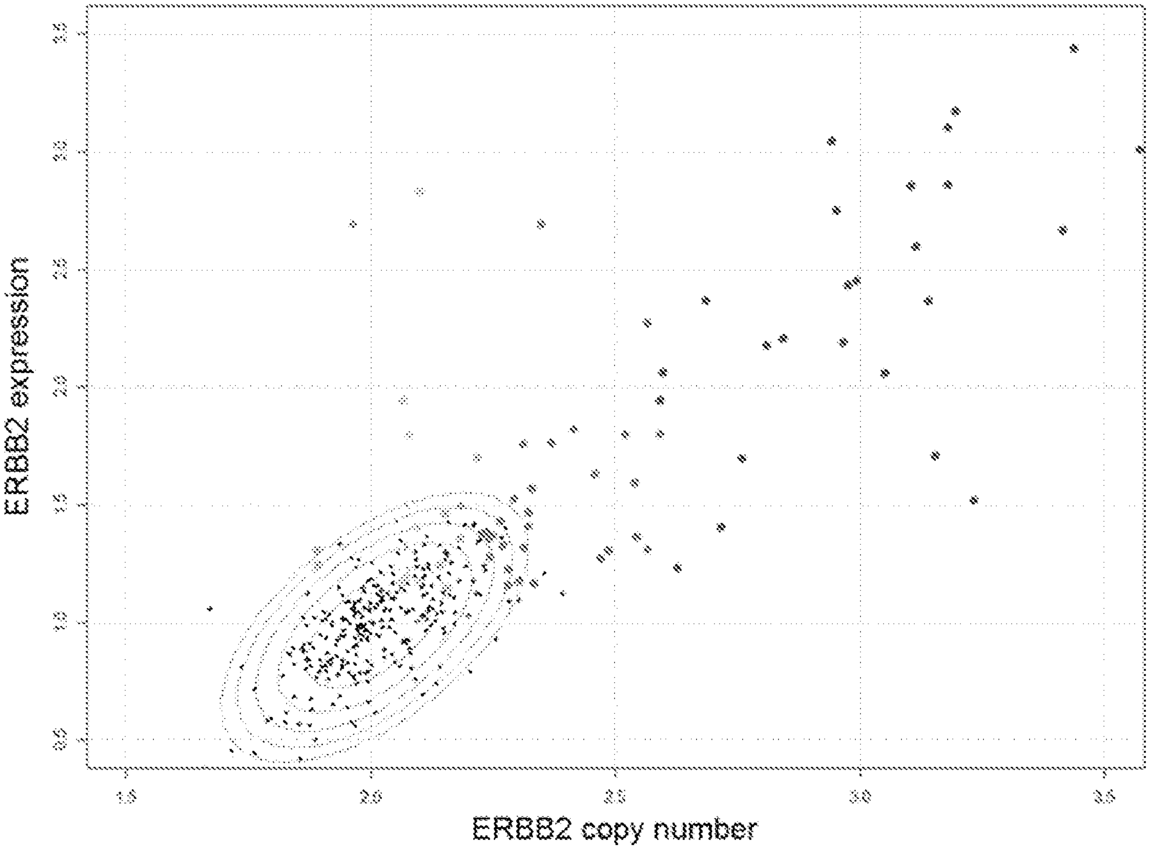
FIG. 31B shows a plot of 2D thresholding using ERBB2-negative training set, which is performed via construction of a variance-covariance matrix, inverting the variance-covariance matrix, and generating an ellipse discrimination function.

FIG. 31B shows a plot of 2D thresholding using ERBB2-negative training set, which is performed via construction of a variance-covariance matrix, inverting the variance-covariance matrix, and generating an ellipse discrimination function. The multivariate normal distribution of ERBB2 expression and copy number was parameterized with a mean vector, $\mu$, and a covariance matrix, $\Sigma$ and used to produce discrimination scores. This procedure was used to test a test sample for inclusion within the ellipses created by a bivariate normal approximation to the ERBB2-negative training data. The ellipses (as shown in FIG. 31B) were determined by the first and second moments of the data. Inversion of the variance-covariance matrix of the multivariate normal distribution of ERBB2 expression and copy number produced a discrimination score. This discrimination score was calculated as the negative logarithm of the bivariate normal density.

TABLE 2

| | | FISH\|IHC | | | | FISH\|IHC | | |
|---|---|---|---|---|---|---|---|---|
| | | Negative | Positive | | | Negative | Positive | |
| Conventional | Detected | 4 | 17 | 21 | fragmentomics | 2 | 21 | 23 |
| CNV | Not Detected | 26 | 11 | 37 | | 28 | 7 | 35 |
| | Totals | 30 | 28 | 58 | | 30 | 28 | 58 |
| | | Estimated Value | 95% Confidence Interval Lower Limit | Upper Limit | | Estimated Value | 95% Confidence Interval Lower Limit | Upper Limit |
| | Sensitivity | 0.61 | 0.41 | 0.78 | | 0.75 | 0.55 | 0.89 |
| | Specificity | 0.87 | 0.68 | 0.96 | | 0.93 | 0.76 | 0.99 |

Table 2 shows amplification detection summary results in 58 samples with known HER2 immunohistochemistry status. These results include sensitivity and specificity summaries of the independent test set of ERBB2-positive and ERBB2-negative breast cancer cases, which were verified by immunohistochemistry (IHC) and Fluorescence in situ hybridization (FISH). These results indicate that fragmentomics (analysis of fragmentome profiles) enabled the amplification detection of ERBB2-positive and ERBB2-negative breast cancer cases with higher sensitivity and specificity compared to traditional CNV detection approaches. Such fragmentomics approaches may be performed in parallel to traditional CNV detection approaches (e.g., approaches that take into account base identities of base positions in one or more genetic loci) to detect CNV at higher sensitivity and higher specificity. Alternatively, such fragmentomics approaches may be performed in combination with traditional CNV detection approaches (e.g., approaches that take into account base identities of base positions in one or more genetic loci) to detect CNV at higher sensitivity and higher specificity than either method alone.

Figure 32A:
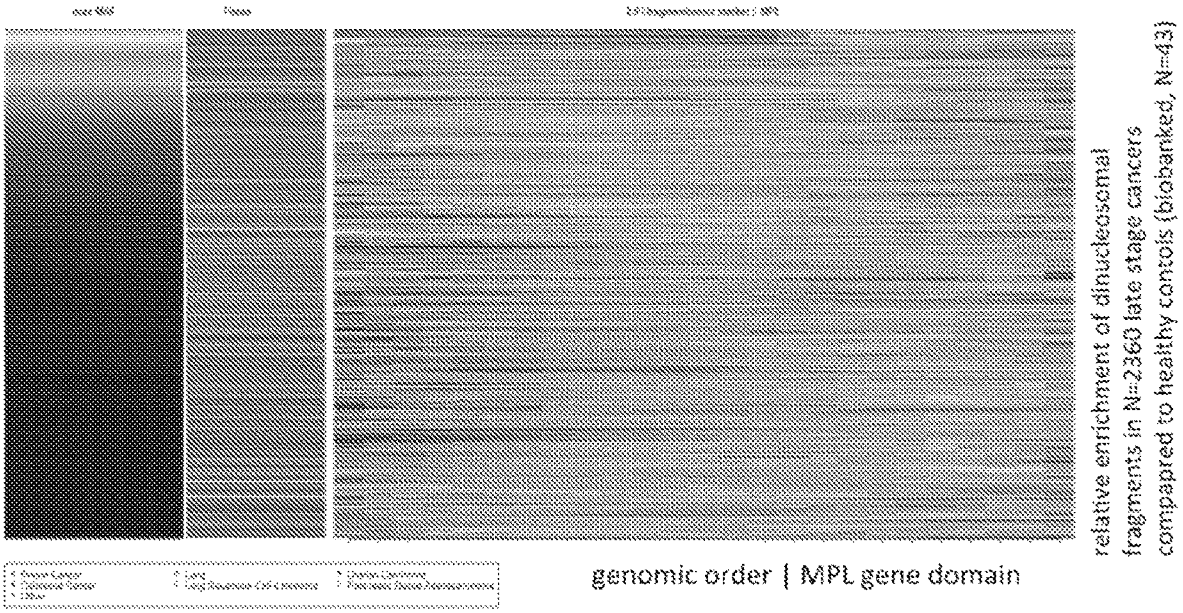
FIG. 32A shows a plot of relative enrichment of dinucleosomal fragments in the MPL gene domain across 2360 late stage cancer subjects and 43 healthy controls.

Example 5: Cell-Free DNA Fragmentation Patterns (Fragmentome Profiling or "Fragmentomics" Analysis) Reveal Changes Indicative of Immune Cell Type Presence Associated with Cancer A set of fragmentome profiles comprising fragment start distributions for a locus of the MPL gene (MPL Proto-Oncogene, Thrombopoietin Receptor) represented by a single contiguous stretch of chrl: 43814893-43815072, was examined across (i) a set of 2,360 late stage malignant cases spanning at least 6 different tissues and (ii) 43 healthy biobanked control subjects. For each fragmentome profile, a dinucleosomal ratio, as defined as a number of observed dinucleosomal fragments (having a length in the range of ~240 to ~360 bp) divided by a number of mono-nucleosomal fragments (having a length of less than 240 bp), was calculated in a sliding 30 bp window. Next, a residual of such a dinucleosomal ratio was obtained for each fragmentome profile, by subtracting a median profile across healthy control subjects. As shown in FIG. 32A, a residual plot was generated, as represented by a heat map, with rows corresponding to samples and columns corresponding to individual windows spanning an MPL targeted domain of 180 bp, and with the y-axis ordered by increasing maximum mutation allele frequency (MAF) observed in a liquid biopsy assay.

Figure 32B:
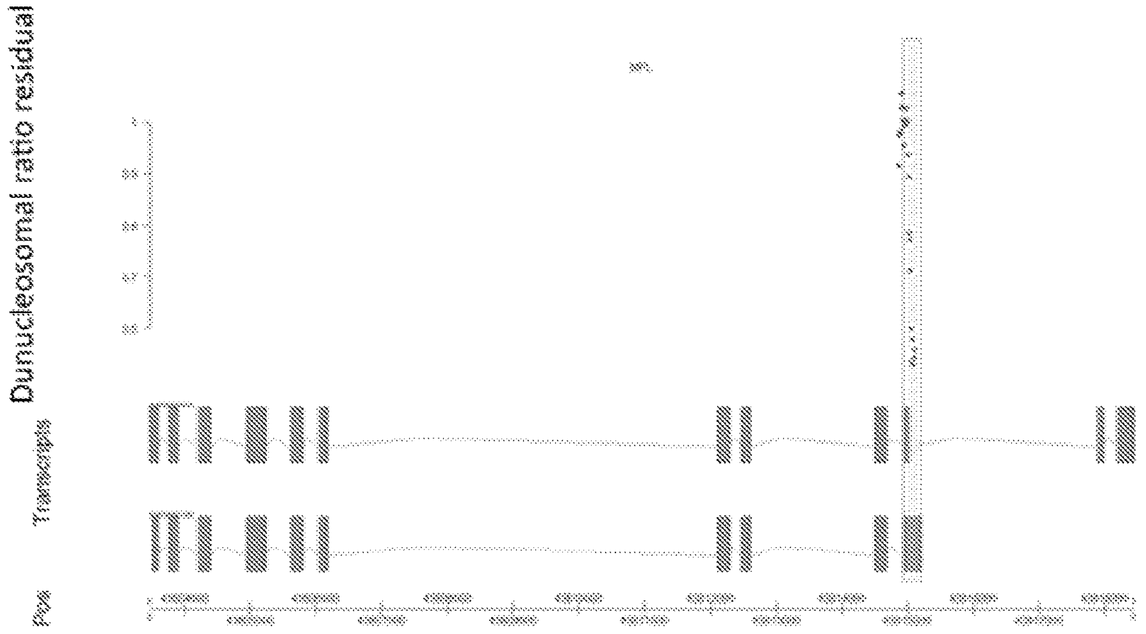
FIGS. 32B and 32C show an example of a breakpoint in residual dinucleosomal ratio signal in an alternative transcript of the MPL gene.
Figure 32C:
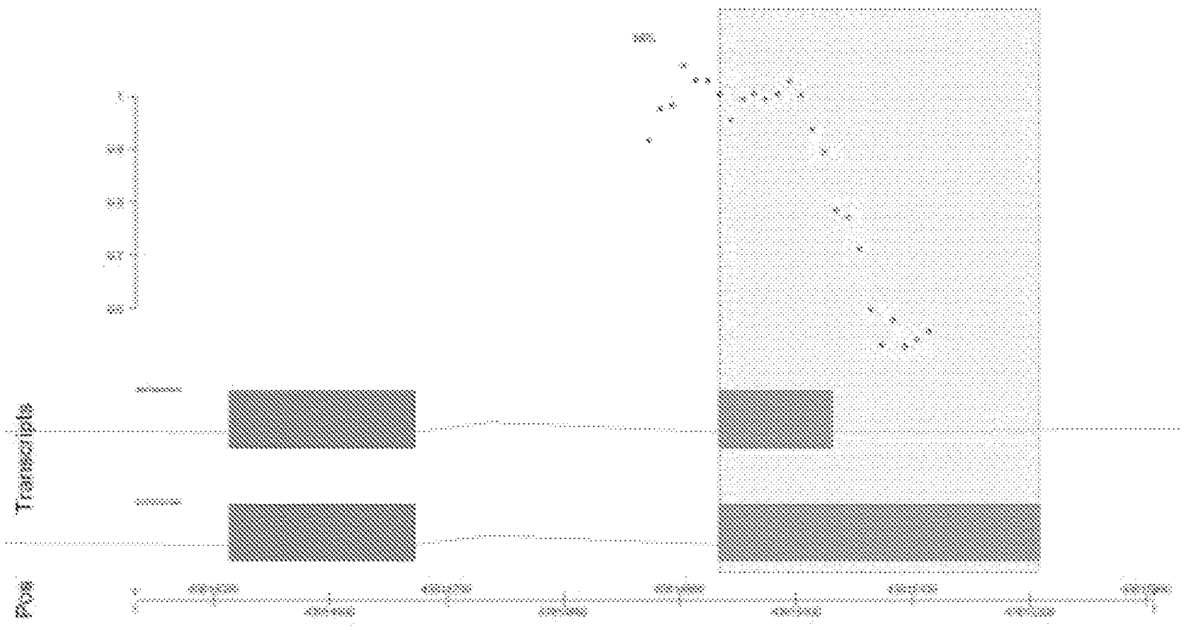

High MAF samples (greater than about 30%) (i.e., those from subjects with the highest tumor burden and thus representing relatively advanced metastatic disease) exhibited enrichment of dinucleosomal residual indicative of short-ranged (sub-nucleosomal, less than ~180 bp) differential chromatin architecture in high tumor burden cancers compared to healthy control subjects. Examining ENSEMBL transcription structure of the targeted MPL domain revealed a breakpoint in residual dinucleosomal ratio signal (as shown in FIGS. 32B and 32C), which was associated with transcript structure variation with enrichment of fragments in high tumor burden cancer samples coinciding with truncated exon usage in an alternative transcript of MPL. Such a breakpoint is indicative of an alternative splicing event in the MPL gene, and represents a sub-nucleosomal fragmentome signal that spans two different transcript, with one transcript being the truncated form of another. The truncated form of the transcript (canonical form) is shown on top, while the non-canonical form of the transcript is shown on the bottom.

Further examination of breakpoint association with tissue-specific alternative exon usage (as shown in FIG. 32C), reveals the identification of defining transmembrane Mpl variants, MPLK (full) and MPLP (truncated). The MPLP variant was detected in monocytes, B-lympocyte, and T cell populations, while MPLK mRNA expression was low in monocytes, B cells, and T cells. We observe a breakpoint associated with the edge of the shorter transcript, while a small fraction (i.e., a lower signal) associated with the longer transcript. The longer transcript is observed in immune cell type populations and can be indicative of cancer presence and/or aggressiveness. These results indicate that relative to healthy normal control subjects, subjects with a high tumor burden carry an additional cell-free DNA load, which is enriched in an MPLP signature. Such a signature is indicative of an immune cell type presence associated with cancer presence and aggressiveness (e.g., as described in [Different mutations of the human c-mpl gene indicate distinct hematopoietic diseases, Xin He et al, Journal of Hematology & Oncology20136:11]. Hence, these results indicate that fragmentomics (analysis of fragmentome profiles) enabled the detection and identification of the presence or relative increased amount of immune cell types, whose presence is associated with cancer.

What is claimed is:

1. A method of determining whether a subject has or does not have cancer, the method comprising:

obtaining cell-free deoxyribonucleic acid (DNA) fragments derived from the subject;

sequencing at least a portion of the cell-free DNA fragments, whereby genetic sequence information is produced;

mapping, based on the genetic sequence information, sequence reads to a reference genome and computing subject fragmentome data, wherein the computed subject fragmentome data comprises at least one of: (i) a length of the DNA fragments that align with each of a plurality of base positions in the genome, (ii) a number of the DNA fragments that align with each of a plurality of base positions in the genome, or (iii) a number of the DNA fragments that start or end at each of a plurality of base positions;

constructing, from the subject fragmentome data, a subject multi-parametric fragmentome profile model representative of the subject's cell-free DNA fragments, wherein the subject multiparametric fragmentome profile comprises at least three values indicating a quantitative measure of a characteristic selected from: (i) DNA sequences mapping to a genetic locus, and (ii) DNA sequences starting at a genetic locus;

classifying the subject by applying a trained variant-free fragmentome machine learning classifier to the subject multi-parametric fragmentome profilemodel, wherein the trained variant-free fragmentome machine learning classifier operates without using base identity as an input feature, wherein the trained variant-free fragmentome machine learning classifier is trained by:

obtaining, from a plurality of different classes representing a set of subjects with a tumor-related shared characteristic, fragmentome training data comprising at least one of (i) a length of the DNA fragments that align with each of the plurality of base positions in the genome, (ii) a number of the DNA fragments that align with each of the plurality of base positions in the genome, or (iii) a number of the DNA fragments that start or end at each of the plurality of base positions multi-parametric fragmentome models computed from cell-free DNA fragments of subjects in the class, constructing, from the fragmentome training data, multi-parametric fragmentome training profiles, wherein each multi-parametric fragmentome training profile comprises the tumor-related characteristic and at least three values indicating a quantitative measure of a characteristic selected from: (i) DNA sequences mapping to a genetic locus, (ii) DNA sequences starting at a genetic locus, and (iii) DNA sequences ending at a genetic locus, and training, by a computer, a machine learning algorithm to create a probabilistic classifier with the multi-parametric fragmentome training profile data to thereby generating the trained variant-free fragmentome machine learning classifier configured to classify the presence or absence of cancer; and outputting, by the trained variant-free fragmentome machine learning classifier, a determination that the subject has or does not have cancer based on the subject multi-parametric fragmentome model.

2. The method of claim 1, wherein the subject fragmentome data comprises data selected from the group consisting of: (a) start position of DNA fragments sequenced, (b) end position of sequenced DNA fragments, (c) number of unique sequenced DNA fragments that cover a mappable position, (d) length of sequenced DNA fragments, (e) a likelihood that a mappable base-pair position will appear at a terminus of a sequenced DNA fragment, (f) a likelihood that a mappable base-pair position will appear within a sequenced DNA fragment as a consequence of differential nucleosome occupancy, (g) a sequence motif of sequenced DNA fragments, (h) GC content, (i) sequenced DNA fragment length distribution, and (j) methylation status.

3. The method of claim 2, wherein constructing, from the subject fragmentome data, the subject multi-parametric fragmentome model profile representative of the subject's cell-free DNA fragments comprises mapping to each of a plurality of base positions or regions of a genome, one or more distributions selected from the group consisting of:

(i) a distribution of the number of unique cell-free DNA fragments containing a sequence that covers the mappable position in the genome, (ii) a distribution of the fragment lengths for each of at least some of the cell-free DNA fragments such that the DNA fragment contains a sequence that covers the mappable position in the genome, and (iii) a distribution of the likelihoods that a mappable base-pair position will appear at a terminus of a sequenced DNA fragment.

4. The method of claim 3, wherein the plurality of base positions or regions of a genome include at least one base position or region associated with one or more of the genes from the group of point mutations in members of the group of: AKT1, ALK, APC, AR, ARAF, ARIDIA, ATM, BRAF, BRCA1, BRCA2, CCND1, CND2, CCNE1, CDH1, CDK4, CDK6, CDKN2A, CDKN2B, FGFR1, FGFR2, FGFR3, GATA3, GNA11, GNAQ, GNAS, HNF1A, HRAS, IDH1, IDH2, JAK2, JAK3, KIT, KRAS, MAP2K1, MAP2K2, MET, MLH1, MPL, MYC, NF1, NFE2L2, NOTCH1, NTRK1, PDGFRA, PIK3CA, PTEN, NPM1, NRAS, PTPN11, RAF1, RB1, RET, RHEB, RHOA, RIT1, ROS1, SMAD4, SMO, SRC, STK11, TERT, TP53, TSC1, VHL, Copy number variations in members of the group of: AAR, BRAF, CCND1, CCND2, CCNE1, CDK4, CDK6, EGFR, ERBB2, FGFR1, FGFR2,KIT, KRAS, MET, MYC, PDGFRA, PIK3CA, RAF1, Fusions in the group of: ALK, FGFR2, FGFR3, NTRK1, RET, ROS1, Indels in the group of: EGFR (exons 19 & 20), ERBB2 (exons 19 & 20), MET (exon 14 skipping).

5. The method of claim 3, wherein the mapping comprises mapping a plurality of values, to each of a plurality of base positions or regions of a genome.

6. The method of claim 4, wherein at least one of the plurality of values is selected from the group consisting of (a) start position of DNA fragments sequenced, (b) end position of sequenced DNA fragments, (c) number of unique sequenced DNA fragments that cover a mappable position, (d) length of sequenced DNA fragments, (e) a likelihood that a mappable base-pair position will appear at a terminus of a sequenced DNA fragment, (f) a likelihood that a mappable base-pair position will appear within a sequenced DNA fragment as a consequence of differential nucleosome occupancy, or (g) a sequence motif of sequenced DNA fragments.

7. The method of claim 1, wherein constructing, from the subject fragmentome data, the subject multi-parametric fragmentome model profile representative of the subject's cell-free DNA fragments comprises applying, by a computer, one or more mathematical transforms to generate the subject multi-parametric fragmentome model profile.

8. The method of claim 1, wherein the subject multi-parametric fragmentome model profile is a joint distribution model of a plurality of variables selected from the group consisting of: (a) start position of DNA fragments sequenced, (b) end position of sequenced DNA fragments, (c) number of unique sequenced DNA fragments that cover a mappable position, (d) length of sequenced DNA fragments, (e) a likelihood that a mappable base-pair position will appear at a terminus of a sequenced DNA fragment, (f) a likelihood that a mappable base-pair position will appear within a sequenced DNA fragment as a consequence of differential nucleosome occupancy, and (g) a sequence motif of sequenced DNA fragments.

9. The method of claim 1, further comprising identifying in the subject multi-parametric fragmentome model profile, one or more peaks, each peak having a peak distribution width and a peak coverage.

10. The method of claim 8, further comprising detecting one or more deviations between the subject multi-parametric fragmentome model profile representative of the cell-free DNA fragments and a reference multi-parametric fragmentome model.

11. The method of claim 10, wherein the deviation is selected from the group consisting of:

(i) an increase in the number of reads outside a nucleosome region, (ii) an increase in the number of reads within a nucleosome region, (iii) a broader peak distribution relative to a mappable genomic location, (iv) a shift in location of a peak, (v) identification of a new peak, (vi) a change in depth of coverage of a peak, (vii) a change in start position around a peak, and (viii) a change in fragment sizes associated with a peak.

12. The method of claim 1, further comprising determining a contribution of the subject multi-parametric fragmentome model profile attributed to (i) apoptotic processes in cells from which the cell-free DNA originated or (ii) necrotic processes in cells from which the cell-free DNA originated.

13. The method of claim 1, further comprising performing a multi- parametric analysis to (i) measure RNA expression of the cell-free DNA fragments, (ii) measure methylation of the cell-free DNA fragments, (iii) measure a nucleosomal mapping of the cell-free DNA fragments, or (iv) identify the presence of one or more somatic single nucleotide polymorphisms in the cell-free DNA fragments or one or more germline single nucleotide polymorphisms in the cell-free DNA fragments.

14. The method of claim 1, further comprising generating a distribution score comprising values indicating a number of the DNA fragments with dinucleosomal protection or a number of the DNA fragments with mononucleosomal protection.

15. The method of claim 1, further comprising estimating a mutation burden of the subject.

16. The method of claim 1, wherein each of the plurality of different classes is selected from the group consisting of: healthy, breast cancer, colon cancer, lung cancer, pancreatic cancer, prostate cancer, ovarian cancer, melanoma, and liver cancer.

17. The method of claim 1, wherein the tumor-related shared characteristic may be selected from the group consisting of: a tumor type, an inflammatory condition, an apoptotic condition, a necrotic condition, a tumor recurrence, and resistance to a treatment.

18. The method of claim 1, wherein the subject fragmentome data comprises one or more of: (i) a number of cell-free DNA fragments mapping to the base position, (ii) a length of each fragment mapping to the base position, (iii) a number of fragments starting at the base position, (iv) a number of fragments ending at the base position, or (v) any of the foregoing as a function of fragment length.

19. The method of claim 1, wherein the set of subjects comprise at least a cohort of healthy subjects and a cohort of subjects having cancer.

20. The method of claim 1, wherein the multi-parametric fragmentome models computed from cell-free DNA fragments of subjects in the class comprises training profiles comprise a joint distribution model of a plurality of variables selected from the group consisting of: (a) start position of DNA fragments sequenced, (b) end position of sequenced DNA fragments, (c) number of unique sequenced DNA fragments that cover a mappable position, (d) length of sequenced DNA fragments, (e) a likelihood that a mappable base-pair position will appear at a terminus of a sequenced DNA fragment, (f) a likelihood that a mappable base-pair position will appear within a sequenced DNA fragment as a consequence of differential nucleosome occupancy, and (g) a sequence motif of sequenced DNA fragments.

* * * * *